United States Patent
Singh et al.

(10) Patent No.: US 10,570,375 B2
(45) Date of Patent: *Feb. 25, 2020

(54) ADHESIVE SIGNATURE-BASED METHODS FOR THE ISOLATION OF STEM CELLS AND CELLS DERIVED THEREFROM

(71) Applicant: Georgia Tech Research Corporation, Atlanta, GA (US)

(72) Inventors: Ankur Singh, Ithaca, NY (US); Shalu Suri, Ithaca, NY (US); Todd Christopher McDevitt, Atlanta, GA (US); Hang Lu, Atlanta, GA (US); Andres Jose Garcia, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,918

(22) Filed: Oct. 2, 2018

(65) Prior Publication Data

US 2019/0040364 A1 Feb. 7, 2019

Related U.S. Application Data

(62) Division of application No. 14/128,547, filed as application No. PCT/US2012/043552 on Jun. 21, 2012, now Pat. No. 10,106,780.

(60) Provisional application No. 61/499,323, filed on Jun. 21, 2011.

(51) Int. Cl.
| | |
|---|---|
| C12N 5/074 | (2010.01) |
| C12N 5/0797 | (2010.01) |
| C12Q 1/686 | (2018.01) |
| G01N 33/569 | (2006.01) |

(52) U.S. Cl.
CPC ......... *C12N 5/0696* (2013.01); *C12N 5/0623* (2013.01); *C12Q 1/686* (2013.01); *G01N 33/56966* (2013.01); *C12N 2506/45* (2013.01); *C12N 2509/10* (2013.01); *C12N 2527/00* (2013.01); *C12N 2539/10* (2013.01)

(58) Field of Classification Search
CPC ........... C12N 5/0696; C12N 5/0623; C12N 2506/45; C12N 2509/10; C12N 2527/00; C12N 2539/10; C12Q 1/686; G01N 33/56966

See application file for complete search history.

(56) References Cited

U.S. PATENT DOCUMENTS

| | | | |
|---|---|---|---|
| 10,106,780 B2* | 10/2018 | Singh | C12N 5/0696 |
| 2002/0012903 A1 | 1/2002 | Goldman et al. | |
| 2004/0018531 A1 | 1/2004 | Jamieson et al. | |
| 2008/0227137 A1 | 9/2008 | Zhang et al. | |
| 2010/0003265 A1 | 1/2010 | Scheffler et al. | |
| 2010/0247493 A1 | 9/2010 | Rust et al. | |
| 2014/0314675 A1 | 10/2014 | Yamazaki et al. | |
| 2014/0357506 A1 | 12/2014 | Singh et al. | |

FOREIGN PATENT DOCUMENTS

| | | |
|---|---|---|
| JP | 2011-015662 | 1/2011 |
| JP | 2012-029597 | 2/2012 |
| WO | 01/68815 | 9/2001 |
| WO | 2005/056777 | 6/2005 |
| WO | 2008/057162 | 5/2008 |
| WO | 2009/043057 | 4/2009 |
| WO | 2010/141801 | 12/2010 |
| WO | 2011/053257 | 5/2011 |

OTHER PUBLICATIONS

Reyes et al., J Biomed Mater. Res 67A: 328-333, 2003.*
Khalili et al., Int. J. Mol. Sci., 16, 18149-18184, 2015.*
Chen et al., Development, 140: 255-265, 2013.*
Aasen et al. "Efficient and rapid generation of induced pluripotent stem cells from human keratinocytes" Nature Biotechnology 26(11):1276-1284 (Nov. 2008).
Balaban et al. "Force and focal adhesion assembly: a close relationship studied using elastic micropatterned substrates" Nature Cell Biology 3:466-472 (2001).
Bates et al. "Individual Embryonic Fibroblasts Express Multiple β Chains in Association with the av Integrin Subunit" Journal of Biological Chemistry 266(28):18593-18599 (Oct. 5, 1991).
Bratt-Leal et al. "Incorporation of Biomaterials in Multicellular Aggregates Modulates Pluripotent Stem Cell Differentiation" Biomaterials 32(1):48-56 (2011).
Chan et al. "Lice cell imaging distinguishes bona fide human iPS cells from partially reprogrammed cells" Nature Biotechnology 27(11):1033-1037 (2009).
Chen et al. "Actin-myosin contractility is responsible for the reduced viability of dissociated human embryonic stem cells" Cell Stem Cell 7(2):240-248 (2010).
Cho et al. "Highly efficient and large-scale generation of functional dopamine neurons from human embryonic stem cells" Proceedings of the National Academy of Sciences 105(9):3392-3397 (2008).
Dick et al. "Two new protocols to enhance the production and isolation of human induced pluripotent stem cell lines" Stem Cell Research 6:158-167 (2011).
Dumbauld et al. "Contractility Modulates Cell Adhesion Strengthening Through Focal Adhesion Kinase and Assembly of Vinculin-Containing Focal Adhesions" Journal of Cellular Physiology 223(3):746-756 (2010).
Dumbauld et al. "Focal Adhesion Kinase-Dependent Regulation of Adhesive Force Involves Vinculin Recruitment to Focal Adhesions" Biology of the Cell 102(4):203-213 (2010).
Fu et al. "Mechanical regulation of cell function with geometrically modulated elastomeric substrates" Nature Methods 7(9):733-736 (2010).

(Continued)

*Primary Examiner* — Thaian N. Ton
(74) *Attorney, Agent, or Firm* — Myers Bigel, P.A.

(57) ABSTRACT

The present invention provides for methods of isolating a stem cell or cell derived therefrom from a mixture of cells, for example, a mixture of adherent cells in culture. Cell isolation is achieved by the application of selective detachment forces.

8 Claims, 37 Drawing Sheets

(56) References Cited

OTHER PUBLICATIONS

Gallant et al. "Cell Adhesion Strengthening: Contributions of Adhesive Area, Integrin Binding, and Focal Adhesion Assembly" Molecular Biology of the Cell 16:4329-4340 (2005).
Garcia et al. "Force Required to Break a5β1 Integrin-Fibronectin Bonds in Intact Adherent Cells Is Sensitive to Integrin Activation State" The Journal of Biological Chemistry 273(18):10988-10993 (1998).
Garcia et al. "Two-stage Activation for a5β1 Integrin Binding to Surface-adsorbed Fibronectin" The Journal of Biological Chemistry 273(52):34710-34715 (1998).
Geiger et al. "Assembly and mechanosensory function of focal contacts" Current Opinion in Cell Biology 13:584-592 (2001).
International Preliminary Report on Patentability Corresponding to International Application No. PCT/US2012/043552 (7 Pages) (dated Jan. 9, 2014).
International Search Report and Written Opinion Corresponding to International Application No. PCT/US2012/043552 (10 pages) (dated Sep. 5, 2012).
Kehat et al. "Human embryonic stem cells can differentiate into myocytes with structural and functional properties of cardiomyocytes" Journal of Clinical Investigation 108(3):407-414 (Aug. 2001).
Kuroda et al. "Unique multipotent cells in adult human mesenchymal cell populations" Proceedings of the National Academy of Sciences 107(19):8639-8643 (May 11, 2010).
Lister et al. "Human DNA methylomes at base resolution show widespread epigenomic differences" Nature 462 (7271):315-322 (2009).
Lu et al. "Microfluidic Shear Devices for Quantitative Analysis of Cell Adhesion" Analytical Chemistry 76 (18):5257-5264 (2004).
Maitra et al. "Expression of a and β integrins during terminal differentiation of cardiomyocytes" Cardiovascular Research 47(4):715-725 (Sep. 2000).
McDonald et al. "Fabrication of microfluidic systems in poly(dimethylsiloxane)" Electrophoresis 21:27-40 (2000).
Meng et al. "Characterization of integrin engagement during defined human embryonic stem cell culture" FASEB Journal 24(4):1056-1065 (2010).
Moon et al. "Generation, Culture, and Differentiation of Human Embryonic Stem Cells for Therapeutic Applications" Molecular Therapy 13(1):5-14 (2006).
Mummery et al. "Differentiation of Human Embryonic Stem Cells to Cardiomyocytes: Role of Coculture with Visceral Endoderm-Like Cells" Circulation 107(21):2733-2740 (Jun. 3, 2003).
Nagaoka et al. "Culture of human pluripotent stem cells using completely defined conditions on a recombinant E-cadherin substratum" BMC Developmental Biology 10(60):1-12 (2010).
Ohgushi et al. "Molecular Pathway and Cell State Responsible for Dissociation-Induced Apoptosis in Human Pluripotent Stem Cells" Cell Stem Cell 7:225-239 (2010).
Richards et al. "Human feeders support prolonged undifferentiated growth of human inner cell masses and embryonic stem cells" Nature Biotechnology 20:933-936 (Sep. 2002).
Samavarchi-Tehrani et al. "Functional Genomics Reveals a BMP-Driven Mesenchymal-to-Epithelial Transition in the Initiation of Somatic Cell Reprogramming" Cell Stem Cell 7:64-77 (2010).
Singh et al. "Adhesive Signature-based, Label-free Isolation of Human Pluripotent Stem Cells" Nature Methods 10 (5):438-444 (2013).
Takada et al. "The integrins" Genome Biology 8(5):215 (2007).
Terpe et al. "Alpha 6 integrin distribution in human embryonic and adult tissues" Histochemistry 101:41-49 (1994).
Walia et al. "Enrichment for Breast Cancer Cells with Stem/Progenitor Properties by Differential Adhesion" Stem Cells and Development 19(8):1175-1182 (2010).
Xu et al. "Feeder-free growth of undifferentiated human embryonic stem cells" Nature Biotechnology 19:971-974 (Oct. 2001).
Yu et al. "Induced Pluripotent Stem Cell Lines Derived from Human Somatic Cells" Science 318(5858):1917-1920 (2007).
U.S. Appl. No. 16/148,784; office action dated Feb. 4, 2019.

\* cited by examiner hiPSC SEEDED AFTER
FACS ENRICHMENT
(24 H, SIGNIFICANT
CELL DEATH)

hiPSC AFTER 48 H
(NO CONPACT
EPITHELIAL COLONIES)

HUMAN DERMAL
FIBROBLASTS

DERMAL
hiPSC (11b)

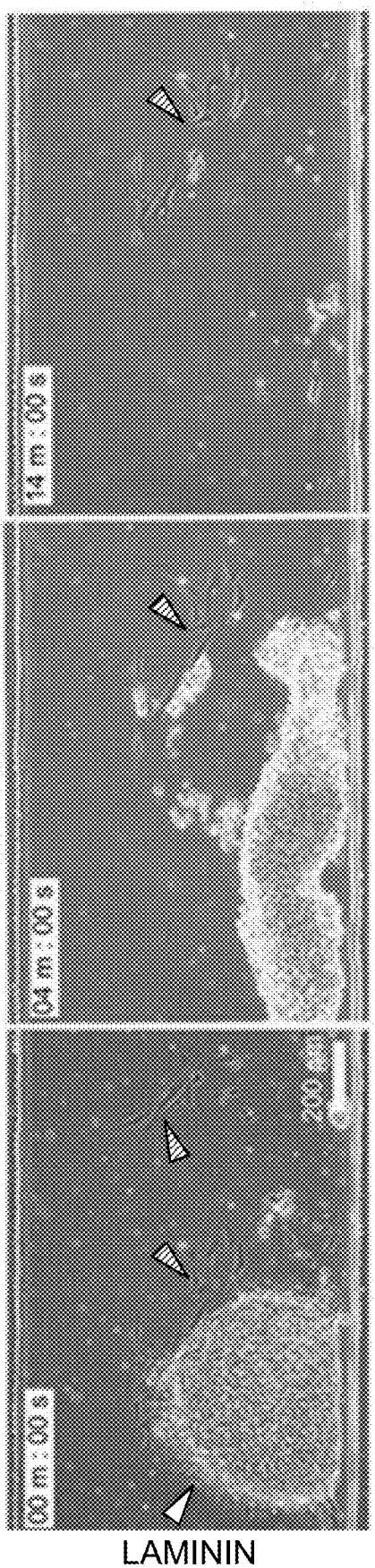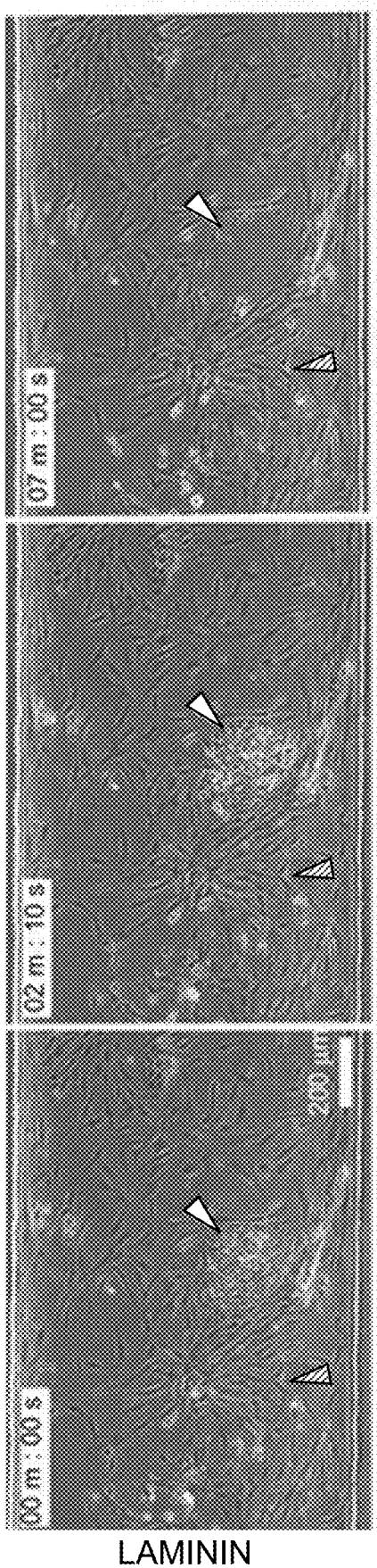
FIG. 5E
FIG. 5F

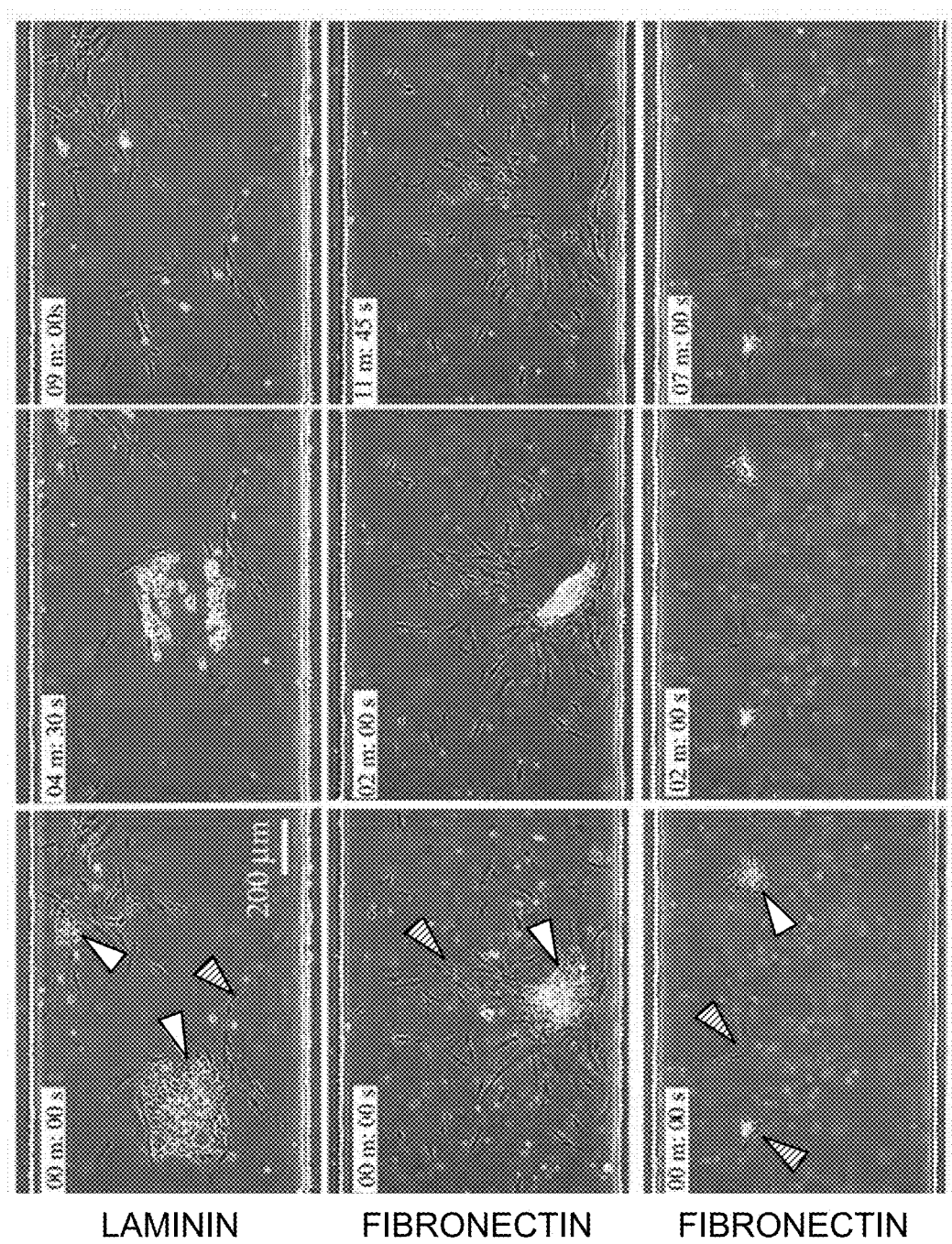

PASSAGE 1

μSHEAR 100 DYNES/cm²     μSHEAR 750 DYNES/cm²

PASSAGE 10
μSHEAR 100 DYNES/cm²

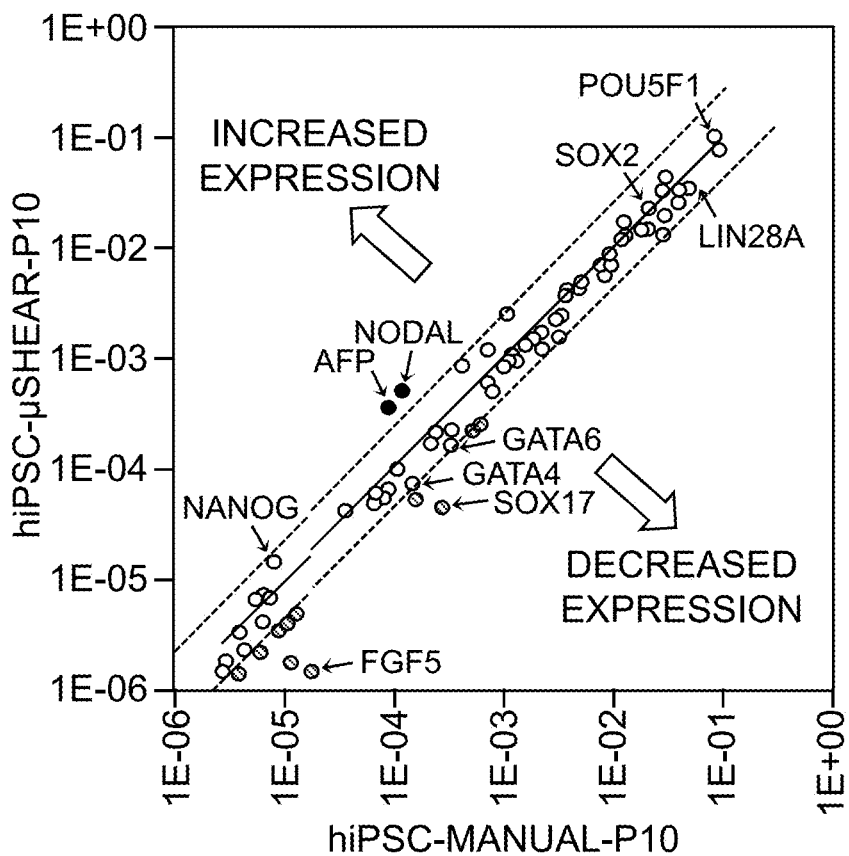
*FIG. 12*
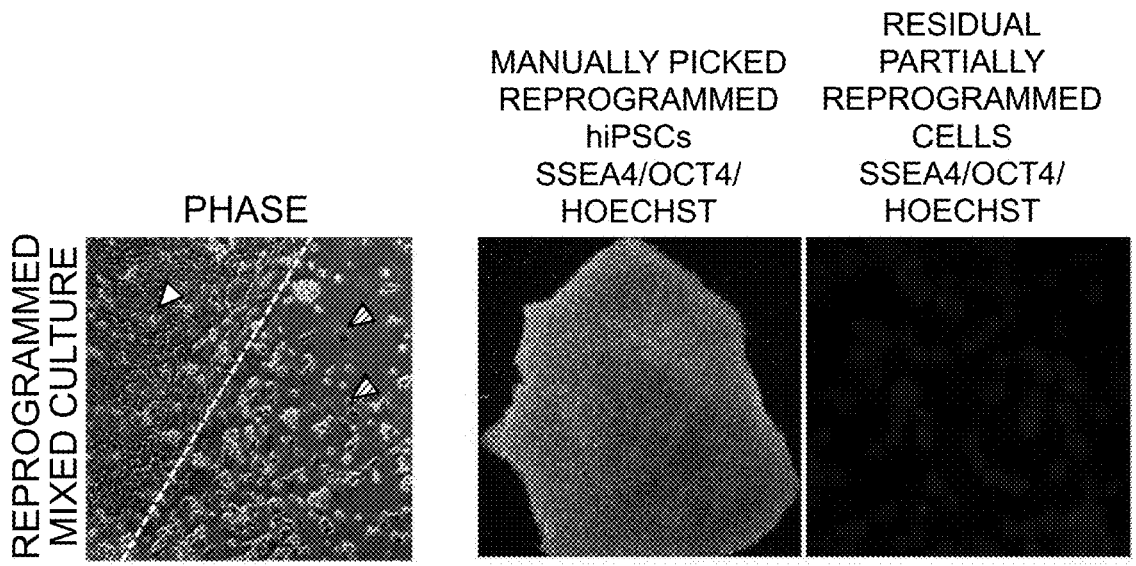
*FIG. 13A*  *FIG. 13B*

ADHESIVE SIGNATURE-BASED METHODS FOR THE ISOLATION OF STEM CELLS AND CELLS DERIVED THEREFROM

RELATED APPLICATION INFORMATION

This application is a divisional of U.S. patent application Ser. No. 14/128,547, filed Mar. 28, 2014 (allowed), which is a 35 U.S.C. § 371 national phase application of International Application Serial No. PCT/US2012/043552, filed Jun. 21, 2012, which claims the benefit, under 35 U.S.C. § 119(e), of U.S. Provisional Application No. 61/499,323, filed Jun. 21, 2011, the entire contents of each of which are incorporated by reference herein.

STATEMENT OF FEDERAL SUPPORT

The invention was made with Government support under Contract Numbers GM659180 and CA144825, awarded by the National Institutes of Health, and Contract Number DBI0649833, awarded by the National Science Foundation. The Government has certain rights in the invention.

FIELD OF THE INVENTION

The present invention relates to methods for the isolation of stem cells and cells derived therefrom. In particular, the present invention relates to methods for the isolation of stem cells and cells derived therefrom based on the use of selective detachment force.

BACKGROUND OF THE INVENTION

Generation of human induced pluripotent stem (hiPS) cells from fibroblasts and other somatic cells represents a highly promising strategy to produce auto- and allogenic cell sources for numerous therapeutic approaches as well as novel models of human development and disease[2-4]. The reprogramming breakthrough[1,3,5] involved retroviral transduction of the four factors Oct3/4 (also known as Pou5fl), Sox2, Klf4, and c-Myc in fibroblasts, and since then advances in reprogramming methods have been developed[6] using retro- and lenti-viruses[1,2,7,8], transposons[9], loxP-flanked lentivirus[10], nonintegrating adenoviruses[11,12] and plasmids[13], proteins[14] and RNA[15,16] The reprogrammed cells are typically cultured on mouse embryonic fibroblast (MEF) or isogenic human fibroblast feeder layers, and subsequently transferred to feeder layers by mechanical dissociation of pluripotent cell-like colonies for propagation[1,3,17] Residual parental or feeder-layer cells introduce experimental variability, pathogenic contamination, and potential immnunogenicity[18]. iPS cell cultures are often heterogeneous because of the presence of undifferentiated stem cells, non- and partially-induced parental cells and spontaneously differentiated derivatives[19]. The unavoidable problem of spontaneous differentiation arises from low cell splitting ratios[20,21], sub-optimal feeder cultures[22], growth factors[23], and feeder layer-free substrate quality[24]. Even under the best of cell culture conditions, some degree of spontaneous differentiation is common and occurs along seemingly random pathways[25-29]. Spontaneously differentiated (SD)-iPS cells display reduced pluripotency and often contaminate iPS cell cultures, resulting in overgrowth of cultures and compromising the quality of residual pluripotent stem cells[23,30,19]. The problem of cell contamination is also evident in directed differentiation protocols to generate specific lineages[31]. For example, differentiation to neural lineages is a step-wise process and intermediate stages like neural rosettes require manual hand-picking because they are contaminated with fibroblast-like cells and residual undifferentiated pluripotent stem cells[32,33].

Current methods for propagation of high-quality iPS cell and embryonic stem (hES) cell cultures rely primarily on manual isolation[26,27,34-37] alone or in combination with enzymatic dissociation methods. Similar to undifferentiated pluripotent colonies, multi-potent neural rosettes and neurospheres are typically handpicked based on visual inspection and qualitative metrics and transferred for further differentiation into neural progenitors[31,32,38]. Such methods are tedious, time-intensive, require skilled labor, and are heavily dependent on the ability to morphologically recognize undifferentiated cells. Furthermore, the lack of quality controls affects the reproducibility and consistency of these cultures. Whereas many reagents have been developed for bulk enzymatic passaging, such methods are not selective for iPS cells and therefore unwanted cells are often transferred[35,36,39]. Furthermore, many enzymatic methods can cause karyotypic abnormalities compared to manual or mechanical passaging[34-37]. Other technical disadvantages with enzymatic passaging include the need to re-aggregate the dissociated iPS cells as multi-cellular colonies by re-plating on feeder-cells for improved clonal survival[20]. Although flow cytometry sorting[21,23] based on antibody-labeled phenotypic markers can significantly enrich the purity of undifferentiated populations, this method requires single cell dissociation of iPS cells, which induces contractility-mediated programmed cell death[40,41], and the plated cells fail to form tightly packed colonies (FIG. 1D). Further, the use of antibody labels is less desirable for therapeutic applications.

Because current techniques for iPS cell purification remain a bottleneck in passaging procedures and suffer from a number of other drawbacks, there is a great need to develop improved technologies that can more efficiently separate colonies of undifferentiated (UD)-iPS cells from contaminating parental cells, feeder cells, or differentiated cells without requiring tedious manual isolation, enzymatic dissociation of iPS cells into single cells and/or labeling with antibodies or other reagents.

SUMMARY OF THE INVENTION

The present invention is based, in part, on the inventors' demonstration of a unique "adhesive signature" associated with stem cells (e.g., undifferentiated stem cells) and cells derived therefrom that is dictated by their phenotypic state. The present invention utilizes the differences in the adhesion strength of stem cells, as well as stem cell derivatives, as compared with other cells to selectively isolate cell type(s) of interest using detachment forces. Advantageously, the methods of the invention are amenable to high throughput analysis, real-time imaging, in-line biochemical, genetic and/or cytometric processing.

Accordingly, as one aspect, the invention provides a method of isolating a cell of interest from a mixture of animal cells (e.g., cultured animal cells), wherein the cell of interest is a stem cell or a cell derived therefrom, the method comprising: subjecting a mixture of animal cells adhered to a substrate comprising the cell of interest and at least one other cell type to a detachment force that is sufficient to selectively detach the cell of interest from the substrate relative to the at least one other cell type in the mixture of animal cells, thereby isolating the cell of interest from the mixture of animal cells.

In embodiments, the method comprises isolating a stem cell from the mixture of animal cells. Optionally, the stem cell is an embryonic stem (ES) cell or an induced pluripotent stem (iPS) cell. Optionally, the stem cell is an adult stem cell.

In embodiments wherein the cell of interest is a stem cell, the at least one other cell type is a feeder cell, a parental somatic cell, a partially reprogrammed cell, a spontaneously differentiated stem cell and/or a directly differentiated cell.

In embodiments, the cell of interest is a stem cell that grows in culture as part of a cluster.

In embodiments, the cell of interest is a stem cell that detaches from the substrate as part of a cluster of stem cells.

In embodiments, the isolated cell of interest is an isolated stem cell that maintains expression of at least one pluripotency marker and/or retains the ability to produce two or more different cells types.

In embodiments, the cell of interest is a stem cell and the detachment force that is sufficient to selectively detach the stem cell provides a wall shear stress in the range of 70 to 160 dynes/cm$^2$, optionally, in the range of 80 to 125 dynes/cm$^2$.

In embodiments, the method comprises isolating a stem cell-derived lineage committed cell from the mixture of animal cells, optionally, a stem cell-derived neural committed cell such as a neural rosette cell.

When the cell of interest is a stem cell-derived lineage committed cell, in embodiments the at least one other cell type is a stem cell, a feeder cell, a parental somatic cell, a partially reprogrammed cell, a spontaneously differentiated stem cell, a progenitor cell and/or a terminally differentiated cell.

In embodiments, the detachment force that is sufficient to selectively detach the stem cell-derived lineage committed cell provides a wall shear stress in the range of 40 to 160 dynes/cm$^2$.

In embodiments, the method comprises isolating a stem cell-derived progenitor cell from the mixture of animal cells; optionally, the stem cell-derived progenitor cell is a stem cell-derived neural progenitor cell or a hematopoietic progenitor cell.

In embodiments, the cell of interest is a stem cell-derived progenitor cell and the at least one other cell type is a stem cell, a feeder cell, a parental somatic cell, a partially reprogrammed cell, a spontaneously differentiated stem cell, a lineage committed cell and/or a terminally differentiated cell.

In embodiments, the detachment force that is sufficient to selectively detach the stem cell-derived progenitor cell provides a wall shear stress in the range of 20-70 dynes/cm$^2$.

In embodiments, the cell of interest is a stem cell-derived terminally differentiated cell, optionally a cardiomyocyte.

In embodiments, the cell of interest is a stem cell-derived terminally differentiated cell and the at least one other cell type is a stem cell, a feeder cell, a parental somatic cell, a partially reprogrammed cell, a spontaneously differentiated stem cell, a lineage committed cell and/or a progenitor cell.

In embodiments, the detachment force that is sufficient to selectively detach the stem cell-derived progenitor cell provides a wall shear stress in the range of 20-70 dynes/cm$^2$.

In embodiments of the present invention, the cell of interest detaches at a lower detachment force as compared with the at least one other cell type.

In embodiments, the cell of interest detaches at a higher detachment force as compared with the at least one other cell type.

In embodiments, the isolated cell of interest is viable and/or maintains the ability to divide and produce progeny cells.

In embodiments, pluralities of cells of interest are isolated with at least 90% purity.

In embodiments, at least 70% of the cells of interest in the mixture of animal cells are isolated.

In embodiments, the cell of interest constitutes 40% or less of the cells in the mixture of animal cells, optionally 10% or less of the cells in the mixture of animal cells.

In embodiments, the cell of interest constitutes at least 60% of the cells in the mixture of animal cells, optionally at least 90% of the cells in the mixture of animal cells.

In embodiments, the cells are mammalian cells, optionally human cells.

In embodiments, the method further comprises culturing the isolated cell and/or evaluating the isolated cell by flow cytometry, biochemical analysis and/or gene expression analysis.

In embodiments, the method does not comprise attaching a detectable label and/or affinity reagent to the mixture of animal cells.

In embodiments, the detachment force is applied by hydrodynamic force, centrifugal force and/or magnetic force.

In embodiments, the method is carried out in a microfluidic device.

In embodiments, the mixture of animal cells is subjected to the detachment force for 1 to 60 minutes, optionally for 2 to 20 minutes.

The foregoing and other aspects of the present invention will now be described in more detail with respect to other embodiments described herein.

BRIEF DESCRIPTION OF THE DRAWINGS

FIG. 5E. Selective detachment of UD-hiPSC colonies from laminin substrates co-cultured with low density IMR90 fibroblasts.

FIG. 5F. Selective detachment of UD-hiPSC colonies from laminin substrates co-cultured with high density IMR90 cells. Colonies were detached selectively at 85-125 dynes/cm$^2$ shear stress.

FIG. 5G. Selective detachment of UD-hiPSC colony (white arrow) from laminin and fibronectin. Colonies were selectively detached at a shear stress of 85-125 dynes/cm$^2$.

FIG. 12. Relative expression comparison for 84 embryonic stem cell-related genes between device passaged and manual hand-picked hiPSCs at the end of 10 passages using respective methods. The figure depicts a log plot of the relative expression level of each gene (2-ΔCt) between manual (x-axis) and μSHEAR (y-axis). The dashed lines indicate a two-fold change in gene expression threshold.

FIG. 13A. A number of cells fail to become fully reprogrammed hiPSCs. Filled arrow refer to partially reprogrammed cells, whereas white arrows indicate reprogrammed hiPSCs.

FIG. 13B. IMR90-mimicking spread cells and round epithelial-like cells do not exhibit any pluripotency markers.

DETAILED DESCRIPTION OF THE INVENTION

Figure 1A:
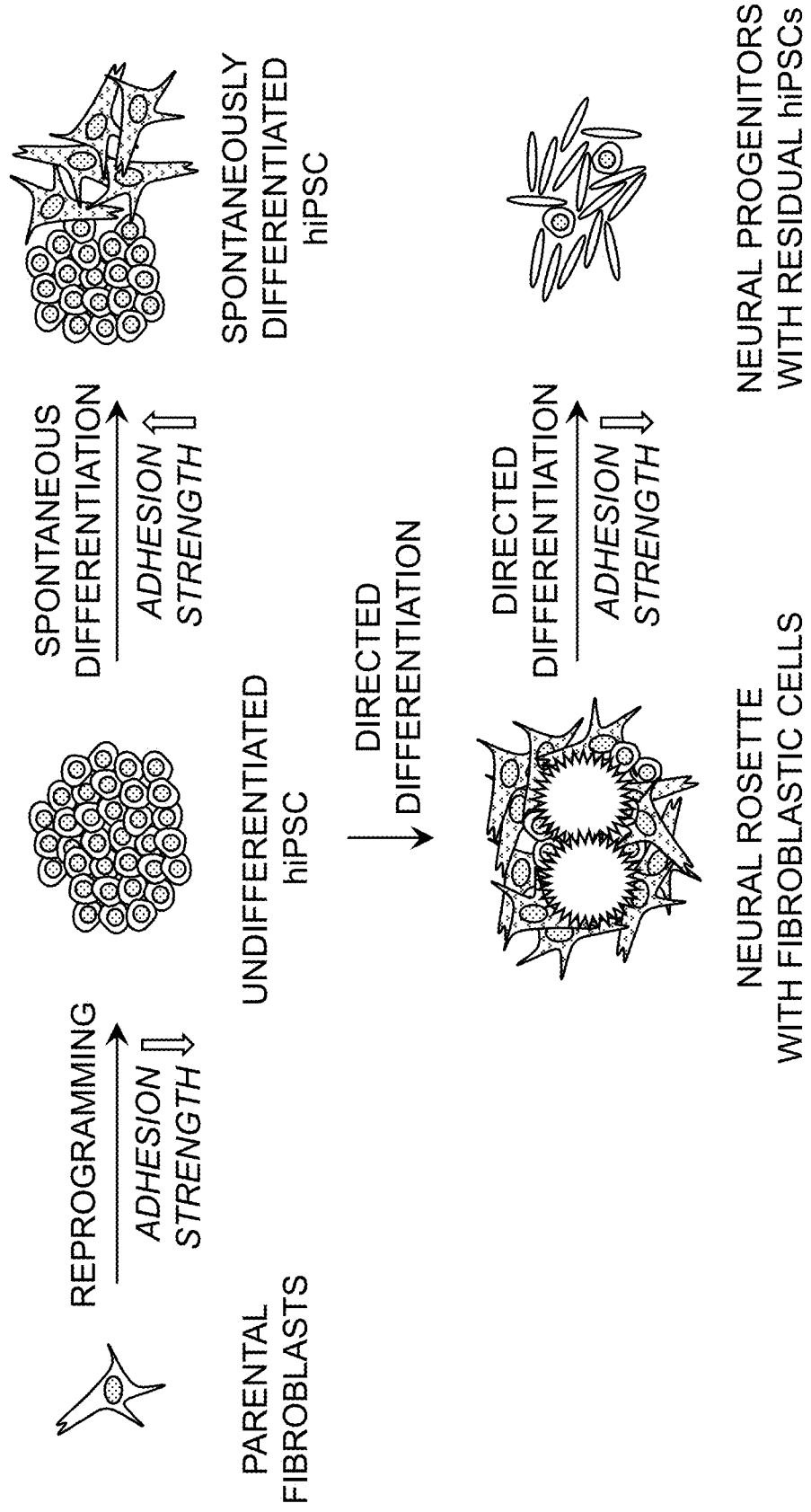
FIG. 1A. Schematic representing changes in adhesive signature of hiPSCs and differentiated cells.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a method comprises steps A, B and C, it is specifically intended that any of A, B or C, or a combination thereof, can be omitted and disclaimed singularly or in any combination. As another example, if the specification states that a cell has particular characteristics, X, Y and Z, it is specifically intended that any of X, Y, Z, or a combination thereof, can be omitted and disclaimed singularly or in any combination.

As used herein, "a," "an" or "the" can mean one or more than one. For example, "a" cell can mean a single cell or a multiplicity of cells.

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim herein is not intended to be interpreted to be equivalent to "comprising."

Cells used in carrying out the present invention are, in general, animal cells including mammalian cells and/or avian cells. Mammalian cells include but are not limited to human, non-human mammal, non-human primate (e.g., monkey, chimpanzee, baboon), dog, cat, mouse, hamster, rat, horse, cow, pig, rabbit, sheep and goat cells. Avian cells include but are not limited to chicken, turkey, duck, geese, quail, and pheasant cells, and cells from birds kept as pets (e.g., parakeets, parrots, macaws, cockatoos, and the like). In particular embodiments, the cell is from a species of laboratory animal. Suitable animal cells include cells from both males and females and animals of all ages including embryonic, infant, neonatal, juvenile, adolescent, adult and geriatric animals.

A "mixture of animal cells" refers to two or more types of animal cells (e.g., 2, 3, 4, 5, 6 or more). According to embodiments of the present invention, the mixture of animal cells is a mixture of adherent animal cells (e.g., in culture).

The term "cell of interest" or "cell type of interest" as used herein refers to a cell or cell type that it is desired to isolate for any reason, but is not indicative of the intended use of the cells. For example, in embodiments, the "cell of interest" to isolate is a contaminating cell (e.g., a stem cell in a culture of progenitor cells intended for transplantation in vivo), which optionally may be discarded "Adhesion strength" as used herein refers to the strength with which a cell is attached (e.g., adhered) to a substrate and is proportional to the shear stress required to separate the cell therefrom. Adhesion strength of a cell to the substrate is a function of a number of properties including the quantity and spatial distribution of integrin receptors and the association of bound integrins to cytoskeletal elements. In embodiments, if one cell has a "higher," "greater" or "increased" (and like terms) adhesion strength as compared with another cell, the adhesion strength is at least about 1.5, 2, 3, 4, 5, 6, 7, 8, 9 or 10-fold higher (e.g., as determined by detachment force). In embodiments, if one cell has a "lower," "lesser" or "reduced" (and like terms) adhesion strength as compared with another cell, the adhesion strength of the first cell is less than about 70%, 60%, 50%, 40%, 30%, 20%, 10% or less than that of the second cell.

The term "substrate" as used herein refers to the surface on which the cells are adhered (e.g., cultured). The substrate can be glass and/or plastic. Examples of suitable substrates include without limitation slides, cover slips, culture dishes, culture bottles, multi-well plates and/or a cassette that fits into a device (e.g., for use with a microfluidic device). The "substrate" can optionally be coated, e.g., with an extracellular matrix protein, including without limitation, laminin, collagen (e.g., collagen IV), vitronectin, fibronectin, entactin, blebbistatin and/or a synthetic polymer coating such as poly[2-methacryloyloxy)ethyl dimethyl-(3-sulfopropyl) ammonium hydroxide] (PMEDSAH). Suitable extracellular matrix formulations are commercially available, such as isvitronectin (R&D Systems), MATRIGEL™ and Laminin-511. As a further option, feeder cells can be grown on the substrate.

The term "detachment force" as used herein refers to a force that is sufficient to detach, remove or separate a cell from the substrate on which it is adhered. The detachment force can be applied by any suitable method including, without limitation, hydrodynamic force, centrifugal force and/or magnetic force. The detachment force can optionally be described in terms of the force that produces a shear stress ($\tau$, force/area) that results in 50% detachment of a plurality of the cells ($\tau_{50}$). In embodiments, the detachment force provides a wall shear stress that is greater than about 10, 20, 30, 40, 50, 60, 70, 80, 90 or 100 dynes/cm$^2$ and/or less than about 40, 50, 60, 70, 80, 90, 100, 105, 110, 115, 120, 125, 130, 140, 150, 160, 170, 180, 190, 200, 225, 250, 300, 350, 400 or 500 dynes/cm$^2$ (including all combinations of lower and higher values as long as the lower limit is less than the upper limit). In embodiments, the detachment force provides a wall shear stress that is from about 10 to about 40, 50, 60, 70, 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 20 to about 40, 50, 60, 70, 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 30 to about 40, 50, 60, 70, 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 40 to about 50, 60, 70, 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 50 to about 60, 70, 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 60 to about 70, 80, 90, 100, 110, 105, 110, 115, 120, 125, 140, 150, 160, 170, 180, 190, 200, 225, 250, 300, 350 or 400 dynes/cm$^2$. In embodiments, the detachment force provides a wall shear stress that is from about 70 to about 80, 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 80 to about 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 80 to about 90, 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 90 to about 100, 105, 110, 115, 120, 125, 130, 140, 150, 160, 170, 180, 190, 200, 225, 250, 300, 350 or 400 dynes/cm$^2$. In embodiments, the detachment force provides a wall shear stress that is from about 100 to about 105, 110, 115, 120, 125, 130, 140, 150, 160, 170, 180, 190, 200, 225, 250, 300, 350 or 400 dynes/cm². In embodiments, the detachment force provides a wall shear stress that is from about 110 to about 120, 125, 130, 140, 150, 160, 170, 180, 190, 200, 225, 250, 300, 350 or 400 dynes/cm². In embodiments, the detachment force provides a wall shear stress that is from about 120 to about 130, 140, 150, 160, 170, 180, 190, 200, 225, 250, 300, 350 or 400 dynes/cm². Further, the detachment force can be applied as a consistent force or can be variable (e.g., within a range).

As used herein, "selectively detach" (and similar terms) refers to preferential detachment of a particular cell type within a mixture of cells from a substrate to which the cell is adhered as compared with at least one other cell type in the mixture of cells adhered to the substrate. In embodiments of the invention, to achieve selective detachment the wall shear stress that results in 50% detachment ($\tau_{50}$) of a cell type of interest is at least about 1.5, 2, 3, 4, 5, 6, 7, 8, 9 or 10-fold lower or higher as compared with the $\tau_{50}$ for at least one other cell type in a mixture of adherent cells. Thus, the cell of interest to be isolated can selectively detach with a higher or lower $\tau_{50}$ than the at least one other cell type in the mixture of cells. In embodiments, at least about 50%, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold or more of the cell type of interest detaches relative to the at least one other cell type. In representative embodiments, the detachment force that "selectively detaches" a particular cell type as compared with at least one other cell type in a mixture of cells adhered to a substrate results in at least about 60%, 70%, 75%, 80%, 85%, 90%, 95%, 96%, 97%, 98%, 99% or more detachment of the first cell type and/or less than about 40%, 30%, 25%, 20%, 15%, 10%, 5%, 4%, 3%, 2%, 1% or less detachment of at least one other cell type in the mixture of cells from the substrate.

As used herein, an "isolated" cell produced by a method of the invention is a cell that has been partially or completely separated, enriched and/or purified from other components (e.g., cells of other types in the mixture of cells) with which it is associated in the mixture of cells (e.g., adherent cells in culture) prior to the use of the methods of the invention. Those skilled in the art will appreciate that an "isolated" plurality or population of cells need not be 100% pure, as long as there is some enrichment or increase in the concentration of the cells of interest as compared with the concentration of the cells in the starting material prior to the use of the methods of the invention. In embodiments, the concentration of the "isolated" cell is increased by at least about 2-fold, 3-fold, 4-fold, 5-fold, 10-fold, 20-fold, 30-fold, 40-fold, 50-fold, 60-fold, 80-fold, 100-fold, 150-fold, 200-fold, 300-fold, 400-fold, 500-fold, 600-fold, 800-fold, 1000-fold or more by the practice of the methods of the invention. In embodiments of the invention, an "isolated" plurality or population of cells is at least about 50%, 60%, 70%, 75%, 80%, 85%, 90%, 95%, 96%, 97%, 98%, 99% or more pure.

"Totipotent" as used herein, refers to a cell that has the capacity to form an entire organism.

"Pluripotent" as used herein refers to a cell that has essentially complete differentiation versatility, e.g., the capacity to grow into essentially any of the animal's cell types (e.g., cells derived from any of the three germs layers: endoderm, mesoderm and ectoderm). A pluripotent cell can be self-renewing, and can remain dormant or quiescent. Unlike a totipotent cell, a pluripotent cell cannot usually form a new blastocyst or blastoderm. A pluripotent cell generally expresses one or more pluripotency markers. Markers of pluripotency are well known in the art and include, without limitation: OCT4 (POU5F1), NANOG, SOX2, SSEA4 (human), SSEA1 (mouse), SSEA3, TRA-1-60, TRA-1-81, alkaline phosphatase, CD30 (Cluster Designation 30), GCTM-2, Genesis, germ cell nuclear factor, telomerase, and Rex-1 (these terms also encompass homologs from other species).

"Multipotent" as used herein refers to a cell that has the capacity to produce any of a subset of cell types of the corresponding animal (e.g., two or more cell types). Unlike a pluripotent cell, a multipotent cell does not have the capacity to form all of the cell types of the corresponding animal. Examples of multipotent cells include lineage committed cells and progenitor cells. Markers associated with particular lineages are well-known in the art and include, without limitation: neural markers (e.g., Nestin, CD133, and/or Musashi-1), hematopoietic markers (e.g., CD34 and/or c-Kit), pancreatic lineage marker (e.g., Nestin and/or vimentin), skeletal muscle markers (e.g., MyoD, Pax7, myogenin, MR4 and/or myosin light chain), cardiac muscle markers (e.g., MyoD, Pax7, and/or myosin heavy chain), and the like.

As used herein, the term "stem cell" includes without limitation: embryonic stem (ES) cells (e.g., derived from the epiblast tissue of the inner cell mass of a blastocyst or earlier morula stage embryo and/or produced by somatic cell nuclear transfer), an induced pluripotent stem (iPS) cell and/or an adult stem cell (e.g., a somatic stem cell and/or a germ line stem cell). In embodiments of the invention, the stem cell is not an adult stem cell. Stem cells are generally characterized by the capacity for self-renewal (the ability to undergo numerous cycles of cell division while maintaining an undifferentiated state) and pluripotency or, in some cases, multipotency. In embodiments of the invention, the stem cell grows in clusters of at least about 2, 4, 6, 8, 10, 20, 40, 60, 80, 100 or more cells (e.g., cells connected by cell-cell adhesions or junctions). In embodiments, the stem cell exhibits apoptosis when not grown or cultured in a cell cluster.

An "undifferentiated stem cell" is generally a pluripotent or multipotent cell. Those skilled in the art will appreciate that ES cells and iPS cells are typically considered pluripotent and express one or more (e.g., 1, 2, 3, 4, 5 or more) pluripotency markers (as that term is understood in the art and as described herein). On the other hand, adult stem cells are typically multipotent, and express one or more markers (e.g., 1, 2, 3, 4, 5 or more) associated with particular lineages. However, some adult stem cells are pluripotent (e.g., stem cells isolated from umbilical cord blood), and can express one or more markers (e.g., 1, 2, 3, 4, 5 or more) associated with pluripotency. Adult stem cells are often referred to by their tissue of origin; mesenchymal stem cells, hematopoietic stem cells, adipocyte-derived stem cells, endothelial stem cells and dental pulp stem cells are non-limiting examples of adult stem cells.

A cell "derived from a stem cell" and similar terms as used herein refers to cells that are produced from stem cells (e.g., undifferentiated stem cells) as a result of differentiation processes. Such cells include without limitation, spontaneously differentiated and directly differentiated stem cells (e.g., lineage committed cells, progenitor cells and/or terminally differentiated cells) and cells in intermediate stages of differentiation. Those skilled in the art will appreciate that the process of differentiation into different cell types from a stem cell is a continuum and cells with intermediate characteristics are often present.

A "spontaneously differentiated stem cell" or "spontaneously differentiated cell" as used herein is a cell derived from an undifferentiated stem cell as a result of a spontaneous (e.g., not directed) differentiation process. Spontaneously differentiated cells are a problematic contaminant of stem cell cultures and pose an obstacle to the culture and use of cultured stem cells. "Spontaneously differentiated stem cells" or "spontaneously differentiated cells" appear to differentiate along random pathways and generally have reduced pluripotency and reduced expression of at least one pluripotency marker as compared with undifferentiated stem cells. In some instances, "spontaneously differentiated stem cells" appear as spread, fibroblast-like cells.

The term "directly differentiated stem cell" or "directly differentiated cell" refers to a cell that has been directed to differentiate along a particular pathway, e.g., by manipulation of culture medium components. Directly differentiated cells include lineage committed cells, progenitor cells, and terminally differentiated cells as well as cells in intermediate stages of differentiation.

The term "lineage committed cell" as used herein indicates a cell that has begun to express markers and/or exhibit morphology, structure, potency (e.g., the ability to differentiate along a particular lineage(s)) and/or other characteristics associated with a particular lineage, but is not yet a "progenitor" cell. Thus, "lineage committed cells" can be viewed as intermediates between stem cells and progenitor cells. Examples of lineage-committed cell include without limitation a neural committed cell (e.g., a neural rosette cell), a hematopoietic committed cell, a skeletal muscle committed cell, a cardiac muscle committed cell, a pancreatic committed cell, and the like. As one illustration, neural rosette cells express the protein marker nestin, but grow as radial clusters, whereas neural progenitor cells grow as individual elongated cells. Thus, neural rosette cells express intermediate characteristics between stem cells and neural progenitor cells.

A "progenitor cell" as used herein refers to a multipotent cell that typically can divide only a limited number of times prior to terminal differentiation. "Progenitor cells" are early descendents of stem cells that typically have a reduced potency and self-replication capacity as compared with stem cells. Nonlimiting examples of progenitor cells include neural progenitor cells, hematopoietic progenitor cells, cardiac muscle progenitor cells, skeletal muscle progenitor cells, pancreatic progenitor cells, and the like.

The term "feeder" cell is well-known in the art and encompasses cells (e.g., fibroblasts, bone marrow stromal cells, and the like) that are cultured with other cells (for example, stem cells) and support the viability and/or growth thereof.

The term "parental somatic" cell or "parental" cell refers to a cell that is reprogrammed to produce an iPS cell. As is known in the art, iPS cells are derived from other, typically non-pluripotent, cells such as a somatic cell (e.g., an adult somatic cell such as a fibroblast) by inducing expression of particular genes and/or introducing particular nucleic acids and/or proteins that result in reprogramming of the cell. iPS cultures are frequently contaminated by non-pluripotent parental cells and/or partially reprogrammed cells. The parental cells can generally be identified by methods known in the art, e.g., morphology (elongated) and/or reduced expression or lack of expression of one or more pluripotency markers (as known in the art and as described herein). Typically, partially reprogrammed cells have taken up some, but not all, of the reprogramming factors (e.g., are transformed with some but not all of the nucleic acids introduced to reprogram the cells). In addition, partially-reprogrammed cells often have a rounded or less-spread morphology as compared with the parental cells, but generally do not express pluripotency markers.

The inventors have made the surprising discovery that the characteristic "adhesive signature" associated with stem cells (e.g., undifferentiated stem cells) and derivatives thereof can be used to selectively detach and isolate these cells from each other and/or from other cells in a mixture of animal cells adhered to a substrate based on differences in adhesion strength for the substrate on which the cells are adhered (e.g., cultured). Thus, the process by which stem cells form derivatives such as committed cells, progenitor cells, and terminally differentiated cells is reflected in changes in the adhesion characteristics (e.g., adhesion strength) of the cells and can be used as the basis for isolating such cells (e.g., to remove contaminating cells). A cell of interest can be isolated from a mixture of cells adhered to a substrate if there is a sufficient difference (higher or lower) in the adhesion strength of the cell of interest to the substrate relative to at least one other cell type (e.g., a contaminating cell type(s)) present in the mixture of cells, such that a detachment force can be applied that will selectively detach the cell of interest from the substrate as compared with the at least one other cell type in the mixture of cells adhered to the substrate.

In embodiments, the cell of interest selectively detaches at a lower detachment force from the substrate as compared with at least one other cell type (e.g., 1, 2, 3, 4, 5 or more other cells types) in the mixture of cells. Nonlimiting examples include the selective detachment of stem cells (e.g., undifferentiated stem cells) from a mixture of cells that comprises fibroblasts, fibroblast-like cells and/or spontaneously differentiated stem cells that have a higher adhesion strength than the stem cells do for the substrate to which the mixture of cells is adhered (e.g., cultured). As another example, iPS cells can be selectively detached and isolated from a mixture of cells adhered to a substrate relative to parental cells and partially reprogrammed cells that have a higher adhesion strength than the iPS cells do for the substrate. Optionally, a higher force can then be applied to detach the at least one other cell type that remains adhered to the substrate.

In embodiments, the cell of interest selectively detaches from the substrate at a higher detachment force as compared with at least one other cell type (e.g., 1, 2, 3, 4, 5 or more other cells types) in the mixture of cells adhered to the substrate. According to this embodiment, the at least one other cell type detaches from the substrate at a lower detachment force. In embodiments, the cell of interest can then be detached from the substrate by the application of a higher detachment force. Alternatively, the cell of interest remains adhered to the substrate and can be cultured and/or can be subject to additional analysis, including for example, biochemical, protein marker, gene expression and/or genetic analysis. A nonlimiting example in which the cell of interest has a higher adhesion strength for the substrate includes the situation in which spontaneous differentiation of stem cells results in contaminating neural progenitor-like cells that have a lower adhesion strength than stem cells (e.g., undifferentiated stem cells) do for the substrate.

In embodiments of the invention, the wall shear stress that results in 50% detachment of the cell type of interest ($\tau_{50}$) is at least about 1.5, 2, 3, 4, 5, 6, 7, 8, 9 or 10-fold higher as compared with the $\tau_{50}$ for at least one other cell type in a mixture of cells. In embodiments, the wall shear stress that results in 50% detachment of the cell type of interest ($\tau_{50}$)

is less than about 70%, 60%, 50%, 40%, 30%, 20%, 10% or less as compared with the $\tau_{50}$ for at least one other cell type in a mixture of cells.

The inventors have discovered that stem cells, and cells derived therefrom, have characteristic adhesive signatures that can be exploited to isolate such cells from each other and from other cells adhered to a substrate (e.g., adherent cells in culture). For example, the methods of the invention find use in methods of isolating stem cells and/or cells derived therefrom, for example, to remove contaminating cells, to passage cells and/or to isolate rare cells, and the like. Accordingly, the methods of the invention can be practiced once (e.g., to identify a cell of interest) or two or more times (e.g., 2, 3, 4, 5, 6, or more times; for example, in passaging cell cultures).

As one aspect, the present invention provides a method of isolating a cell of interest from a mixture of animal cells (e.g., cultured animal cells), wherein the cell of interest is a stem cell or a cell derived therefrom, the method comprising: subjecting a mixture of animal cells adhered to a substrate, the mixture of cells comprising the cell of interest and at least one other cell type (e.g., a cell that is not the cell of interest) to a detachment force that is sufficient to selectively detach the cell of interest from the substrate relative to the at least one other cell type in the mixture of cells, thereby isolating the cell of interest from the mixture of cells.

In representative embodiments, the cell of interest is a stem cell (for example, an undifferentiated stem cell). Stem cells include without limitation ES cells, iPS cells and/or adult stem cells. In embodiments, the stem cell is not an adult stem cell. In embodiments, the stem cell expresses one or more markers associated with pluripotency. In embodiments, the stem cell is pluripotent. In embodiments, the stem cell is multipotent.

The at least one other cell type in the mixture of cells can comprise any other cell type that may be present in the mixture of cells, for example, as a contaminant (e.g., a cell that is not the cell of interest). In embodiments, the at least one other cell type is a feeder cell, a parental somatic cell, a partially reprogrammed cell (e.g., from the process used to reprogram and produce iPS cells), a spontaneously differentiated stem cell and/or a directly differentiated cell (e.g., a lineage committed cell, a progenitor cell, a terminally differentiated cell) and/or any other cell with a sufficient difference in adhesion strength to the substrate so that the cell of interest can be selectively detached and isolated therefrom by an applied detachment force. In representative embodiments, the methods of the invention are used to isolate a stem cell subpopulation from a different subpopulation of stem cells, where the subpopulations of stem cells can be distinguished on the basis of adhesion strength to the substrate.

Thus, the invention finds use in methods of isolating stem cells (for example, an undifferentiated stem cell), e.g., to remove contaminating cells, for cell passaging, and the like. To illustrate, according to embodiments of the invention, the stem cell (for example, an undifferentiated stem cell) is an iPS cell and the at least one other cell type is a parental somatic cell (e.g., a fibroblast) and/or a partially reprogrammed cell.

In other exemplary embodiments, the stem cell (for example, an undifferentiated stem cell) is an ES cell, an iPS cell and/or an adult stem cell and the at least one other cell type is a feeder cell.

In embodiments, the stem cell (for example, an undifferentiated stem cell) is an ES cell, an iPS cell and/or an adult stem cell and the at least one other cell type is a spontaneously differentiated stem cell.

In further representative embodiments, the stem cell (for example, an undifferentiated stem cell) is an ES cell, an iPS cell and/or an adult stem cell and the at least one other cell type is a directly differentiated cell, optionally a lineage committed cell, a progenitor cell and/or a terminally differentiated cell.

As another illustration, the methods of the invention can be used to remove stem cells from populations of cells being prepared for transplantation in vivo (e.g., directly differentiated cells such as progenitor cells and/or terminally differentiated cells). Thus, in embodiments of the invention, the cell of interest is a contaminating cell.

Any detachment force can be used that is sufficient to selectively detach the stem cell (e.g., an undifferentiated stem cell) as compared with the at least one other cell type in a mixture of cells (e.g., a mixture of cultured cells) adherent to a substrate. In representative embodiments, the detachment force provides a wall shear stress in the range of about 70 or 80 to about 150 or 160 dynes/cm$^2$. In embodiments, the detachment force provides a wall shear stress in the range of about 80 to 125 dynes/cm$^2$. Other exemplary detachment forces are described herein.

The present invention can be advantageously practiced with cells that grow in culture as adherent cells. For example, ES cells and iPS cells (e.g., in an undifferentiated state) generally grow as adherent cultures and lose viability when separated into single cells, for example, for passaging and/or isolation. In embodiments, the invention can be practiced to isolate cells that grow in culture as cell clusters. Further, in embodiments of the invention, the cell of interest (e.g., an ES cell or iPS cell) detaches from the substrate as part of a cluster of cells.

Cells isolated by the methods of the invention generally retain their function. For example, in embodiments, a stem cell (e.g., undifferentiated stem cell) isolated according to the methods of the invention maintains expression of one or more (e.g., 1, 2, 3, 4, 5 or more) pluripotency markers. In embodiments, stem cells (e.g., undifferentiated stem cells) isolated according to the methods of the invention retain the ability to produce two or more different cells types. In embodiments, stem cells (e.g., undifferentiated stem cells) isolated according to the methods of the invention are ability to produce endoderm, mesoderm and ectoderm. In further embodiments, stem cells (e.g., undifferentiated stem cells) isolated according to the methods of the invention are pluripotent or multipotent.

The methods of the invention also find use in methods of isolating cells derived from stem cells, for example a stem cell-derived lineage committed cell. Lineage committed cells can be from any cell lineage of interest including, but not limited to, a stem cell-derived neural committed cell, a stem cell-derived hematopoietic committed cell, a stem cell-derived skeletal muscle committed cell, a stem cell-derived cardiac muscle cell, a stem cell-derived pancreatic committed cell, or any other lineage derived from endoderm, mesoderm or ectoderm. Methods of identifying lineage committed cells are known in the art and include, for example, marker expression and/or morphology, structure, potency (e.g., the ability to differentiate along a particular lineage(s)) and/or other characteristics associated with a particular lineage. In embodiments, a neural committed cell expresses the markers nestin and/or Musashi-1. Optionally, the neural committed cell is a neural rosette cell, which generally grow in culture in characteristic radial clusters.

When isolating lineage committed cells (e.g., to remove contaminating cells), the at least one other cell type can be any cell type present in the mixture of cells, for example, is a stem cell (e.g., an undifferentiated stem cell), a feeder cell, a parental somatic cell, a partially reprogrammed cell, a spontaneously differentiated stem cell, another type of lineage committed cell, a progenitor cell, a terminally differentiated cell and/or any other cell with a sufficient difference in adhesion strength to the substrate so that the cell of interest can be selectively detached and isolated therefrom by an applied detachment force.

As one illustrative and nonlimiting example, the method can be used to isolate a neural committed cell (e.g., a neural rosette cell) from a mixture of cells adhered to a substrate. Typically, at least some of the stem cells (e.g., undifferentiated stem cells) present in the mixture of cells will be isolated along with the neural committed cells. In some embodiments, the neural committed cells (along with any stem cells present) can be cultured, and optionally the medium and/or other culture conditions can be manipulated to differentiate the neural committed cells to neural progenitor cells. As a further option, the neural progenitor cells can then be isolated away from any stem cells (e.g., undifferentiated stem cells) present in the culture using a method according to the present invention.

As another example, cultures of lineage committed cells (e.g., neural committed cells) can be contaminated with spread, fibroblast-like cells. These cells can be distinguished on the basis of adhesion strength to the substrate and isolated according to the methods of the invention. For example, neural rosette cells can be selectively detached and isolated away from the fibroblast-like cells by applying a relatively low detachment force (as described herein).

Any detachment force can be used that is sufficient to selectively detach the lineage committed cell as compared with the at least one other cell type in a mixture of cells adhered to a substrate. In representative embodiments, the detachment force provides a wall shear stress in the range of about 20 to 160 dynes/cm$^2$. In embodiments, the detachment force provides a wall shear stress in the range of about 70 or 80 to about 150 or 160 dynes/cm$^2$. In embodiments, the detachment force provides a wall shear stress in the range of about 80 to 125 dynes/cm$^2$. Other exemplary detachment forces are described herein.

Methods of isolating stem cell-derived progenitor cells from a mixture of adherent animal cells (e.g., cultured animal cells) are also contemplated by the present invention. The stem cell derived progenitor cell can be from any cell lineage known in the art, including without limitation a stem cell-derived neural progenitor cell, a hematopoietic progenitor cell, a cardiac muscle progenitor cells, a skeletal muscle progenitor cell, a pancreatic progenitor cell or any other lineage derived from endoderm, mesoderm or ectoderm. Methods of identifying progenitor cells are known in the art and include, for example, for example, marker expression and/or morphology, structure, potency (e.g., the ability to differentiate along a particular lineage) and/or other characteristics associated with a particular progenitor cell. For example, a stem cell-derived neural progenitor cell can optionally express the marker nestin and differentiate into neural cells expressing Tuj-1 and/or MAP2. In embodiments, the stem cell-derived progenitor cells isolated according to the methods of the invention retain their function, for example, are multipotent (e.g., are able to differentiate into two or more lineage specific cell types).

In methods of practicing the invention to isolate a stem-cell-derived progenitor cell, the at least one other cell type can be any other cell type present in the mixture of cells. For example, the at least one other cell type can be a stem cell (e.g., an undifferentiated stem cell), a feeder cell, a parental somatic cell, a partially reprogrammed cell, a spontaneously differentiated stem cell, a lineage committed cell, another progenitor cell type, a terminally differentiated cell and/or any other cell with a sufficient difference in adhesion strength to the substrate so that the cell of interest can be selectively detached and isolated therefrom by an applied detachment force.

As a representative example, it can be advantageous to isolate progenitor cells away from residual stem cells (e.g., undifferentiated stem cells) in the mixture of cells. There is a concern in the art that residual stem cells can form teratoma if transplanted into a subject in vivo. Accordingly, the invention can be practiced to isolate progenitor cells and decrease the population of contaminating stem cells to reduce the risk of teratoma formation for progenitor cell populations that may be used for transplantation.

Any detachment force can be used that is sufficient to selectively detach the progenitor cell as compared with the at least one other cell type in a mixture of cells adhered to a substrate. In representative embodiments, the detachment force provides a wall shear stress in the range of about 10 to 120 or 130 dynes/cm$^2$. In embodiments, the detachment force provides a wall shear stress in the range of about 20 to 70 or 80 dynes/cm$^2$. In still further embodiments, the detachment force provides a wall shear stress in the range of about 20 to 40, 50 or 60 dynes/cm$^2$. Other exemplary detachment forces are described herein.

The present invention can also be practiced to isolate terminally differentiated cells from mixtures of cells (e.g., in adherent cell cultures). The terminally differentiated cell can be any differentiated cell known in the art, e.g., a cardiac muscle cell, a skeletal muscle cell, a smooth muscle cell, a blood cell, a hepatocyte, a skin cell, an endothelial cell, a pancreatic cell, a hepatocyte, a neural cell, or any other cell derived from endoderm, mesoderm or ectoderm. Methods of identifying terminally differentiated cells are known in the art and, include, for example, marker expression, morphology, functional and/or structural characteristics. For example, cardiomyocytes generally express MyoD, Pax7, and/or myosin heavy chain.

When isolating terminally differentiated cells according to the methods of the invention, the at least one other cell type can be any cell that may be present in the mixture of cells (e.g., a contaminating cell). In representative embodiments, the at least one other cell type is a stem cell (e.g., an undifferentiated stem cell), a feeder cell, a parental somatic cell, a partially reprogrammed cell, a spontaneously differentiated stem cell, a lineage committed cell, a progenitor cell, another terminally differentiated cell type and/or any other cell with a sufficient difference in adhesion strength to the substrate so that the cell of interest can be selectively detached and isolated therefrom by an applied detachment force.

Any detachment force can be used that is sufficient to selectively detach the terminally differentiated cell as compared with the at least one other cell type present in a mixture of cells adhered to a substrate. In representative embodiments, the detachment force provides a wall shear stress in the range of about 20 to 120 or 130 dynes/cm$^2$. In embodiments, the detachment force provides a wall shear stress in the range of about 70 to 120 or 130 dynes/cm$^2$. In embodiments, the detachment force provides a wall shear stress in the range of about 20 to 70 or 80 dynes/cm$^2$. In still further embodiments, the detachment force provides a wall shear stress in the range of about 20 to 40 or 50 dynes/cm$^2$. Other exemplary detachment forces are described herein.

In practicing the present invention, any two adherent cells (e.g., in culture) with sufficiently different adhesion strength to the substrate can be separated. In embodiments of the invention, the cell of interest detaches at a lower detachment force as compared with the at least one other cell type. For example, a stem cell (e.g., an undifferentiated stem cell) can be isolated from contaminating fibroblasts or fibroblast-like cells and spontaneously differentiated cells because the stem cell can be selectively detached at a lower detachment force.

Alternatively, the cell of interest can detach at a higher detachment force as compared with the at least one other cell type. To illustrate, at least some neural progenitor cells have a lower adhesion strength relative to stem cells (e.g., undifferentiated) or neural committed cells. Thus, according to some embodiments one can isolate stem cells and/or neural committed cells from neural progenitor cells by first detaching the neural progenitor cells at a lower detachment force. The stem cells and/or neural committed cells can then be cultured, subjected to analysis and/or can be detached by application of a higher detachment force.

Cells isolated according to the methods of the invention are generally viable and/or retain the ability to divide and produce progeny cells. For example, in embodiments of the invention, at least about 50%, 60%, 70%, 80%, 90%, 95%, 96%. 97%, 98%, 99% or more of the cells are viable and/or retain the ability to divide and produce progeny cells.

Further, in embodiments of the invention, the cells are isolated with high efficiency and/or to a high level of purity. In embodiments of the invention, at least about 50%, 60%, 70%, 80%, 90%, 95%, 96%. 97%, 98%, 99% or more of the cells of interest in the mixture of animal cells adhered to the substrate are isolated. In embodiments, a plurality of the cells of interest are isolated with at least about 50%, 60%, 70%, 80%, 90%, 95%, 96%. 97%, 98%, 99% or more purity.

In addition, the isolation methods provided herein have been found to be quite robust and can isolate cells present at a wide range of starting concentrations in a mixture of cells. For example, in embodiments of the invention, the cell of interest constitutes less than about 50%, 40%, 30%, 25%, 20%, 15%, 10%, 5%, 4%, 3%, 2% or 1% or less of the cells in the mixture of animal cells. In embodiments, the cell of interest constitutes at least about 50%, 60% 70%, 80%, 90%, 95%, 96%. 97%, 98%, 99% or more of the cells in the mixture of animal cells.

Cells isolated according to the methods of the invention can be used for any purpose, e.g., further culture, transplantation and/or evaluation (for example, by flow cytometry, biochemical analysis, gene expression analysis and/or any other suitable analysis).

The detachment force can be applied to the mixture of cells using any suitable method. As nonlimiting examples, the detachment force can be applied by hydrodynamic force, centrifugal force and/or magnetic force. In embodiments, the method of applying the detachment force does not involve labeling the cells with a detectable label and/or affinity reagent.

The detachment force can be applied for any suitable period of time to achieve the desired level of detachment and isolation. In embodiments, the detachment force is applied for at least about 0.5, 1, 2, 3, 4, 5, 6, 7, 8, 9, 10, 12, 14, 16, 18, 20 minutes and/or less than about 5, 6, 7, 8, 9, 10, 12, 14, 16, 18, 20, 25, 30, 35, 40, 45, 50, 55, 60, 75, 90, 105 or 120 minutes (including all combinations of lower and upper values as long as the lower limit is less than the upper limit).

In representative embodiments, the time period is from about 2 to 20 minutes. In embodiments, the time period is from about 5 to 15 minutes.

In representative embodiments, the method is carried out in a microfluidic device or a spinning disk device.

The invention further provides an isolated cell and isolated populations and cultures of cells produced by the methods of the invention.

The present invention is more particularly described in the following examples that are intended as illustrative only since numerous modifications and variations therein will be apparent to those skilled in the art.

Example 1

Materials and Methods

Cell Culture.

The hiPSCs (IMR90) were derived and validated by ArunA Biomedical, Inc. using the viPS™ Vector Kit (Thermo Scientific Open Biosystems) composed of six lentiviral vectors encoding OCT4, NANOG, SOX2, LIN28, KLF4 and c-MYC driven by the EF1alpha promoter. Briefly, IMR90 human fetal lung fibroblasts (female, ATCC) were transduced (MOI 10 each vector) for reprogramming as per manufacturer's protocol. Transduced fibroblasts were seeded onto inactivated mouse embryonic fibroblasts (MEFs) to form colonies and emerging hiPSC colonies were manually passaged by mechanical dissociation on MEFs. hiPSCs demonstrated well-defined borders, high nuclear to cytoplasmic ratio, prominent nucleoli, alkaline phosphatase activity, positive expression of cell surface marker SSEA4, embryoid body formation and teratoma formation. To transition hiPSCs to a feeder-free culture system, colonies were manually passaged by mechanical dissociation onto Matrigel™ (1:100 dilution; BD Biosciences) in mTeSR®1 medium (STEMCELL Technologies). hiPSCs used in the study were between passage 26-48, routinely cultured as feeder-free undifferentiated colonies (UD-hiPSC) in mTeSR®1 medium on Matrigel™, enzymatically passaged with dispase (1 mg/mL), followed by scraping. Human dermal fibroblast-derived hiPSC (11b, healthy male donor) were obtained from Harvard Stem Cell Institute and cultured as above. hESCs used in the study were at passage 35 (H1, Wicell), passage 54 (H7, Wicell) and cultured in mTeSR®1 medium on Matrigel™ as described before. IMR90 human fetal lung fibroblasts (passage 15-20), human dermal fibroblasts (primary adult skin, Cell Applications) and MEFs (primary isolated, passage 2) were cultured in Dulbecco's Modified Eagle's Medium with 1% L-glutamine, 1% non-essential amino acids, 10% Fetal Bovine Serum (FBS), and 1% penicillin/streptomycin. Immunostaining and flow cytometer measurements were performed using antibodies listed in Table 1.

TABLE 1

| Marker | Primary Antibody | Secondary Antibody |
|---|---|---|
| Octamer-Binding Transcription Factor ¾ (Oct3/4) | Rabbit Oct-3/4 (H-134): sc-9081(Santa Cruz Biotechnology, Inc.) | Alexa Fluor ® 546-IgG (Invitrogen) |
| Stage-Specific Embryonic Antigen-4 (SSEA4) | Mouse MC-813-70 (SSEA-4) (Developmental Studies Hybridoma Bank) | Alexa Fluor ® 488-IgG (Invitrogen) |
| Integrin β1 | beta1 Mouse Monoclonal Antibody (Part No. MAB1951Z-20, Millipore) | Alexa Fluor ® 488-IgG (Invitrogen) |

TABLE 1-continued

| Marker | Primary Antibody | Secondary Antibody |
|---|---|---|
| Integrin α5 | alpha5 Mouse Monoclonal Antibody (Part No. MAB 1956Z-20, Millipore) | Alexa Fluor ® 488-IgG (Invitrogen) |
| Integrin α6 | alpha6 Rat Monoclonal Antibody (Part No. MAB1378-20, Millipore) | Alexa Fluor ® 488-IgG (Invitrogen) |
| Integrin β1 (Blocking) | Rat integrin beta-1 (AIIB2, Developmental Studies Hybridoma Bank) | N/A |
| TRA-1-81 | Ms mAB TRA-1-81 ab16289 (Abcam) | Alexa Fluor ® 488-IgG (Invitrogen) Or Alexa Fluor ® 546-IgG (Invitrogen) |
| TRA-1-60 | Ms mAB TRA-1-60 ab16288 (Abcam) | Alexa Fluor ® 488-IgG (Invitrogen) or Alexa Fluor ® 546-IgG (Invitrogen) |
| Hoechst 33258 | Hoechst 33258 (Sigma-861405 Sigma-Aldrich) | N/A |
| Paired Box Protein 6 (PAX6) | ab5790 (Abcam) | Alexa Fluor ® 488-IgG (Invitrogen) |
| α-Fetoprotein | A0008 (Dako) | Alexa Fluor ® 488-IgG (Invitrogen) |
| α-Smooth Muscle Actin (α-SMA) | Ab5694 (Abcam) | Alexa Fluor ® 488-IgG (Invitrogen) |
| STAINALIVE Mouse Anit-Human TRA-1-60 | (Stemgent ®) | DyLight ™ 488 Conjugated |

Neural Rosette, Progenitor Cell and Differentiated Neuronal Cell Derivation.

Neural rosettes and subsequent neural progenitor cells and differentiated neuronal cells were derived from feeder-free, pluripotent colonies of hiPSC (passage 40 or 52), based on methods previously described using hESC53. Briefly, hiPSC were enzymatically passaged 1:2 with dispase (1 mg/mL) followed by cell scraping onto BD Matrigel™ (diluted 1:100; BD Biosciences) in mTeSR®1 Medium (STEMCELL Technologies). Medium was changed every other day for 4 days. On day 5, medium was switched to neural derivation medium (DMEM/F-12 supplemented with N-2 (Life Technologies), 4 ng/mL Fibroblast Growth Factor 2 (FGF2; R&D Systems), 2 mM L-glutamine (Life Technologies) and 50 U/mL, 50 μg/mL Penicillin-Streptomycin (Life Technologies)) and changed every other day. After 1 week in neural derivation medium, neural rosettes were manually isolated and then propagated on BD Matrigel™ (diluted 1:200) in neural proliferation medium (Neurobasal® Medium supplemented with B-27® (Life Technologies), 20 ng/mL FGF2, 10 ng/mL Leukemia Inhibitory Factor (LIF, Millipore), 2 mM L-glutamine (Life Technologies) and 50 U/mL, 50 μg/mL Penicillin-Streptomycin (Life Technologies)), with medium changed every other day. After 4 weeks of differentiation, neural progenitor cells were manually isolated from neural rosette cultures and propagated as an adherent monolayer on BD Matrigel™ in neural proliferation medium. After several manual passages with a cell scraper, confluent cultures of hiPSC-derived neural progenitor cells on BD Matrigel™ (diluted 1:200) were differentiated for 2 weeks to mature, β-III tubulin (TUJ 1)/MAP2-positive neuronal cells by removing FGF2 from the neural proliferation medium and changing medium every 2-3 days.

Design and Fabrication of Poly(Dimethylsiloxane) (PDMS) Micropatterned Arrays.

PDMS micropattern arrays with 10 μm, 20 μm, 56 μm, and 170 μm were fabricated from silicon array masters (Gallant et al., Mol. Biol. Cell 16:4329-4340 (2005); Dumbauld et al., J. Cell Physiol. 223:746-456 (2010); Fu et al., Nat. Methods 7:733-736 (2010)). Microcontact printing on glass coverslips coated with Ti (100 Å) followed by Au (100 Å) was achieved using hexadecanethiol/(HO (CH$_2$CH$_2$O)$_3$—(CH$_2$)$_{11}$SH) chemistry (Gallant et al., Mol. Biol. Cell 16:4329-4340 (2005); Dumbauld et al., Biol. Cell 102:203-213 (2010)). Coverslips were incubated with extracellular matrix (ECM) proteins (fibronectin or laminin, 50 μg/ml in PBS with calcium/magnesium, Invitrogen)(Gallant et al., Mol. Biol. Cell 16:4329-4340 (2005); Dumbauld et al., Biol. Cell 102:203-213 (2010)). After blocking with 1% denatured bovine serum albumin (Sigma) for 30 minutes and eluting proteins for two hours in phosphate-buffered saline (PBS), single cell suspensions of IMR90 cells or hiPS were seeded in mTeSR1 medium with ROCK-inhibitors Y27362 (10 μM, Calbiochem) or Thiazovivin (2 μM, Stemgent®). Briefly, hiPS cells were treated with 0.05% trypsin for 1 minute and scraped as colonies. Cells were then prepared as single cells in mTeSR® 1 with Y27362-ROCK inhibitor and seeded as 100,000 cells/ml on the micro-patterned stamps overnight.

Cell Adhesive Force Measurements.

Cell adhesion strength was measured using a spinning disk system (Garcia et al., J. Biol. Chem. 273:10988-10993 (1998); Gallant et al., Mol. Biol. Cell 16:4329-4340 (2005)). Coverslips with adherent cells cultured overnight were spun in PBS with 2 mM dextrose for 5 minutes at a constant speed in a custom-built device in compliance with American Society for Testing and Materials (ASTM standard F2664-11). The applied shear stress (τ) is given by the formula $\tau=0.8r(\rho\mu\omega^3)^{1/2}$, where r is the radial position, p and μ are the fluid density and viscosity, respectively, and ω is the spinning speed. After spinning, cells were fixed in 3.7% formaldehyde, permeabilized in 0.1% Triton™ X-100, stained with DAPI (Invitrogen), and counted at specific radial positions using a 10× objective lens in a Nikon TE300 microscope equipped with a Ludl motorized stage, Spot-RT camera, and Image-Pro® analysis system. Sixty-one fields were analyzed and cell cluster counts were normalized to the number of cell cluster counts at the center of the disk, where the applied force is zero. The fraction of adherent cell cluster (f) was then fit to a sigmoid curve $f=1/(1+\exp[b(\tau-\tau_{50})])$, where $\tau_{50}$ is the shear stress for 50% detachment and b is the inflection slope. $\tau_{50}$ represent the mean adhesion strength for a population of cells. The adhesion strength response was analyzed on micropatterned islands coated with saturating fibronectin or laminin concentrations (50 μg/ml) or Matrigel™ (1:80 dilutions).

Focal Adhesion Assembly.

Immunofluorescence staining of focal adhesion proteins was performed as previously described (Gallant et al., Mol. Biol. Cell 16:4329-4340 (2005)). Briefly, cells were pre-washed with ice-cold PBS with calcium and magnesium, incubated in ice-cold cytoskeleton stabilization buffer (50 mM NaCl, 150 mM sucrose, 3 mM MgCl$_2$, 1 μg ml$^{-1}$ aprotinin, 1 μg ml$^{-1}$ leupeptin, 1 μg ml$^{-1}$ pepstatin and 1 mM phenylmethylsulfonyl fluoride) for 1 minute, followed by two incubations (1 minute each) in cytoskeleton buffer supplemented with 0.5% Triton™ X-100 (Roche). Detergent-extracted cells were fixed in 4% paraformaldehyde in PBS, washed with PBS, incubated with a primary antibody against vinculin (Upstate) or talin (Sigma) and detected with Alexa Fluor® 488-conjugated antibodies (Invitrogen).

Fabrication of Microfluidic Devices.

PDMS (Sylgard 184, Dow Corning, MI) microfluidic devices were fabricated as reported earlier using a negative photoresist (SU-8 2050, 50 m thickness MicroChem, Newton, Mass.) and UV light photolithography (McDonald et al., *Electrophoresis* 21:27-40 (2000)). Patterned negative molds were then exposed to vapor-phase tridecafluoro-1,1,2,2-tetrahydrooctyl-1-trichlorosilane (United Chemical Technologies, Bristol, Pa.) in a vacuum desiccator to prevent adhesion of PDMS. A 5 mm-thick layer of degassed PDMS mixture (10:1 ratio) was cast onto the mold and cured at 70° C. for 2 hours. Cast PDMS devices were peeled-off and then punctured for inlet-outlet holes and bonded to glass coverslips by exposure to oxygen plasma for 20 seconds.

Micro Stem Cell High-Efficiency Adhesion-Based Recovery (μSHEAR)-Based Isolation.

Prior to coating with ECM proteins, the microfluidic channels and tubes were sterilized with 70% ethanol and rinsed thoroughly with PBS. ECM proteins at 50 μg/ml (fibronectin or laminin) or 1:80 Matrigel™ were flowed through sterile devices and incubated for 1 hour at room temperature. Small colonies of pluripotent stem cells and single cell suspensions of fibroblasts were premixed and pipetted into the inlet reservoir using a 200 μl pipette tip and were cultured in the device for 24 hours at 37° C. with 5% $CO_2$ before detachment experiments. The device inlet was connected to a syringe pump using polyethylene tubing (Catalog# BB31695-PE/4, Scientific Commodities Inc.) and outlet tubes emptied into collecting tubes. PBS was flowed at predetermined flow rates through the device to match up the desirable fluid shear stress, and cell detachment was monitored though a Nikon TE microscope. For this microfluidic flow configuration, the applied wall shear stress (z) is defined by the formula $\tau = 12(\mu Q/wh^2)$, where w and h are the width and height of the channel, respectively, is the fluid viscosity, and Q is the fluid flow rate (Lu et al., *Anal. Chem.* 76:5257-5264 (2004)). Cell/colonies were plated on Matrigel™-coated tissue culture plates in 10 μM ROCK inhibitor Y27362 (or 2 μM Thiazovivin) containing mTeSR®1 media. For flow cytometry studies to determine purification efficiency, collected colonies or cells were immediately resuspended in a suspension of Stemgent® StainAlive™-DyLight™-488 mouse anti-human TRA-1-60 antibody, and CMPTX-Cell Tracker Red dye, stained for 45 minutes, washed and analyzed using Accuri flow cytometer (BD Biosciences).

Pluripotent Stem Cell Characterization.

Karyotype analysis was performed on 20 metaphase spreads for each sample by CellLine Genetics (Madison, Wis.). To determine population doubling time and survival, detached colonies from μSHEAR were dissociated into single cells and plated in Matrigel™-coated 12-well plates. At predetermined times, wells were washed and cells were counted. Embryoid bodies (EBs) from detached and expanded hiPSCs were formed using ultra-high throughput forced aggregation method (Bratt-Leal et al., *Biomaterials* 32:48-56 (2011) and after 24 hours, cell aggregates were transferred to a suspension culture on a rotary orbital shaker (65 RPM). Differentiation was followed by plating EBs in cell chambers (BD Falcon) and after 21 days differentiated cells were fixed with 4% paraformaldehyde, permeabilized with 0.05% Triton™-X100, and stained with antibodies against α-fetoprotein, α-smooth muscle actin, and PAX6.

Gene Expression Analysis.

RNA was isolated from induced pluripotent stem cells (iPSCs) using QIAshredder™ and RNeasy® Mini kits (Qiagen) according to manufacturer's protocols. First-strand cDNA synthesis was performed using the RT2 First Strand Kit (SABiosciences) followed by real-time PCR using the Human Embryonic Stem Cells PCR array (SABiosciences) according to manufacturer's recommended protocols and using a BioRad MyCycler™ and BioRad MyiQ™ real-time thermal cycler, respectively. Individual Ct values were first internally normalized to GAPDH and subsequently analyzed with Genesis software (Graz University of Technology) including log 2 transformation and Hierarchical clustering.

Statistics.

For integrin profiling, one-way analysis of variance (ANOVA) was performed followed by Bonferroni correction using OriginPro 8.5.1. Paired, two-tailed, Student's t-test was performed to determine the significance of differences between 2 groups in adhesion blocking, adhesion strength, and μSHEAR assays. In all tests, p<0.05 was regarded as statistically significant. All experiments were repeated in triplicates unless otherwise stated and bar graph represents mean 4 SD.

Example 2

Changes in 'Adhesive Signature' with Induced Reprogramming and Differentiation

During the process of reprogramming, hiPSCs derived from fibroblasts and other parental cells undergo significant changes in cell morphology through a mesenchymal-to-epithelial transition resulting in a phenotype that is indicative of the pluripotent state (Samavarchi-Tehrani et al., *Cell Stem Cell* 7:64-77 (2010)). Similar to hESCs, hiPSCs grow in compact, epithelial colonies with ultrastructural characteristics analogous to the epiblast epithelium of the mammalian embryo (Chen et al., *Cell Stem Cell* 7:240-248 (2010)). We designed a study to evaluate whether feeder-free UD-hiPSCs exhibit adhesive force characteristics or an "adhesive signature" distinct from the parental human fibroblast cells (IMR90), SD-hiPSCs, and neural progenitors obtained via directed differentiation (FIG. 1A).

Figure 1B:
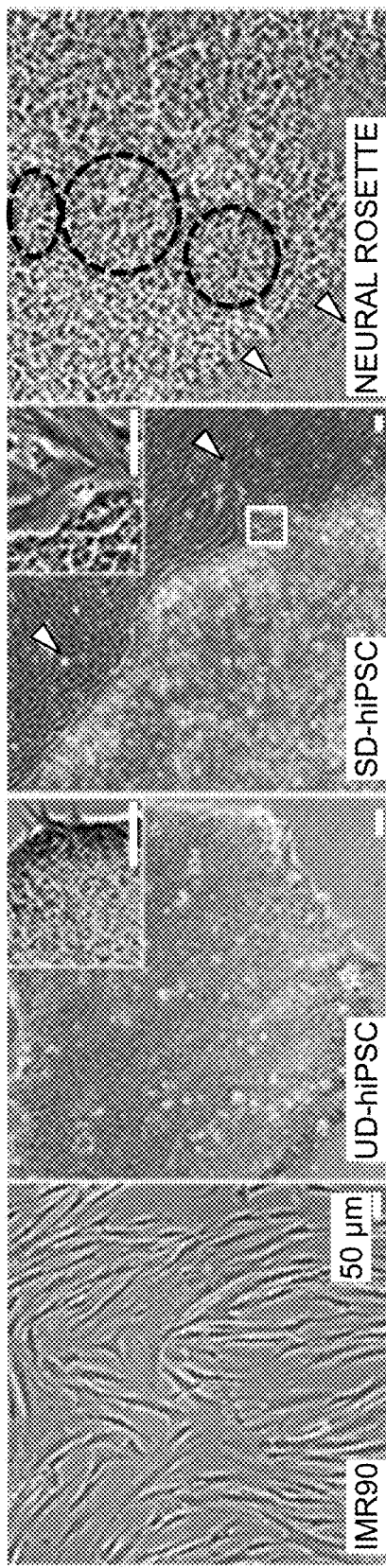
FIG. 1B. Morphological changes in IMR90-fibroblasts, reprogrammed UD-hiPSCs, SD-hiPSCs, and neural rosettes (directed differentiation). Arrowheads indicate spontaneously differentiated cells and dashed circles point out rosettes.
Figure 1C:
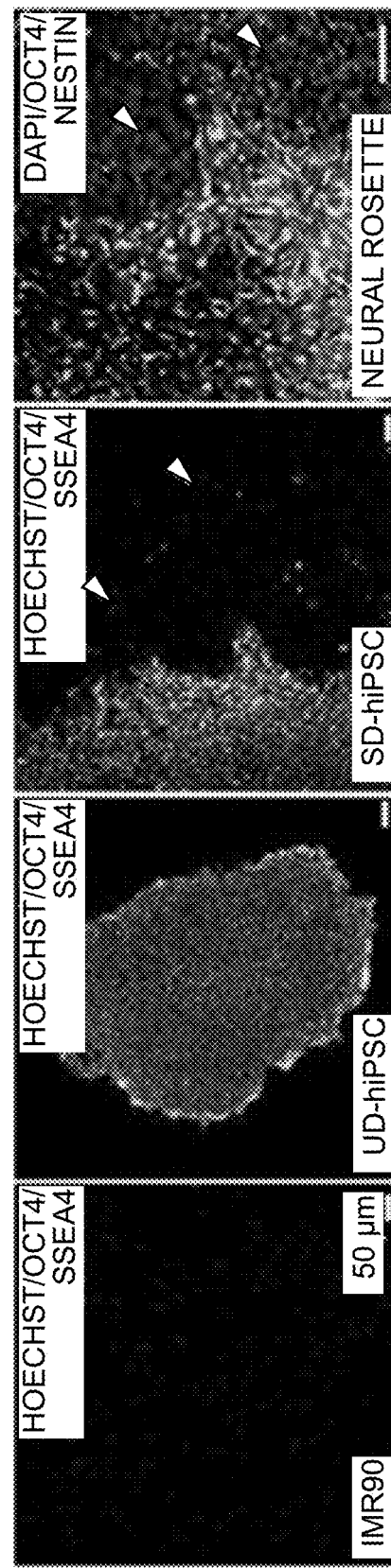
FIG. 1C. Expression of pluripotency markers SSEA4 and OCT4 in IMR90, UD-hiPSCs, and SDhiPSCs. Neural marker Nestin expressed by rosettes and neural committed cells, but absent in contaminating cells.
Figure 1D:
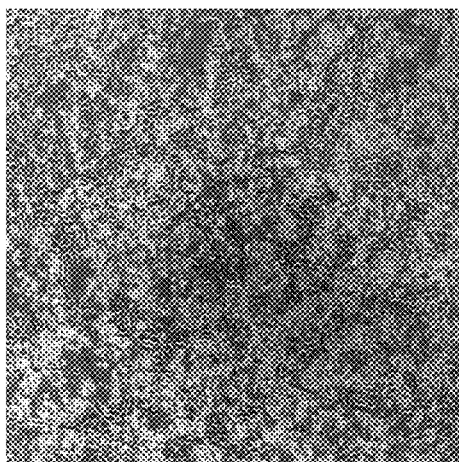
FIG. 1D. Morphology of FACS-sorted >97% TRA-1-60+ hiPSCs seeded on Matrigel™-coated tissue culture surfaces. The single cell dissociation results in loss of colonies and significant cell death.
Figure 1D:
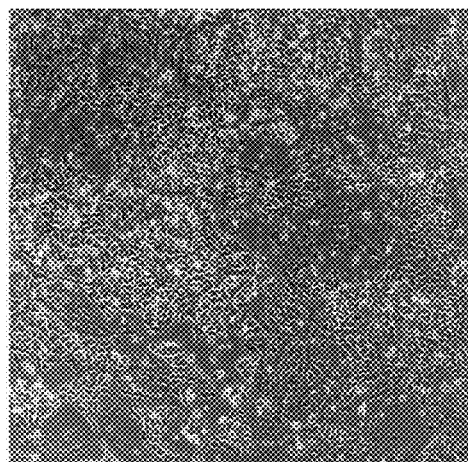
Figure 1E:
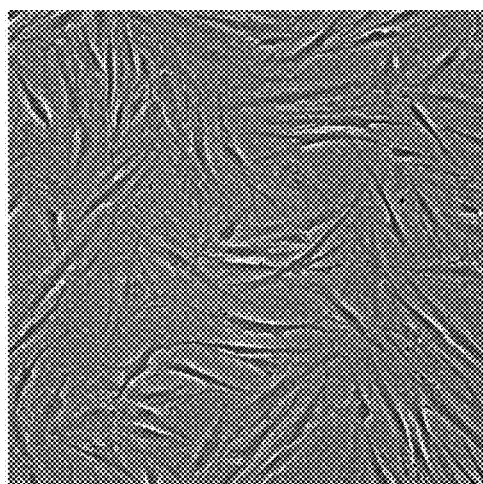
FIG. 1E. Morphology of spread human dermal fibroblasts and epithelial-like fibroblast-derived hiPSCs.
Figure 1E:
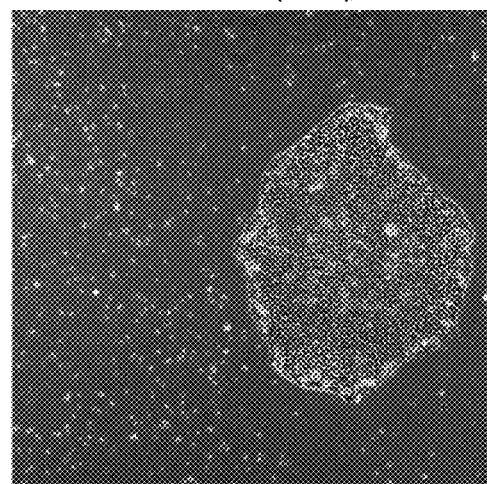
Figure 1F:
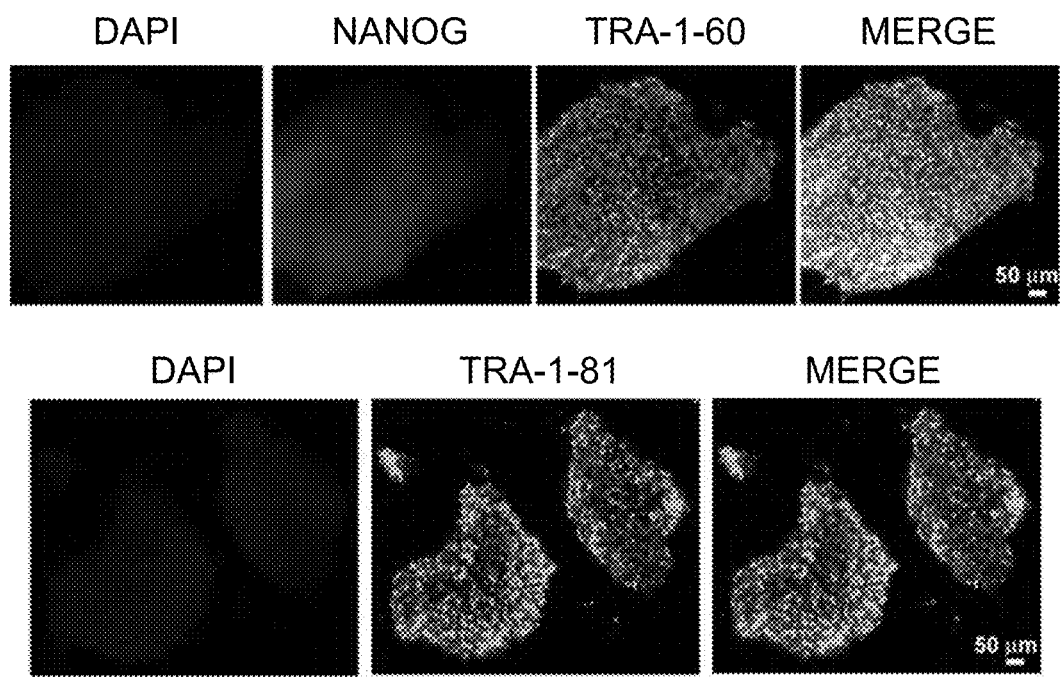
FIG. 1F. Pluripotency markers TRA-1-60 and NANOG (upper panels) and TRA-1-81 (lower panel) expressed by reprogrammed IMR90-derived hiPSCs.

The adhesive strength of a cell to its surrounding matrix is a complex function of the quantity and spatial distribution of integrin receptors ligated to extracellular matrix molecules as well as the association of bound integrins to cytoskeletal elements (Garcia et al., *J. Biol. Chem.* 273: 10988-10993 (1998); Geiger & Bershadsky, *Curr. Opin. Cell Biol.* 13:584-492 (2001); Gallant et al., *Mol. Biol. Cell* 16:4329-4340 (2005)). The composite of these adhesive characteristics, which constitutes the adhesive signature of a cell, could be used to define the phenotype of cells in different states. Human fibroblasts, including the IMR90 line and primary dermal fibroblasts, represent one of the most common somatic cell sources (Yu et al., *Science* 1917-1920 (2007); Lister et al., *Nature* 462:315-322 (2009)) for reprogramming. IMR90 and dermal fibroblasts exhibited an elongated morphology without direct cell-cell adhesions and defined cell polarity as compared to the reprogrammed state of UD-hiPSCs which existed as tightly packed epithelial colonies (FIGS. 1B and 1E). Unlike UD-hiPSCs, colonies with partial spontaneous differentiation exhibited regions with mesenchymal-like and epithelial-like morphologies (FIG. 1B). IMR90 parental cells were further characterized by the absence of pluripotency markers OCT4 and SSEA4, which, among others, defined the undifferentiated state of hiPSCs (FIG. 1C). The derived hiPSCs were positive for OCT4, SSEA4, TRA-1-60, NANOG, and TRA-1-81 (FIGS. 1C and 1F) and thus represented fully reprogrammed cells (Chan et al., *Nat. Biotechnol.* 27:1033-1037 (2009)). As spontaneous differentiation occurred, cells transitioning from epithelial UD-hiPSC to mesenchymal SD-hiPSCs lost pluripotency as indicated by significantly decreased or the complete absence of OCT4 and SSEA4 expression (FIG.

Figure 1G:
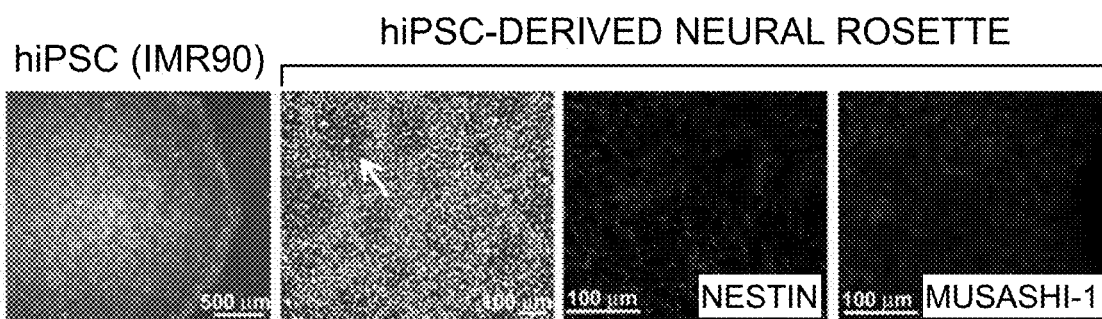
FIG. 1G. Expression markers and morphology of hiPSC-derived neural rosettes.
Figure 1H:
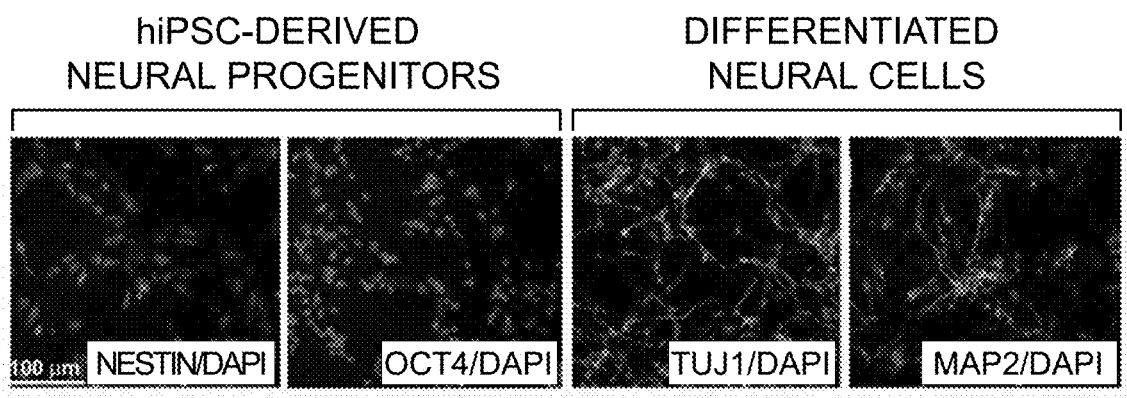
FIG. 1H. Expression markers and morphology of hiPSC-derived neural progenitors and their differentiation to neural lineages (Tuj 1 and MAP2).

1C). Because of the significant morphological changes resulting from reprogramming, we evaluated whether induced pluripotent cells would exhibit significant changes in the adhesive characteristics when compared to the parental somatic cells. Furthermore, human neural rosettes, which are a distinct group of early-stage multi-potent neural stem cells obtained via directed differentiation of hiPSCs33 exhibited a radial pattern of epithelial cell-like morphology (FIG. 1B), distinct from round UD-hiPSCs and the surrounding spread fibroblast-like cells. Rosettes, expressing Nestin (FIG. 1C) and Musashi-1 (FIG. 1G), were manually isolated and further differentiated to neural progenitors with elongated epithelial morphology and loss of OCT-4 expression (FIG. 1H).

Figure 2A:
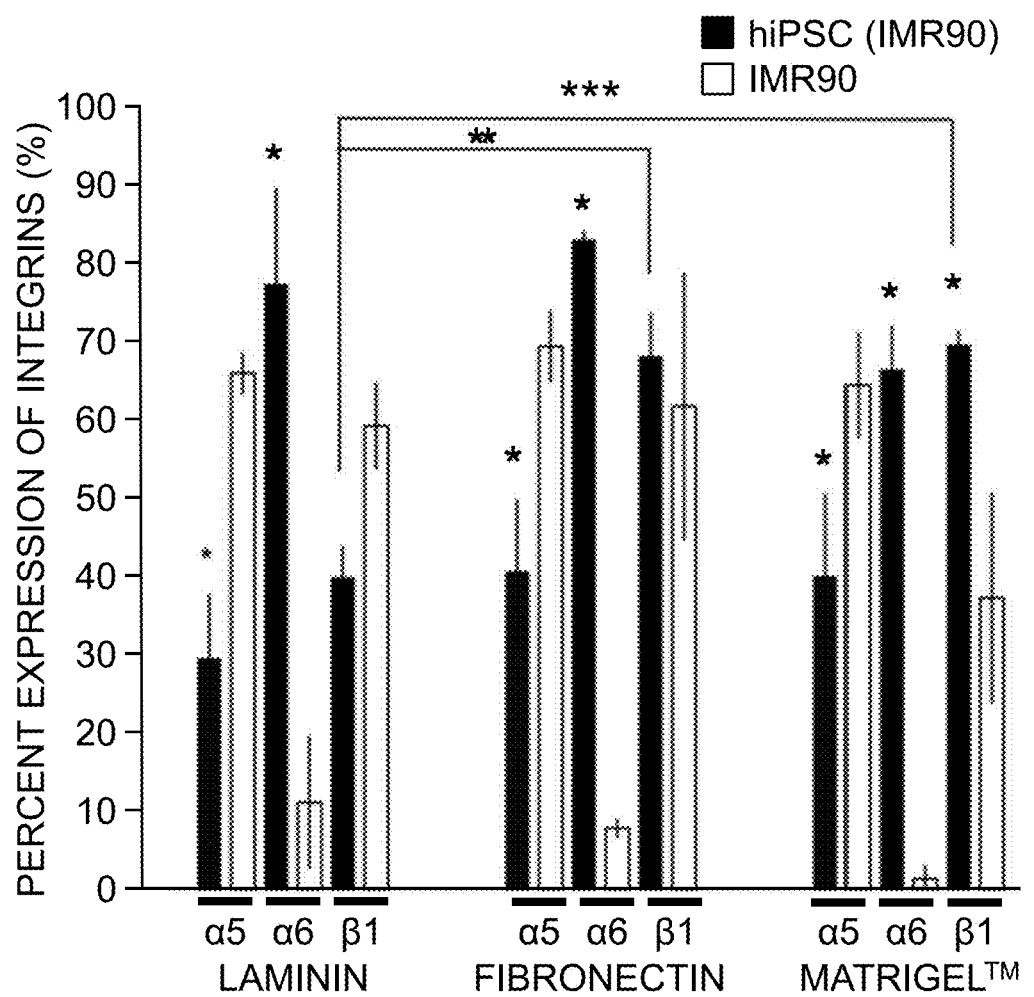
FIG. 2A. Flow cytometry measurement of integrins expressed on hiPSCs and IMR90 cells cultured on laminin, fibronectin, and Matrigel™ (*$p<0.05$ hiPSC vs. IMR90, $p<0.05$ laminin vs. fibronectin, *$p<0.05$ laminin vs. Matrigel™).
Figure 2B:
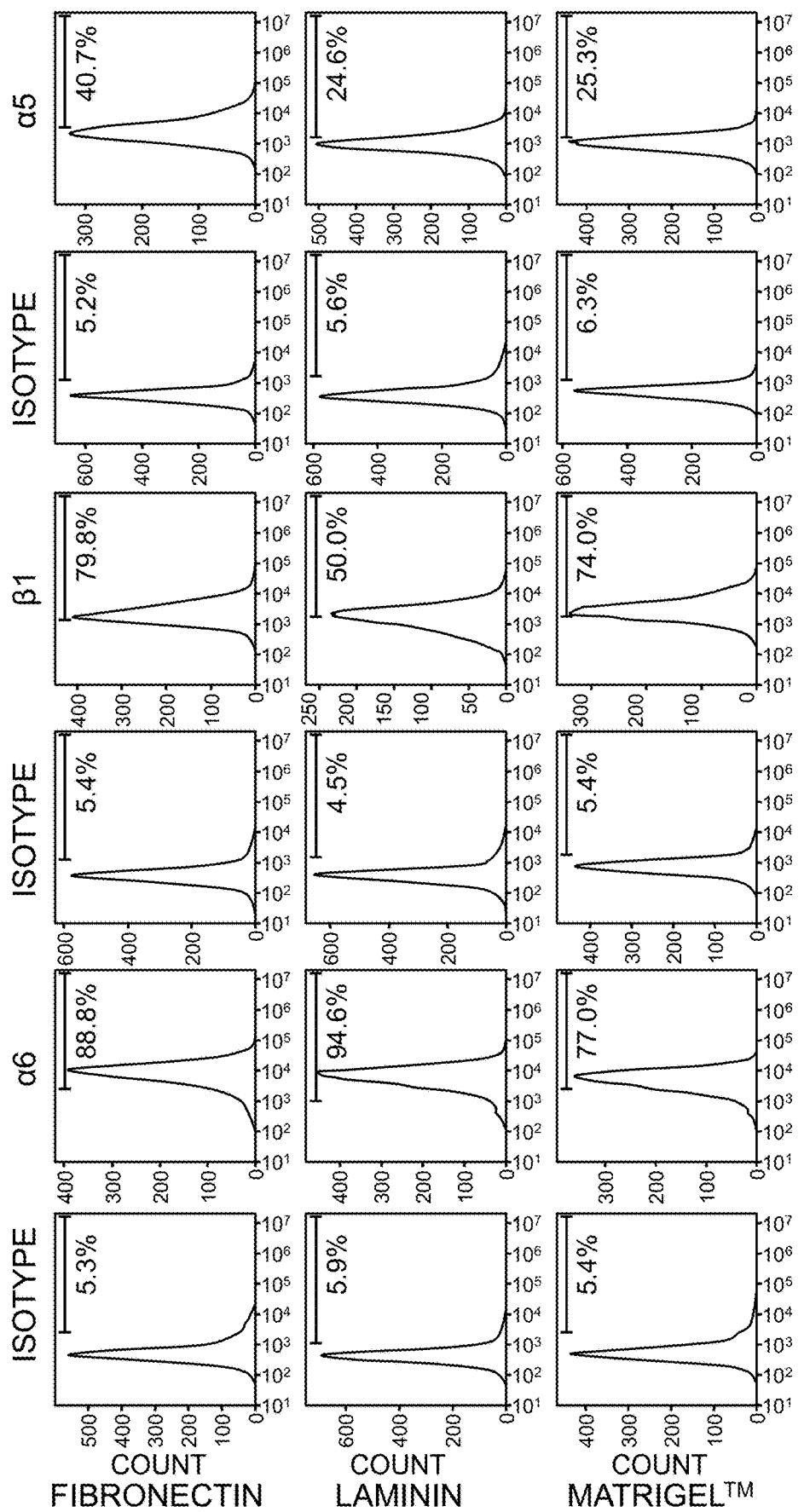
FIG. 2B. Flow cytometry measurements of integrins expressed by hiPSCs cultured on laminin, fibronectin, and Matrigel™. Histogram represents fluorescence intensity distribution of integrins and corresponding isotype controls. All % corresponding to cells expression 5-6% receptors for isotype antibody (background).
Figure 2C:
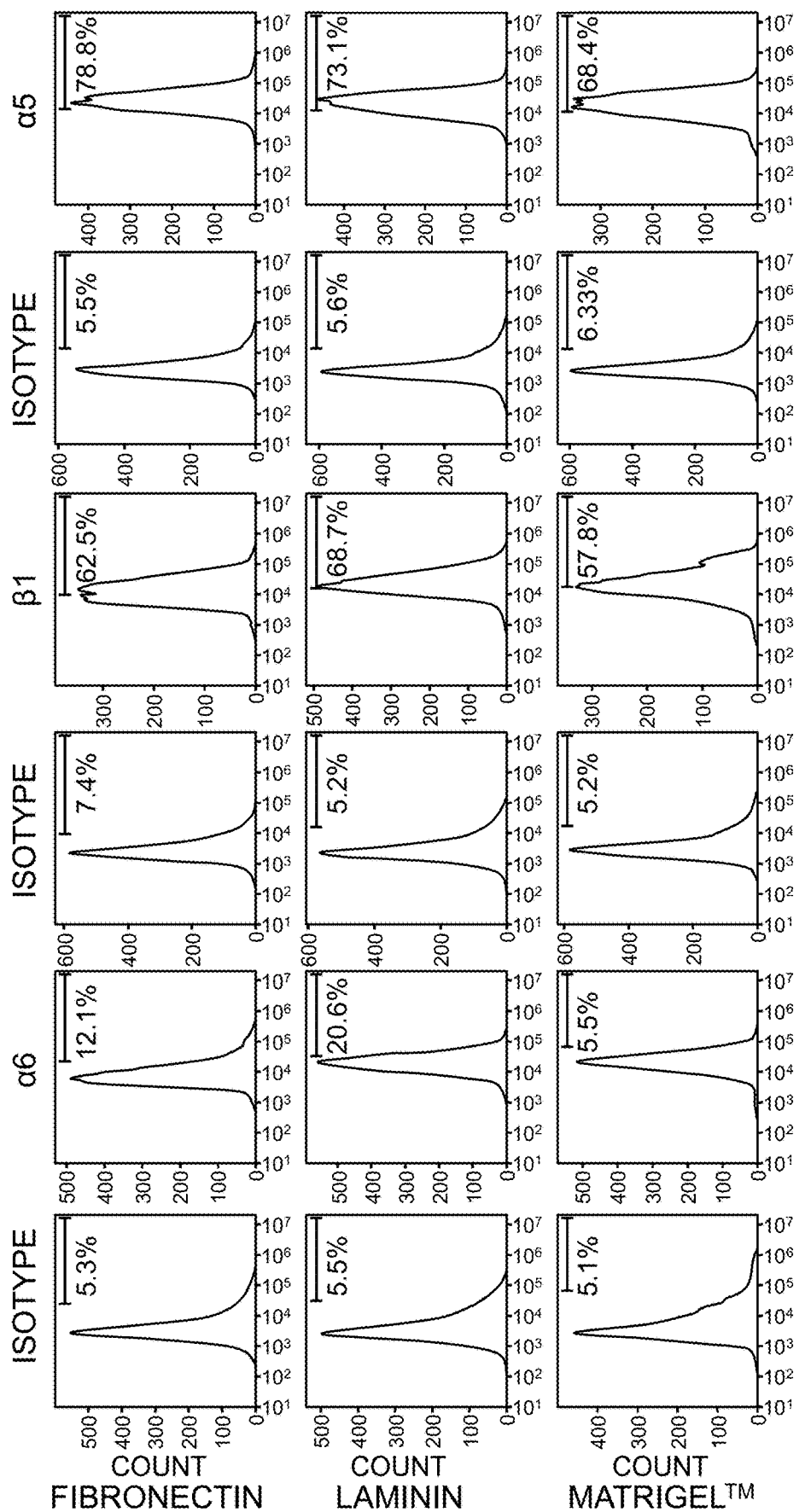
FIG. 2C. Flow cytometry measurements of integrins expressed by IMR90 fibroblasts cultured on laminin, fibronectin, and Matrigel™. Histogram represents fluorescence intensity distribution of integrins and corresponding isotype controls.
Figure 2D:
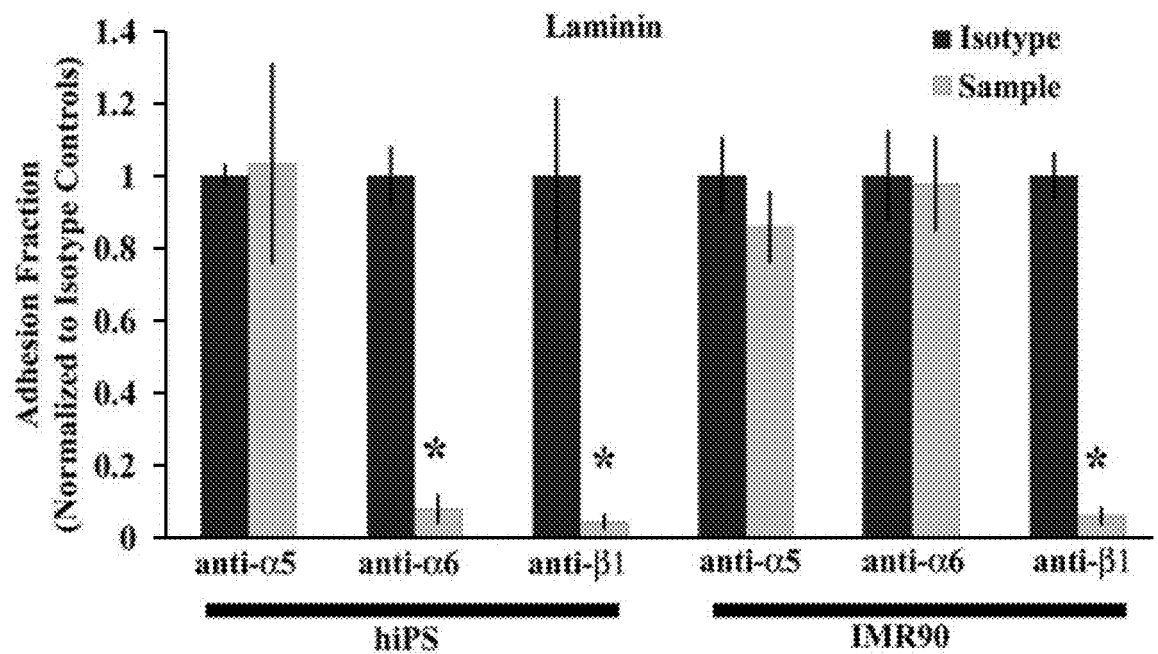
FIG. 2D. Blocking of integrin-mediated adhesion on laminin matrices using integrin-specific blocking antibodies ($*p<0.05$ integrin vs. isotype).
Figure 2E:
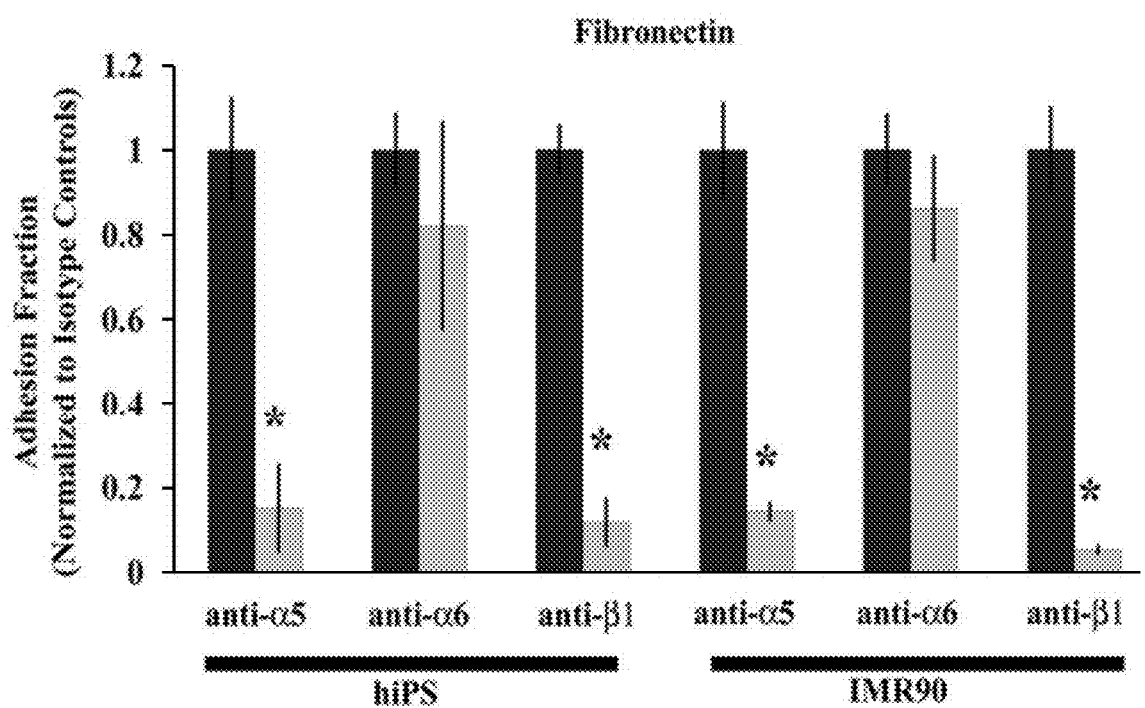
FIG. 2E. Blocking of integrin-mediated adhesion on fibronectin matrices using integrin-specific blocking antibodies ($*p<0.05$ integrin vs. isotype).

Changes in integrin profiles expressed by the parental fibroblast and the reprogrammed state were examined. IMR90 fibroblasts and hiPSCs were cultured on fibronectin or laminin and analyzed for expression of several α and β integrin subunits. Differences in expression of integrins α5, α6, and β1 involved in fibroblast and UD-hiPSC adhesion to fibronectin, laminin, and Matrigel™ were observed (FIG. 2A). Flow cytometry analyses revealed 30-35% higher expression of α5 integrins by IMR90 fibroblasts compared to hiPSCs, regardless of whether the cells were cultured on fibronectin, laminin or Matrigel™ ($p<0.05$, FIG. 2A). In contrast, hiPSCs expressed 60-70% more α6 integrins than IMR90 cells for all matrices (FIGS. 2A-2C). The expression of β1 subunit by hiPSCs was significantly higher only when cultured on Matrigel™ compared to IMR90 cells. Adhesion inhibition studies using blocking antibodies revealed that β1 integrin was involved in mediating IMR90 and hiPSC adhesion to these matrices (FIG. 2D). Blocking α6 integrin significantly reduced hiPSC adhesion to laminin but did not inhibit the adhesion of IMR90 cells (FIGS. 2D-2E). Furthermore, blocking α5 integrins significantly reduced the adhesion of hiPSCs and IMR90 cells to fibronectin but it did not alter adhesion to laminin (FIGS. 2D-2E). The high α6β1 integrin expression in hiPSCs is in agreement with previous studies of hESCs (Meng et al., *FASEB J* 24:1056-1065 (2010)).

The steady state cell adhesion strength for parental fibroblasts and hiPSCs on ECM-coated adhesive islands of different dimensions was evaluated using a spinning disk device (Garcia et al., *J. Biol. Chem.* 273:10988-10993 (1998); Gallant et al., *Mol. Biol. Cell* 16:4329-4340 (2005); Dumbauld et al., *J Cell Physiol.* 223:746-756 (2010)). This device applies a range of well-defined hydrodynamic forces to adherent cells and provides sensitive measurements of adhesion strength. Adherent cells were exposed to laminar fluid flow to produce a detachment force that is proportional to the hydrodynamic wall shear stress ($\tau$, force/area). The applied detachment force varies linearly with radial position along the surface of the sample, resulting in the application of a range of forces in a single experiment. The adhesion strength response was analyzed on adhesive surfaces coated with saturating fibronectin or laminin concentrations (50 μg/ml), or Matrigel™ (1:80 dilution).

Figure 3A:
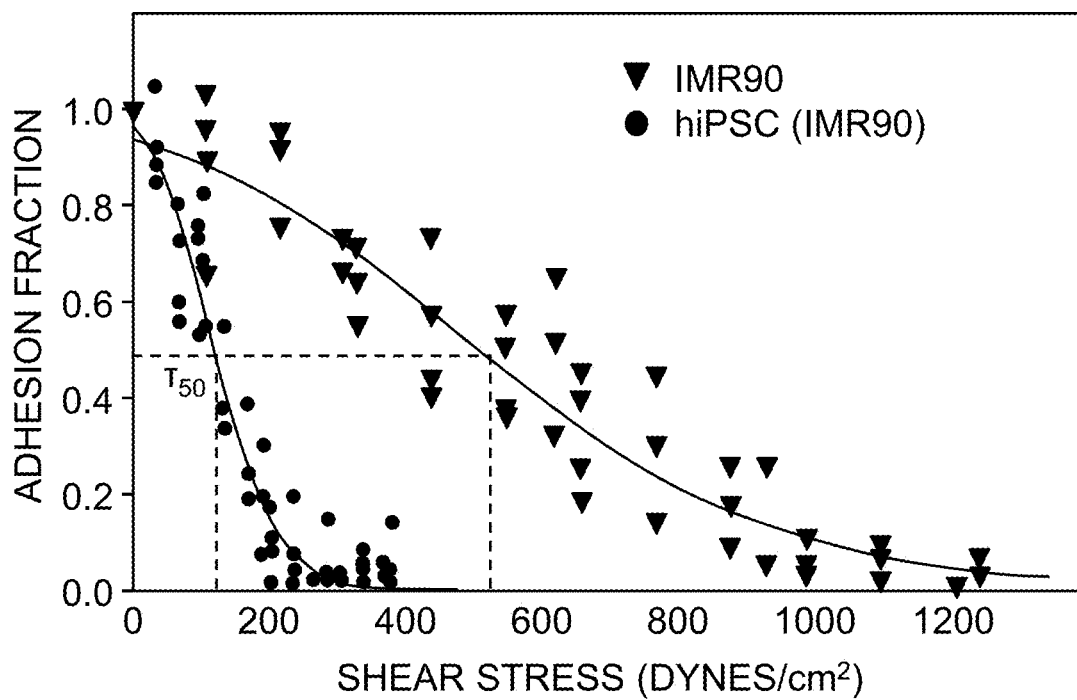
FIG. 3A. Detachment profile showing adherent cell cluster fraction vs. applied shear stress for hiPSCs and IMR90 cells at 16 hours. Experimental points were fit to sigmoid to obtain the shear stress for 50% detachment $\tau_{50}$.
Figure 3B:
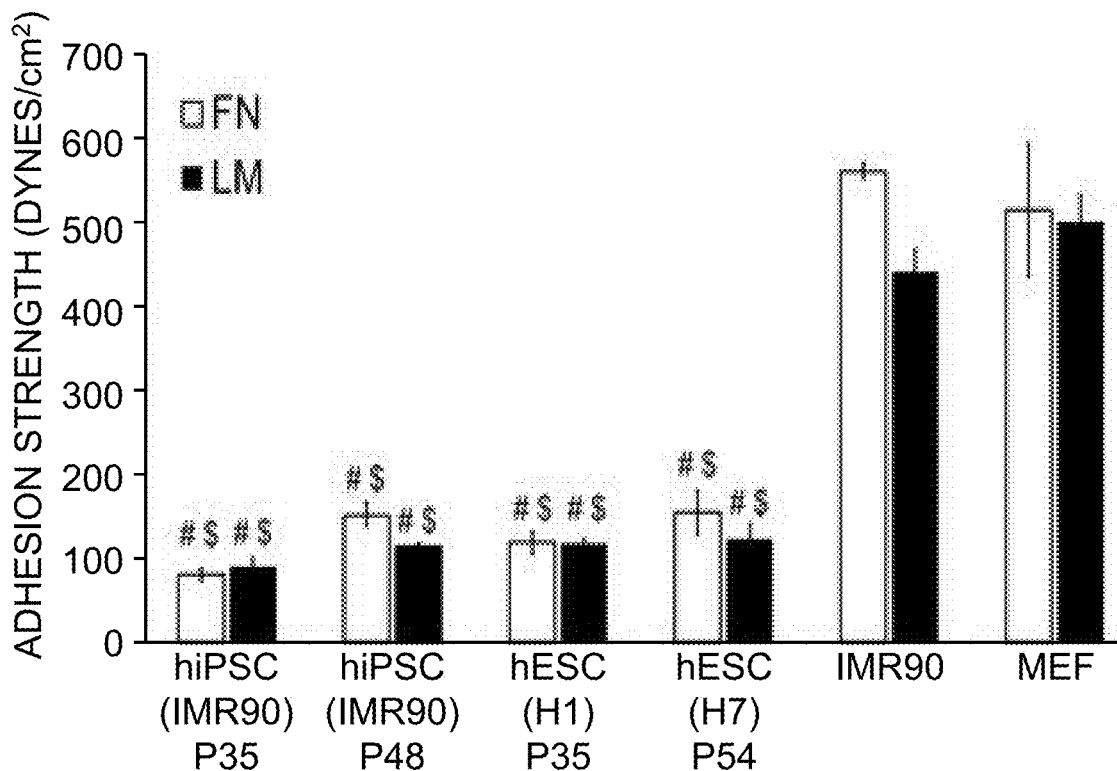
FIG. 3B. Adhesion strength ($\tau_{50}$) measurements for undifferentiated hiPSCs (derived from IMR90), hESCs (H7 and H1), IMR90 and MEF cells on fibronectin and laminin substrates. Bar graph represents average±S.D. ($\#p<0.05$ stem cells vs. IMR90s, $\$p<0.05$ stem cells vs. MEFs).
Figure 3C:
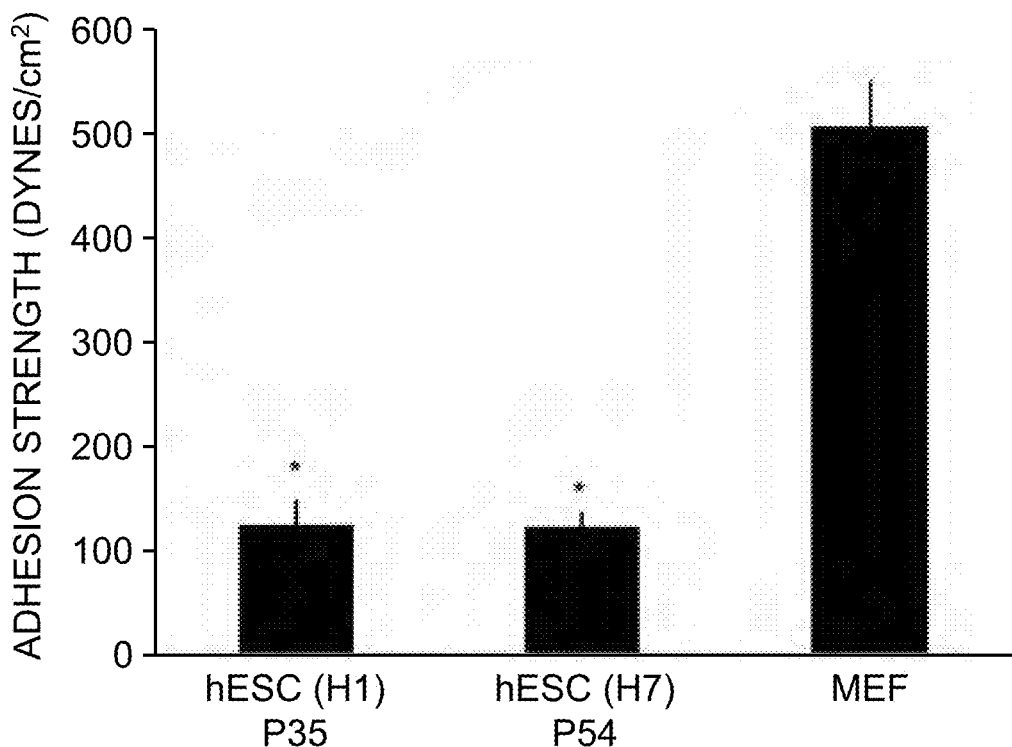
FIG. 3C. Adhesion strength measurements for undifferentiated hESCs (H7 and H1) compared to MEF on Matrigel™. Bar graph shows average±S.D. ($*p<0.05$ stem cells vs. MEF).
Figure 3D:
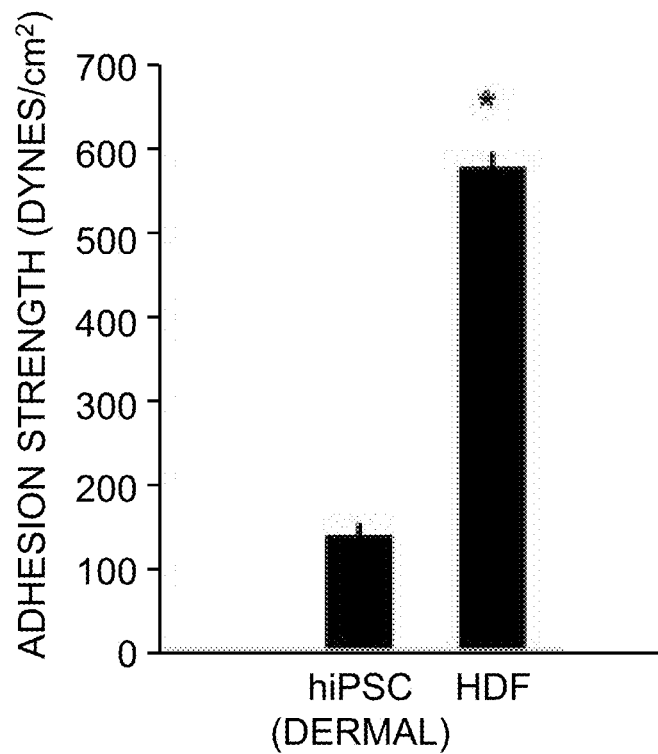
FIG. 3D. Adhesion strength measurements for undifferentiated hiPSCs (derived from dermal fibroblasts, 11b) and human dermal fibroblasts on laminin substrates. Bar graph represents average±S.D. ($*p<0.05$ stem cells vs. fibroblasts).

Because of differences in cell morphology and spreading that accompany the pre- and post-reprogramming states, we evaluated whether hiPSCs exhibit lower adhesive strength (shear stress for 50% detachment ($\tau_{50}$)) than parental fibroblasts. FIG. 3A presents detachment profiles for hiPSCs and IMR90 cells; each profile shows a sigmoidal decrease in the fraction of adherent cells/clusters with increasing shear stress. The significant left-ward shift in the sigmoidal profile for hiPSCs compared to IMR90 cells indicates a reduction in the adhesion strength for reprogrammed hiPSCs. Adhesion strength analysis revealed approximately seven-fold lower adhesion strength for hiPSCs ($81\pm7.6$ dynes/cm$^2$) on fibronectin compared to parental IMR90 fibroblasts ($560\pm8.9$ dynes/cm$^2$) ($p=0.0002$, FIG. 3B). Adhesion strength studies were conducted among hiPSC (IMR90) and hESCs (H1, H7), compared to IMR90 (as parental cells) and MEFs cultured on laminin (FIG. 3B) and Matrigel™ (FIG. 3C). The overall adhesion strength was significantly lower ($p<0.02$) for hPSCs (FIG. 3C) compared to either of the fibroblastic cells, indicating the dramatic shift in adhesive properties between the pre-and-post stages of reprogramming for hiPSCs, which are equivalent to those observed with hESCs. These results were independent of passage number of the hPSCs and underlying matrix. The adhesion strength of hiPSCs derived from dermal fibroblasts (male donor, OSK factors, Harvard Stem Cell Institute) was similar to hiPSC (IMR90) and significantly lower than parental human dermal fibroblasts (FIG. 3D), clearly indicating that the adhesive signature is unique to true hiPSCs and not dependent on the source, number of reprogramming factors, or type of parental fibroblast, but rather on the phenotypic state of the pluripotent stem cells. Collectively, these results indicate differences between the adhesive signature of hPSCs and parental cells.

Figure 3E:
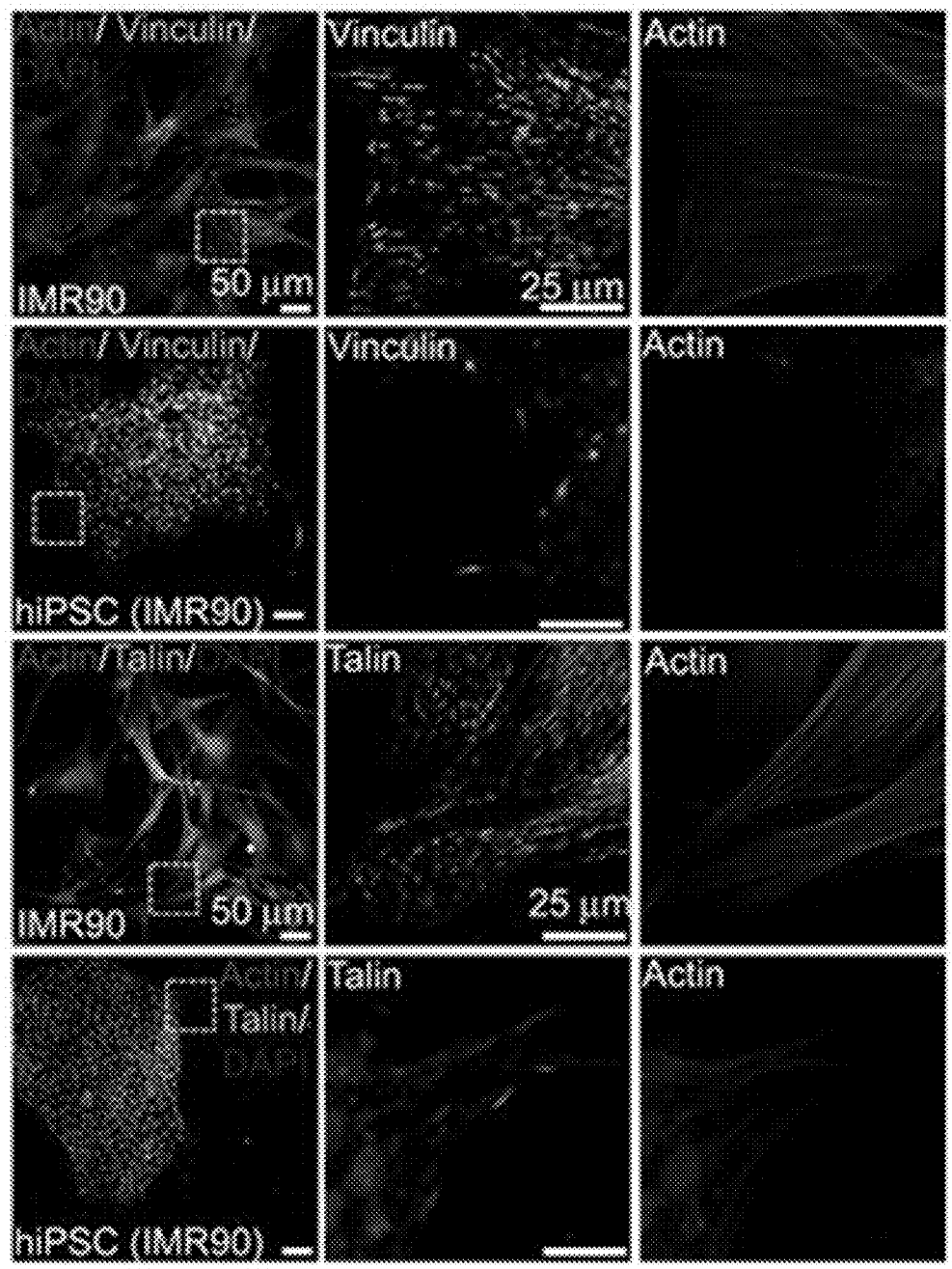
FIG. 3E. Immunostaining showing recruitment of vinculin and talin to focal adhesions in IMR90 cells and UD-hiPSCs on laminin substrates.

The reprogramming-induced morphological changes led to the examination of alterations in cytoskeletal structure and focal adhesion assembly. Fibroblasts possessed well-defined actin stress fibers parallel to the long axis of cell (FIG. 3E). In contrast, reprogrammed hiPSCs exhibited significantly fewer actin fibers that were localized to cell-cell junctions (FIG. 3E). The cytoskeletal proteins talin and vinculin have emerged as central regulators of adhesive functions (Gallant et al., *Mol. Biol. Cell* 16:4329-4340 (2005); Balaban et al., *Nat. Cell Biol.* 3:466-472 (2001); Dumbauld et al., *Biol. Cell* 102:203-213 (2010)). In IMR90 fibroblasts, vinculin and talin were strongly enriched at focal adhesions (FIG. 3E). hiPSCs displayed few focal adhesions and vinculin and talin staining was diffuse throughout the cytoplasm or localized to the cell-cell junctions and sometimes at the tip of projecting small filopodia (FIG. 3E). Observations for focal adhesions were similar for cells cultured on fibronectin-, laminin-, and Matrigel™-coated surfaces. The differences in adhesive force correlated directly to the increased localization of vinculin and talin to focal adhesions in IMR90 cells compared to hiPSCs and are therefore indicative of a distinct "adhesive signature" in hPSCs.

Figure 3F:
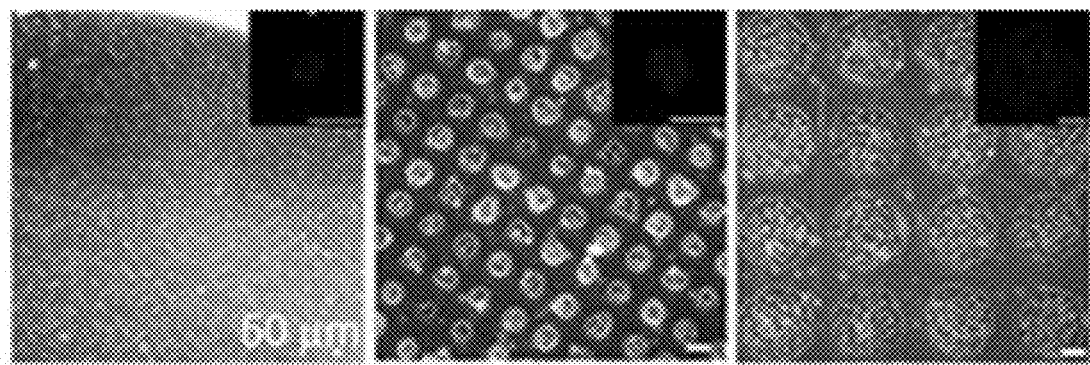
FIG. 3F. Phase contrast images of micropatterned hiPSC clusters on 20, 56, and 170 μm diameter fibronectin adhesive islands. Inset shows a single cell cluster with DAPI-stained nuclei.
Figure 3G:
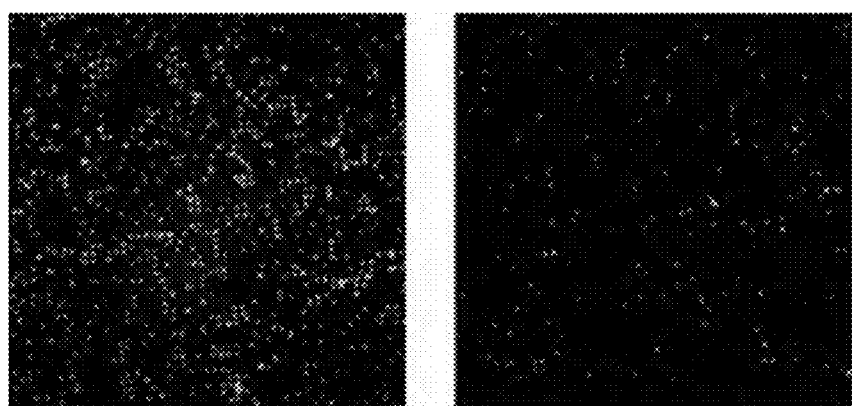
FIG. 3G. Micropatterned hiPSCs on 10 μm size adhesive islands of fibronectin. Cells adhered as single cells and significant cell loss was observed overnight.
Figure 3H:
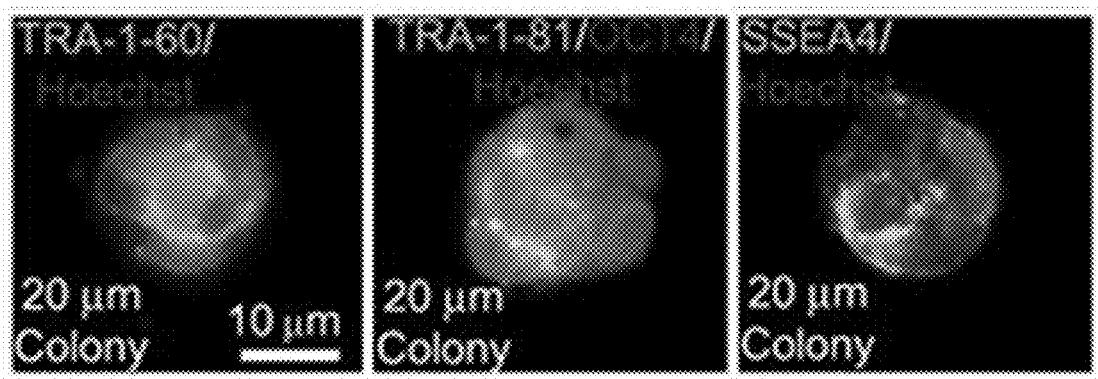
FIG. 3H. Immunofluorescence images showing undifferentiated state of hiPSCs stained for OCT4, SSEA4, TRA-1-60, TRA-1-81 on micropatterned substrates.
Figure 3I:
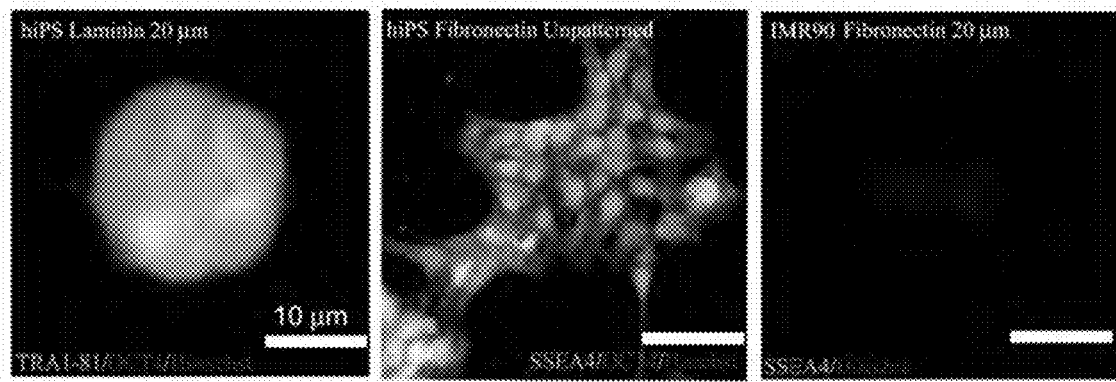
FIG. 3I. Immunofluorescence images showing undifferentiated state of hiPSCs stained for pluripotency markers on laminin and fibronectin (overnight). IMR90 cells were used as negative control.
Figure 3J:
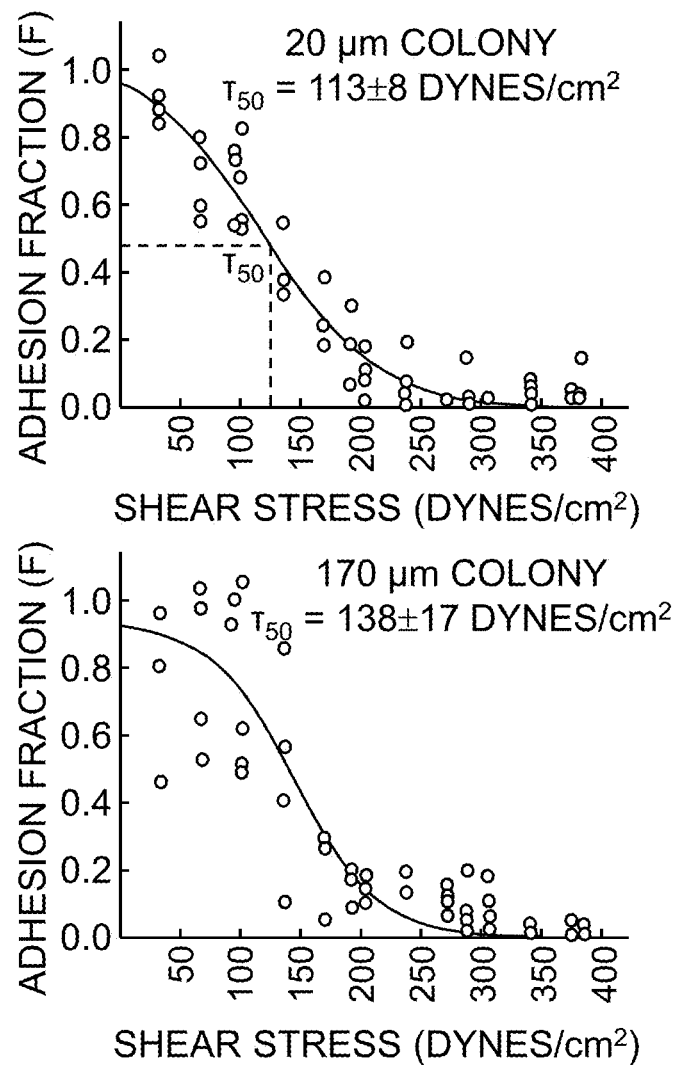
FIG. 3J. Detachment profile showing adherent cell cluster fraction vs. applied shear stress for hiPSCs on 20 μm (upper panel) and 170 μm (lower panel) diameter islands.

Whereas fibroblasts exist typically as individual spread cells, it is not clear how the multicellularity, colony size, and cell-cell adhesion of hiPSC cells influence biophysical properties such as adhesion strength. It is optimal for hiPSC survival and undifferentiated phenotype to exist as epithelial-like colonies with E-cadherin-based cell-cell adhesion (Chen et al., *Cell Stem Cell* 7:240-248 (2010); Ohgushi et al., *Cell Stem Cell* 7:225-239 (2010)). Using micropatterned substrates, the functional dependence of adhesion strength of hiPSCs on cluster/colony size and epithelial cell cluster numbers was examined. Arrays of circular adhesive islands of varying dimensions (10, 20, 56, and 170 μm diameter) were engineered to examine a nearly 100-fold range in available adhesive area (FIG. 3F). Whereas on the larger islands, hiPSCs colonies adhered well and exhibited high (>95%) viability, hiPSCs adhered loosely as individual cells on 10 μm adhesive islands and did not survive in overnight culture (FIG. 3G). The colony size, and thus number of cells per colony, increased with adhesive area (FIG. 3G; Table 2) and hiPSCs cultured on adhesive micropatterned islands retained expression of OCT4, SSEA4, TRA-1-60, and TRA-1-81 (FIGS. 3H and 3I). The adhesion strength of hiPSCs was independent of colony size; no significant differences in adhesion strength were observed over a 70-fold increase in adhesion area and 14-fold increase in the multi-cellularity of the clusters (FIG. 3j). The lack of dependence of adhesion strength on colony size is not surprising because increasing the colony size does not alter the morphology of the cells, just the number of cells per colony.

TABLE 2

| Island Diameter | hiPSC Colony Area | Average Cell Count |
| --- | --- | --- |
| 20 μm | 314 μm$^2$ | 4 ± 1 |
| 56 μm | 2463 μm$^2$ | 8 ± 2 |
| 170 μm | 22700 μm$^2$ | 70 ± 10 |

Figure 4A:
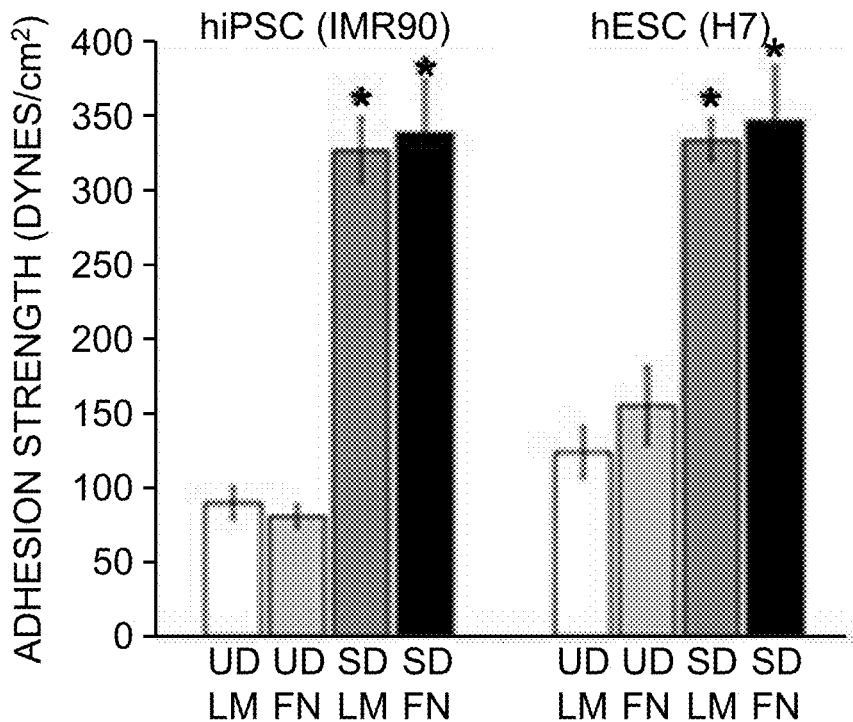
FIG. 4A. Adhesion strength measurements for spontaneously differentiated (SD) hiPSCs (derived from IMR90) and hESCs (H7) compared to respective undifferentiated (UD) cells cultured on fibronectin (FN) and laminin (LM). Bar graph represents average±S.D. ($*p<0.05$ undifferentiated cells vs. differentiated cells).
Figure 4B:
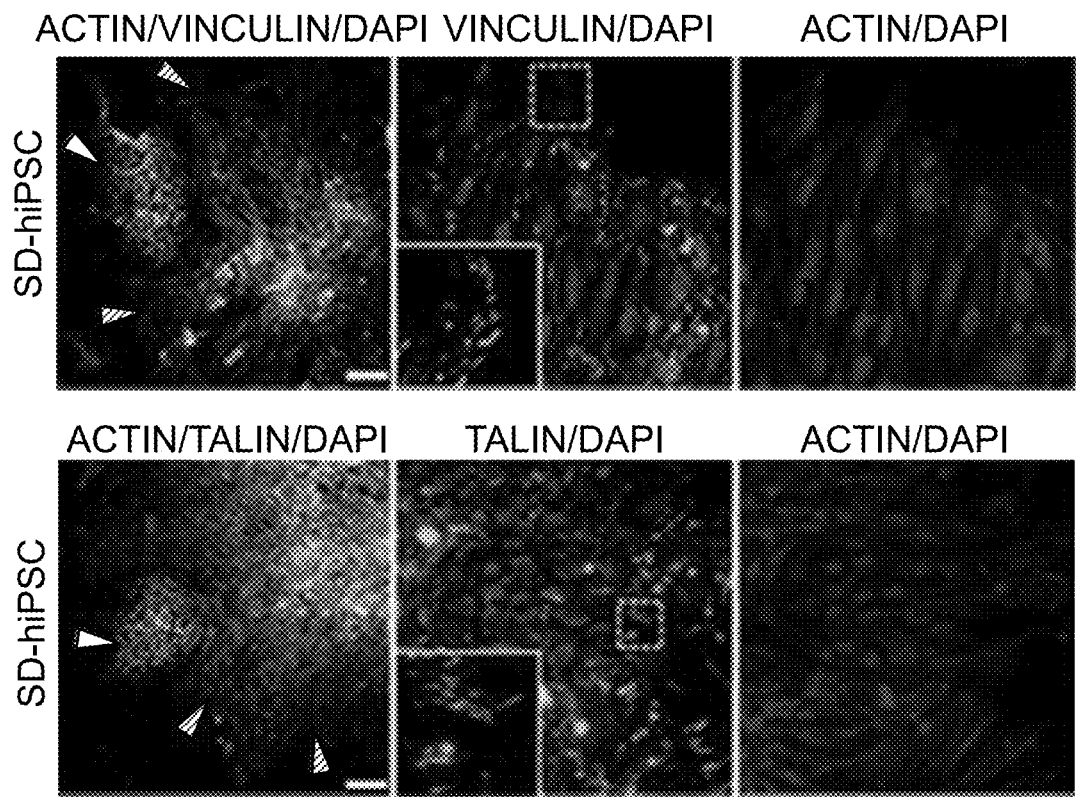
FIG. 4B. Immunostaining showing recruitment of vinculin and talin to focal adhesions in SD-hiPSCs (filled arrowhead) distinct from UD-hiPSCs (white arrowhead) cultured on fibronectin. Bar, 50 μm.
Figure 4C:
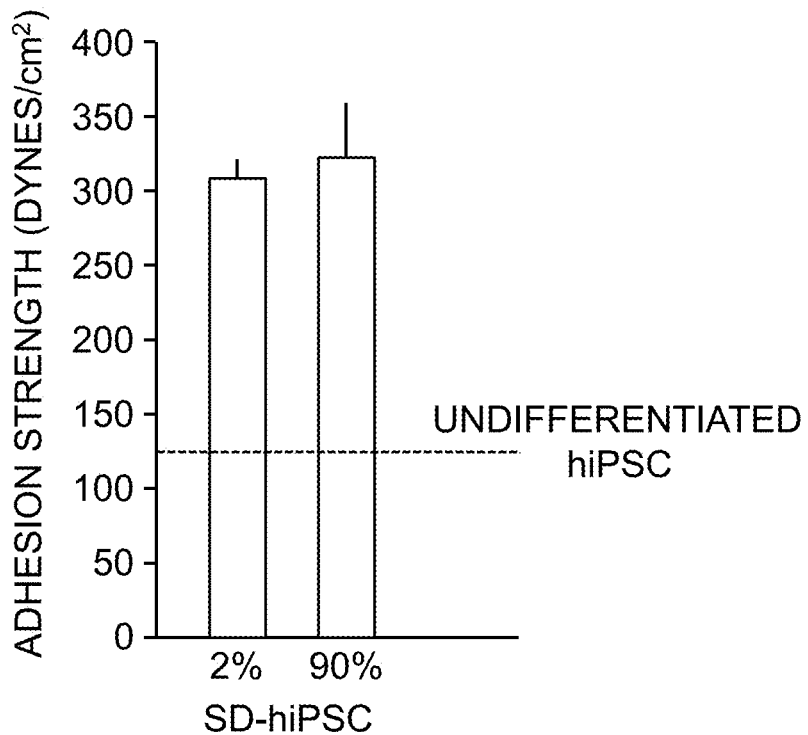
FIG. 4C. Adhesion strength measurements for spontaneously differentiated hiPSCs (derived from IMR90) with 2% and 90% differentiation and compared to undifferentiated cells cultured on laminin. Bar graph represents average+S.D.; horizontal dashed line represents average adhesion strength of UD-hiPSCs.

Adhesion strength analyses were performed on SD-hiPSCs and SD-hESCs (>90% differentiated; ~10% TRA-1-60+via flow cytometry), and as indicated in FIG. 4A, there were significant increases ($p<0.006$) in adhesion strength of SD-hiPSCs on fibronectin (340±36 dynes/cm$^2$) and laminin (330±22 dynes/cm$^2$) compared to UD-hiPSC adhesion values below 100 dynes/cm$^2$. Similar adhesion strength differences were observed for SD-hESCs (H7) on laminin and fibronectin (330±14 dynes/cm$^2$) compared to UD-hESCs (H7, 120±17 dynes/cm$^2$) on laminin. Focal adhesion analyses were subsequently performed on hiPSC cell cultures with partially spontaneous differentiated areas. In SD-hiPSCs, well-defined actin stress and localization of vinculin and talin to focal adhesions were readily observed (FIG. 4B) in the differentiated areas compared to undifferentiated colonies or parts of the colonies where vinculin and talin were present only at the filopodia or diffuse throughout the cytoplasm. Importantly, the differences in adhesion strength between undifferentiated cells and differentiated cells were not dependent on the levels of spontaneous differentiation as differences between cultures containing 2% or 90% differentiated cells were not observed (FIG. 4C).

Figure 4D:
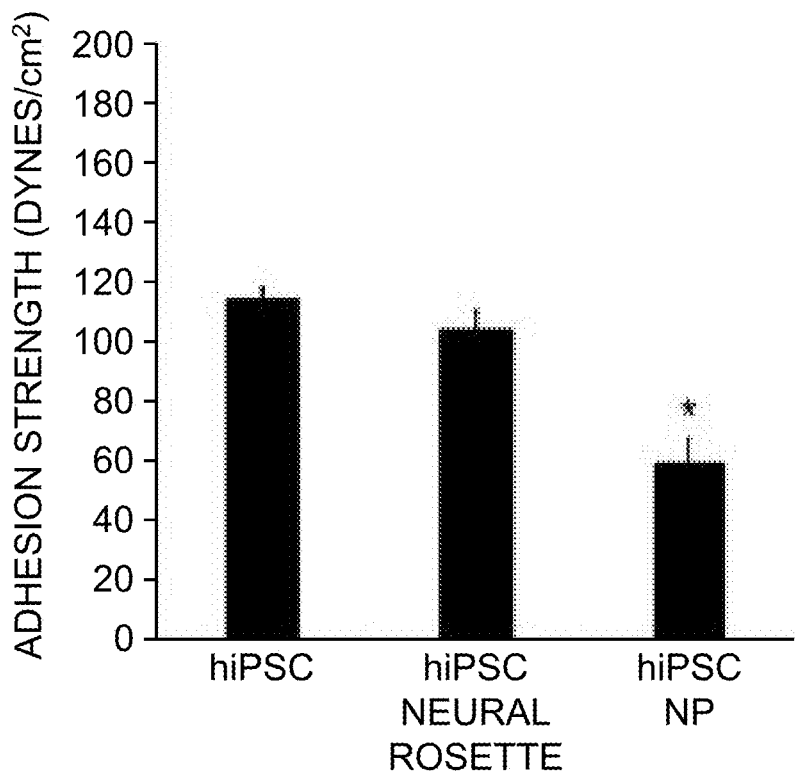
FIG. 4D. Adhesion strength measurements for UD-hiPSCs, hiPSC-derived neural rosettes, and hiPSC-derived neural progenitors (NP) on laminin. Bar graph represents average±S.D ($*p<0.05$).
Figure 4E:
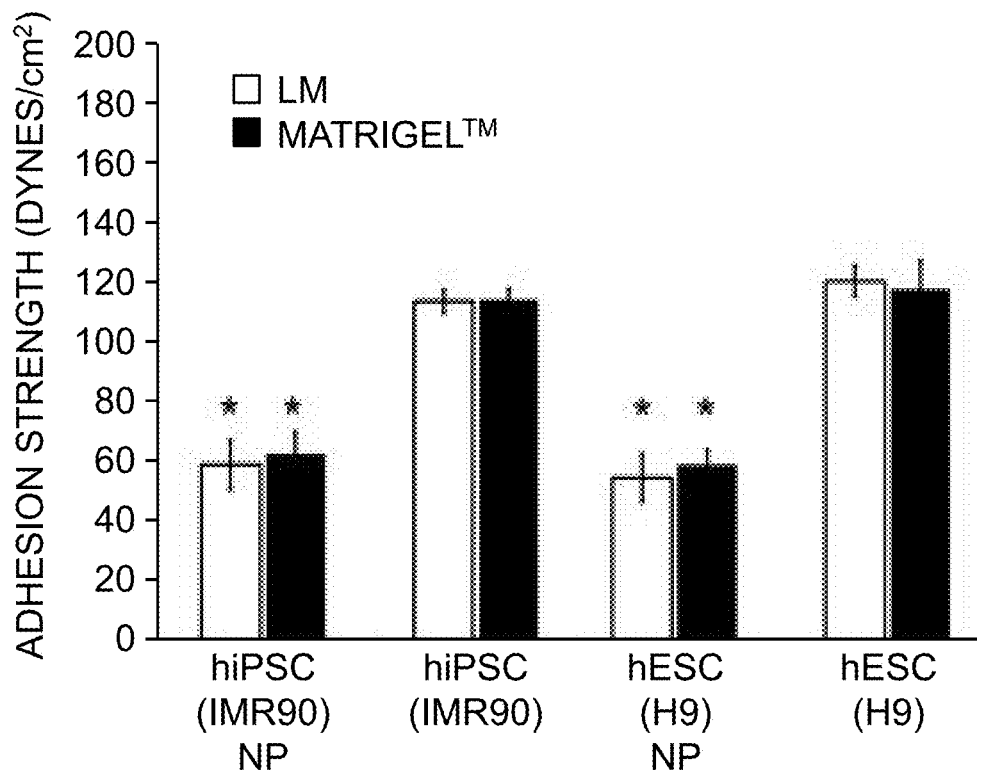
FIG. 4E. Adhesion strength measurements for neural progenitors (NP) derived from hiPSCs and H9 hESCs on laminin and Matrigel™ substrates. Bar graph represents average±S.D ($*p<0.05$).

The adhesive signature of directed differentiated cells was determined by assessing the adhesion strength of multi-potent neural rosettes and neural progenitors derived from hiPSCs and hESCs. Neural rosettes, which are formed within 3 weeks of directed differentiation of hiPSCs, exhibited comparable adhesion strength to undifferentiated hiPSCs from which they were derived, but had significantly lower strength compared to contaminating fibroblast-like cells ($p<0.05$, FIG. 4D). When hand-picked and further differentiated for two weeks, the rosettes form neural progenitors that exhibited half the adhesion strength of undifferentiated hiPSCs (FIG. 4D) and were independent of pluripotent stem cell type and matrix (FIG. 4E). Taken together, these analyses demonstrate significant differences in adhesion strength between UD-hPSCs and parental or SD-hPSCs, as well as between UD-hPSCs and directly differentiated progenitor cells.

Example 3

Rapid, Scalable, Hydrodynamic Isolation of Reprogrammed hiPS Cells from Contaminating Parental and Feeder Cells The unique adhesive signatures and differences in adhesion strength between the pre- and post-reprogrammed states of hiPSCs were exploited to develop a novel strategy to isolate and enrich for cells of interest among a heterogeneous population of cells. Adhesive force-based separation of two (or more) distinct cell populations using fluid shear stress via a simple microfluidic system represents a label-free separation technique, which requires minimal cell processing or exposure to electrical or magnetic separation fields, and can be employed to detach cells in their native cell-cell microenvironment. This technology is referred to herein as LSHEAR (micro Stem cell High-Efficiency Adhesion-based Recovery). High-throughput microfluidic devices offer several advantages over conventional hydrodynamic sorting assays including providing laminar flow with a million-fold less detachment buffer volume and excellent recovery of detached cells (Lu et al., *Anal. Chem.* 76:5257-5264 (2004)). Microfluidic devices also allow direct and continuous visualization of the detachment process. Easy loading of cells onto an inexpensive, self-contained disposable microfluidic device ensures a sterile environment for cell detachment and recovery and represents an excellent alternative to existing separation technologies like flow cytometers.

Figure 5A:
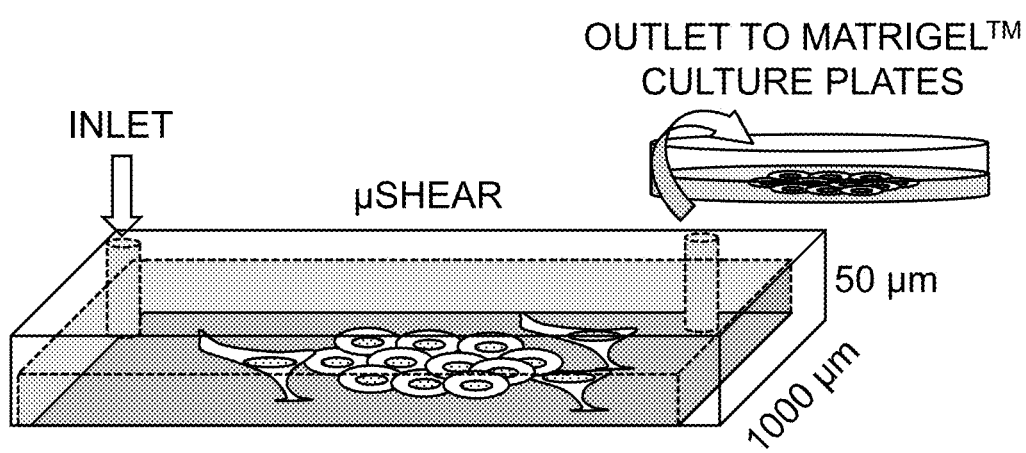
FIG. 5A. Schematic representing μSHEAR (micro Stem cell High-Efficiency Adhesion-based Recovery device) with co-cultured cells.
Figure 5B:
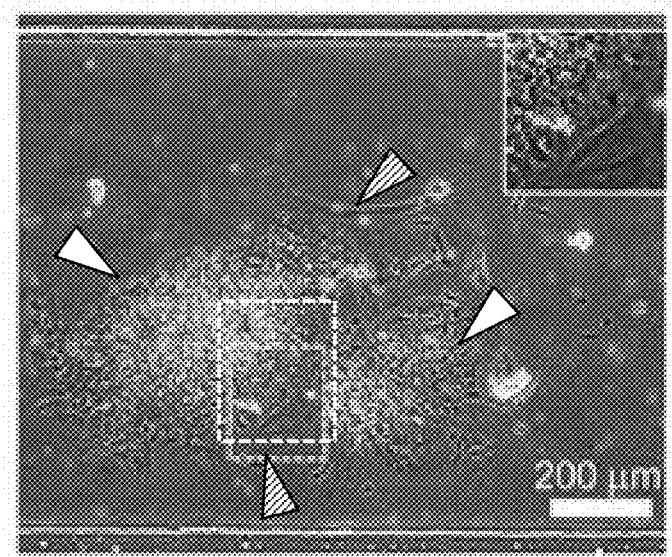
FIG. 5B. UD-hiPSCs (white arrowheads, compact epithelial colonies) and IMR90 cells (filled arrowheads, elongated cells) co-cultured in microfluidic channel.
Figure 5C:
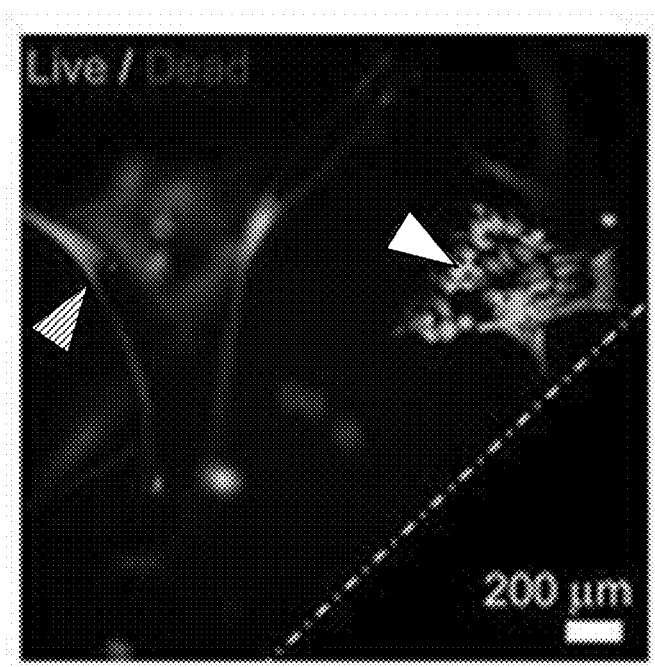
FIG. 5C. Live/Dead staining for viable hiPSCs (white arrowhead) and IMR90 cells (filled arrowhead). Live cells stained green for Calcein-AM while dead cells stain red for ethidium homodimer.
Figure 5D:
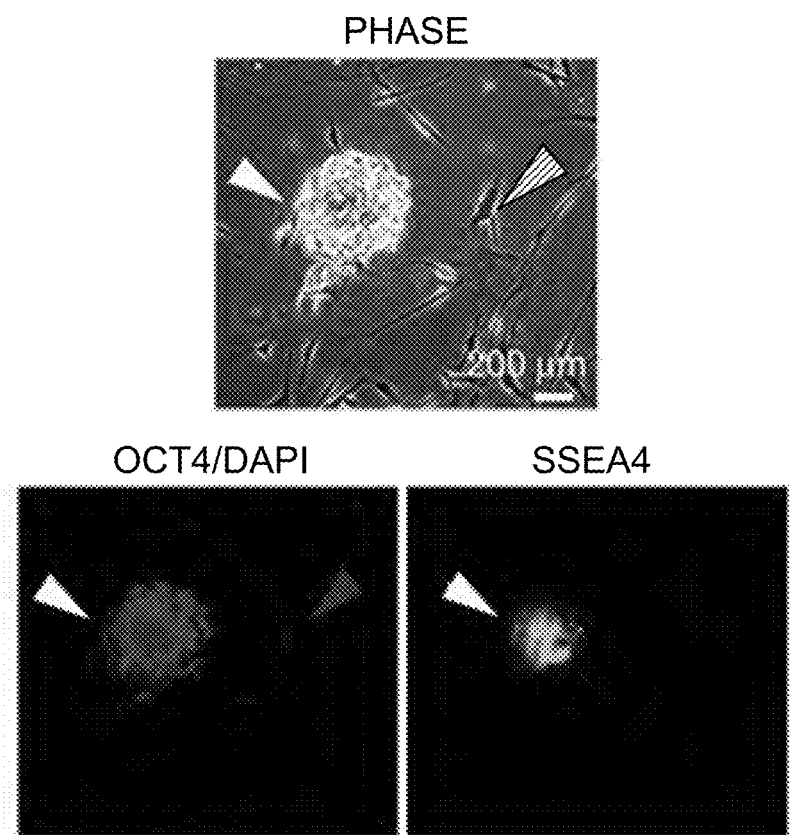
FIG. 5D. UD-hiPS cells (overnight culture) remain undifferentiated in microfluidic devices as stained positive for OCT4 and SSEA4.
Figure 5H:
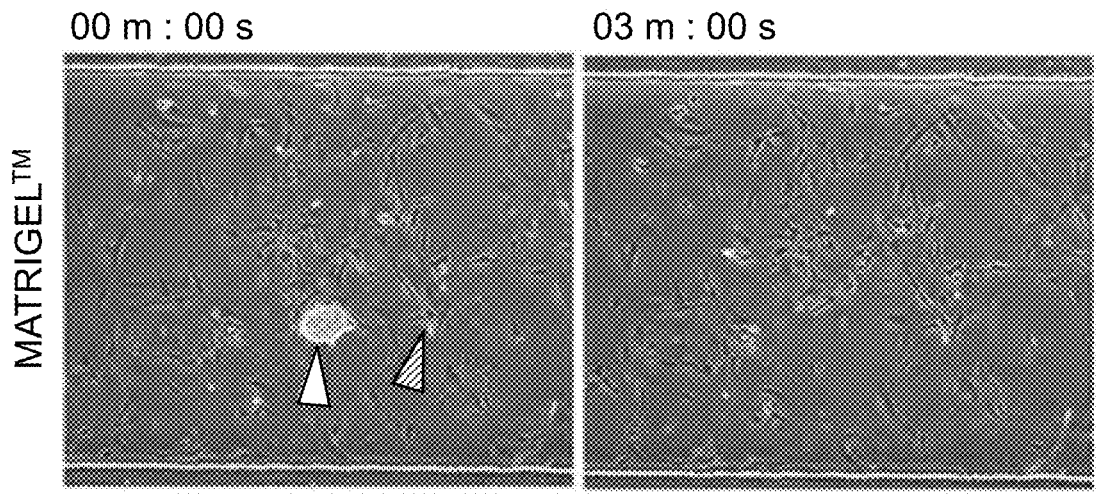
FIG. 5H. Selective detachment of UD-hiPSC colony (white arrow) from Matrigel™. Colonies were selectively detached at a shear stress of 85-125 dynes/cm$^2$.
Figure 5I:
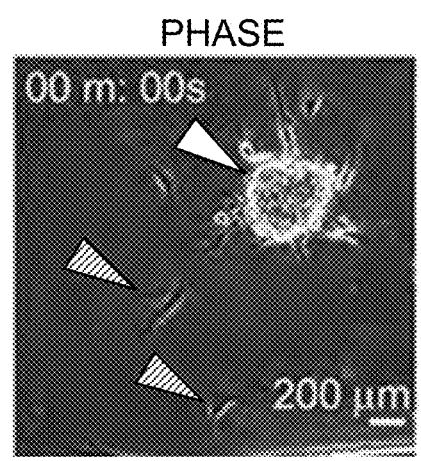
FIG. 5I. Selective detachment of pre-stained UD-hiPSC (white arrow) from hiPS/IMR90 co-culture demonstrating the ability to selectively detach low adhesion strength hiPSCs.
Figure 5I:
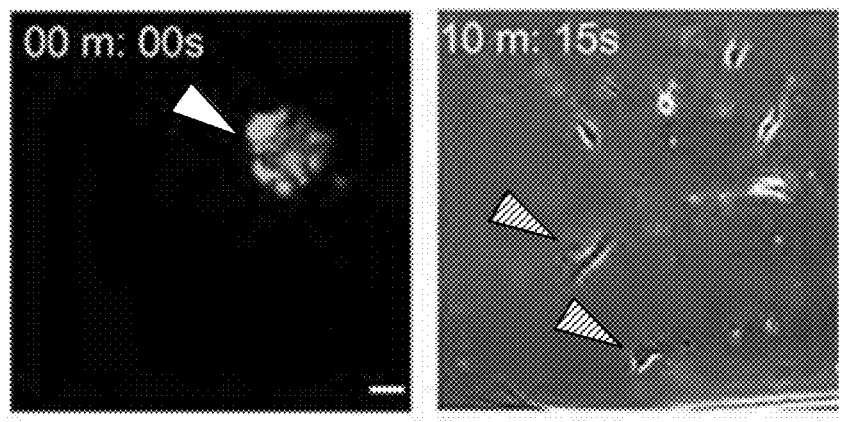

A parallel plate microfluidic device (μSHEAR) was used to introduce hiPSCs as colonies and culture them in the presence or absence of parental fibroblasts (FIG. 5A). Within the microfluidic device, the co-culture was morphologically evident with compact epithelial colonies of hiPSCs (high nucleus-cytoplasm ratio) and regions of spread IMR90 cells (FIG. 5B). Both cell types, cultured overnight in mTeSR®1 media with a ROCK-inhibitor, remained viable and retained their distinct morphologies (FIG. 5C). The hiPSC cells remained undifferentiated on fibronectin or laminin as demonstrated by positive expression of the pluripotency markers OCT4 and SSEA4 (FIG. 5D), whereas IMR90 cells did not express such pluripotency markers. Application of laminar flow in the microfluidic device generated fluid shear stresses on the adherent IMR90 cells and UD-hiPSC colonies. As shown in FIGS. 5E and 5F, hiPSC colonies started detaching at a shear stress of 85-125 dynes/cm$^2$ within 4 minutes of applying fluid flow and were completely detached from laminin-coated surfaces in 10±3 minutes, whereas the parental fibroblast with stronger adhesion properties remained attached. Similar results were obtained with cells cultured on fibronectin (FIG. 5G) and Matrigel™ substrates (FIGS. 5H-5I) thus indicating that detachment force is a function of cell phenotype and is largely insensitive to the underlying ECM.

Figure 6:
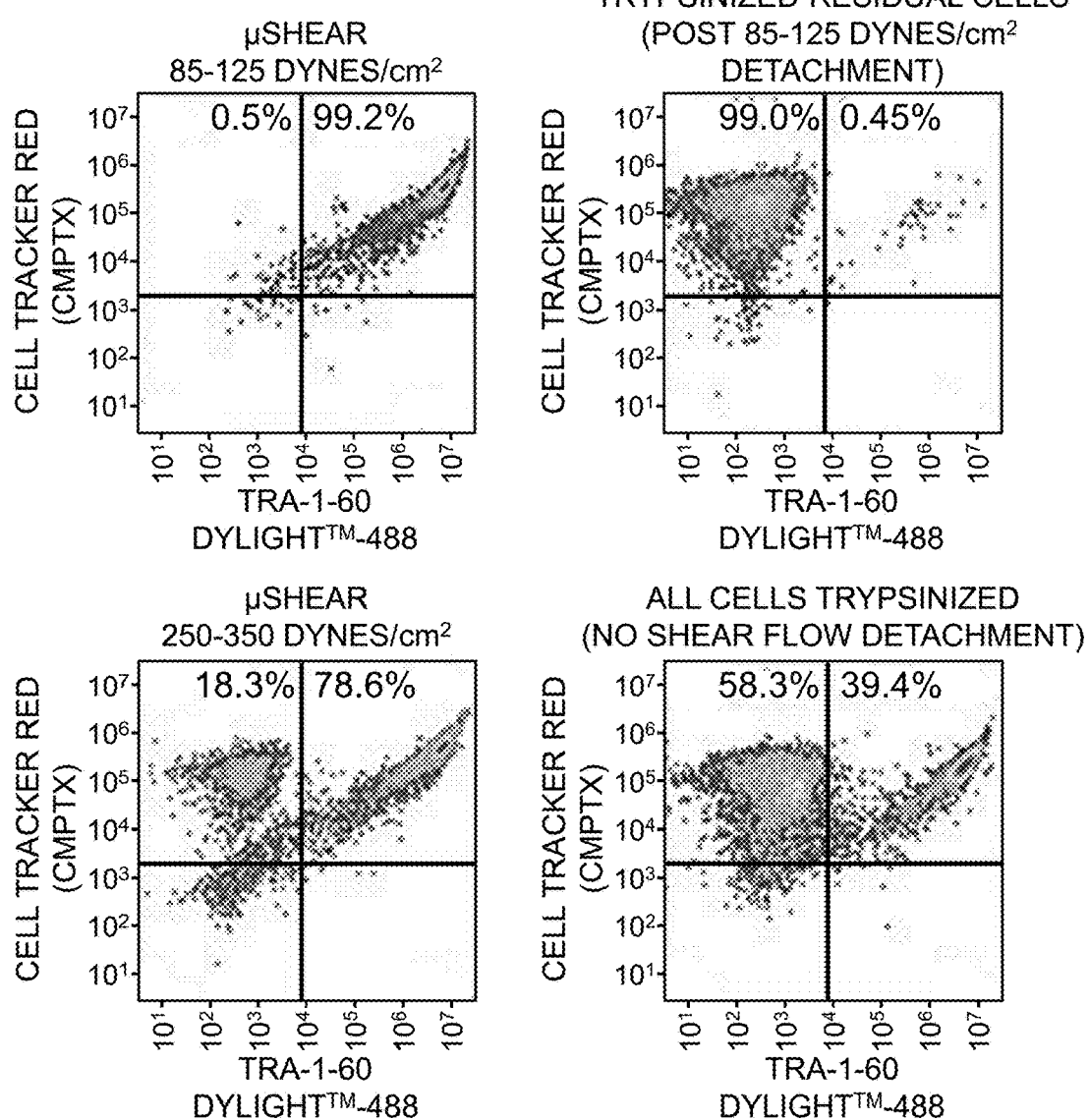
FIG. 6. Flow cytometry plots showing detached hiPSCs (positive for TRA-16-60 and CMPTX) and IMR90 cells (positive for CMPTX only). At 85-125 dynes/cm$^2$ shear stress, hiPSCs selectively detached yielding 99% purity, while at 250 dynes/cm$^2$ shear stress both hiPSC and IMR90 cells detached. For post-μSHEAR-based detachment, residual cells in the devices were trypsinized and analyzed (upper right panel). Controls used were co-culture populations in devices not exposed to flow based and all cells recovered by trypsinization (lower right panel).

To quantify the efficiency of UD-hiPSC isolation and purification from mixed cultures using μSHEAR, three different shear stresses were used to detach fibroblast-hiPSC co-culture populations with an initial baseline purity of 39% UD-hiPSCs (determined at detachment time). Detached cells were then stained with StainAlive™-DyLight™488-conjugated TRA-1-60 antibody to stain for live UD-hiPSCs. The entire recovered cell population was further stained with Cell Tracker Red dye (CMPTX) to assess non-UD-hiPSC contamination in the detached population. Flow cytometry analysis (FIG. 6) of the recovered cells revealed significant enrichment of hiPSCs when detached at 85-125 dynes/cm2 with up to 99% purity (DyLight™ TRA-1-60+ and CMPTX+) compared to samples detached using trypsin (39%, baseline purity). Samples exposed to higher flow rates in the range of 250-350 dynes/cm2 resulted in IMR90 detachment and contamination with up to 18% cells positive for IMR90 cells (CMPTX+) compared to 85-125 dynes/cm2 with less than 1% fibroblast contamination. We observed high proportions of IMR90 cells in detached samples exposed to 750-850 dynes/cm2, similar to trypsinized samples under no shear flow conditions (FIG. 6).

Figure 7B:
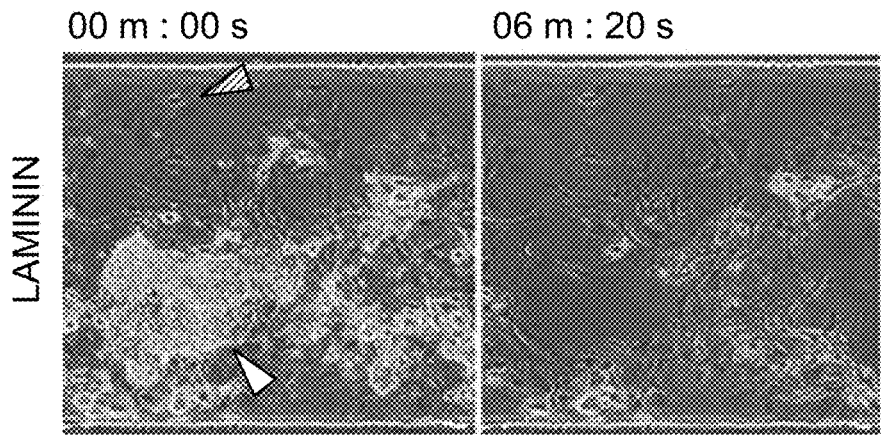
FIG. 7B. Selective detachment of UD-hESC colony from laminin in the presence of MEF (filled arrow).
Figure 7A:
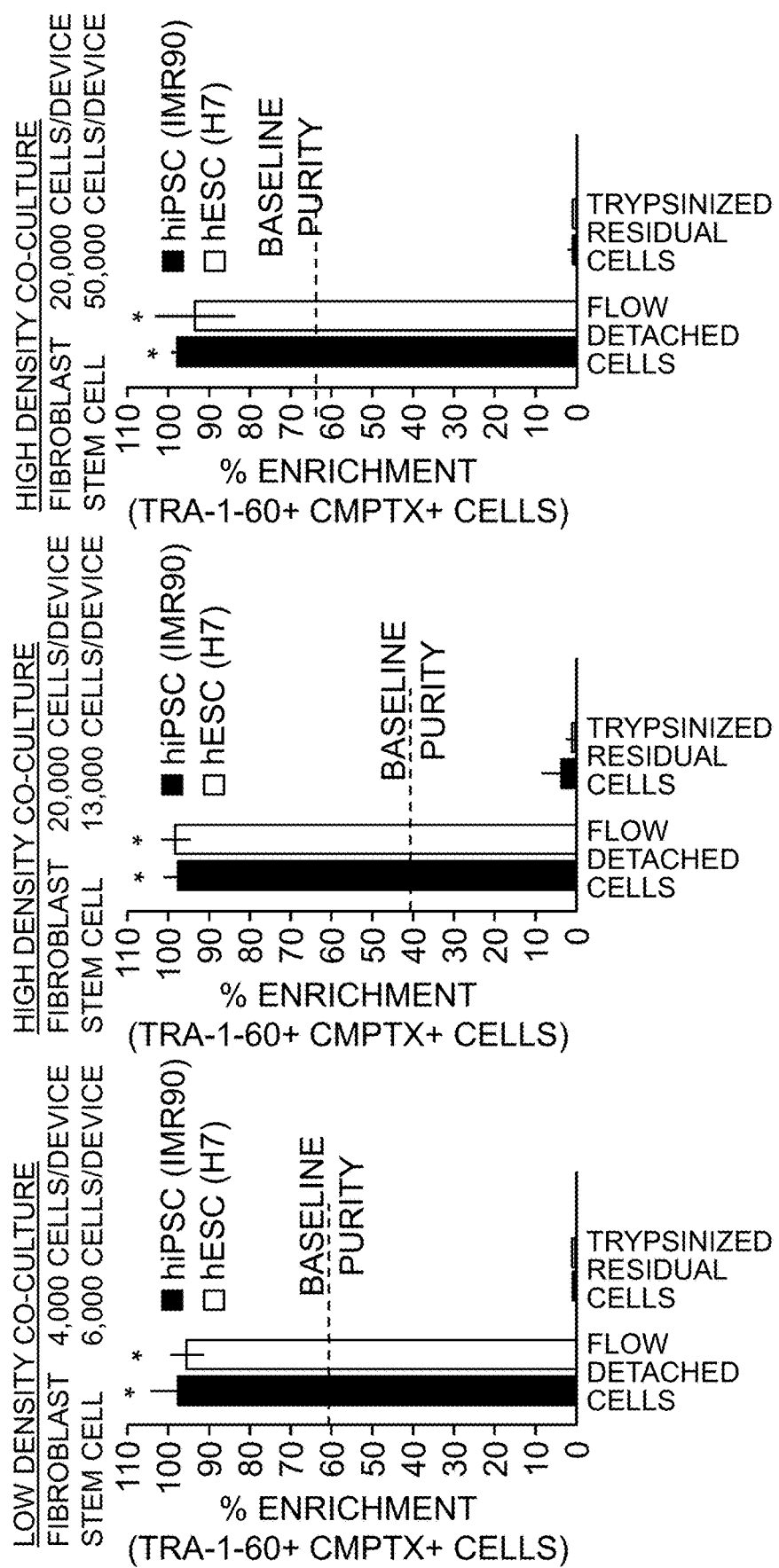
FIG. 7A. Bar graphs presenting flow cytometry-based measurements of enrichment of hiPSCs and hESCs (H7) detached at 85-125 dynes/cm$^2$ shear stress from a co-culture of IMR90 and MEF cells, respectively. Figures also display residual stem cells in the devices post-μSHEAR-based detachment.

To assess the effects of culture purity on μSHEAR-based isolation, extremes of high and low coculture ratios of hiPSCs and IMR90 cells were examined. A relatively low number of hiPSCs and IMR90 cells were seeded with a high hiPSC proportion in the co-culture (~60% starting TRA-1-60+hiPSCs, FIG. 7A); or high number of each cell type in the co-culture with low hiPSC proportion (~40% starting TRA-1-60+hiPSCs, FIG. 7A) or high hiPSC proportion (~60% starting TRA-1-60+hiPSCs) (FIG. 7A). When exposed to a shear stress of 85-125 dynes/cm$^2$, the resulting detachment forces caused selective isolation of hiPSCs with >96% enrichment for all conditions (p<0.05). The percentage of residual adherent hiPSCs in the microfluidic devices post-fluid detachment were further examined, and it was found that fewer than 3% of trypsinized residual cells were hiPSCs (DyLight™ 488-TRA-1-60+ and CMPTX+), indicating significantly high recovery yield of hiPSCs by μSHEAR (FIG. 7A). Similar results were observed with hESCs (H7), with >95% enrichment when co-cultured with commonly used feeder-layer fibroblasts (MEF, FIG. 7A-7B). Since both IMR90 cells and MEF exhibit similar adhesion strengths that differ significantly from hPSCs, these results indicate that the differences in adhesive strength can be exploited to selectively isolate purified hiPSCs or hESCs as intact colonies from a fibroblast-stem cell mixed culture even at extreme ratios of the two cell types.

Figure 8A:
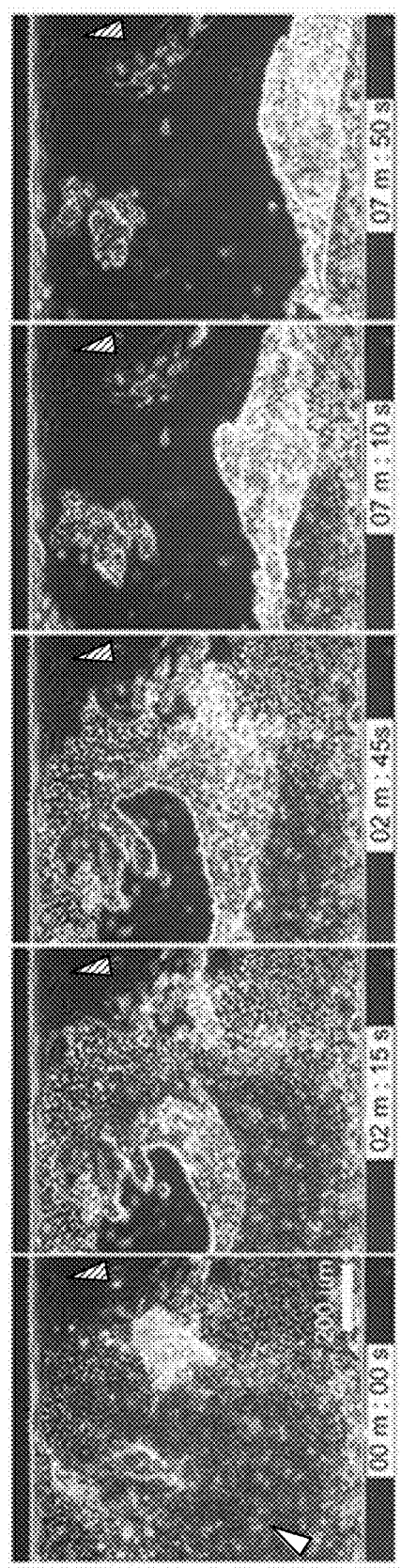
FIG. 8A. Five days co-culture and selective detachment of UD-hiPSC colonies from laminin substrates co-cultured with IMR90 fibroblasts. Colonies were detached selectively at shear stress of 85-125 dynes/cm$^2$.
Figure 8B:
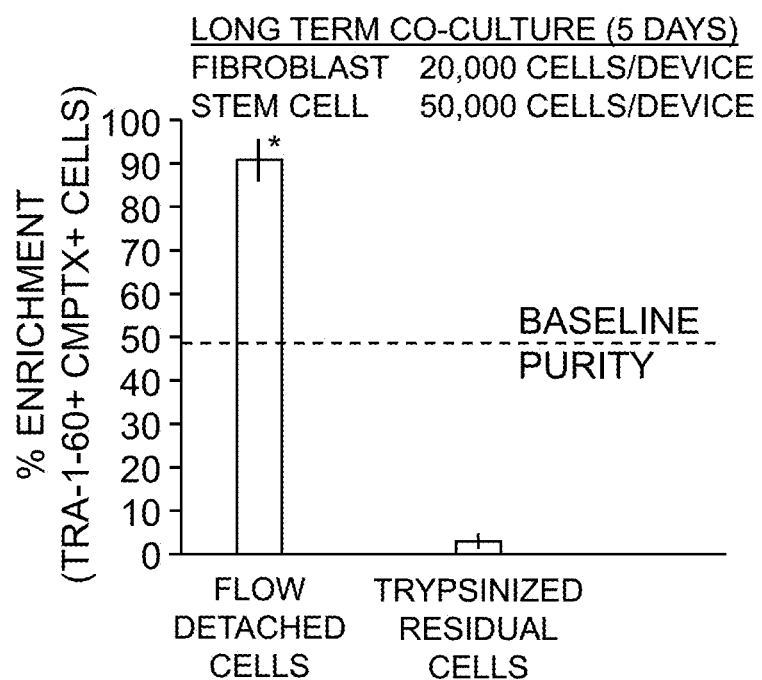
FIG. 8B. Flow cytometry measurements of enrichment of hiPSCs detached at 85-125 dynes/cm$^2$ shear stress from 5 days cultures.

Because hPSCs are routinely cultured for 5-7 days prior to passaging, the efficiency of selective isolation of hiPSC from co-culture via μSHEAR for 5-7 days was evaluated. As indicated in FIG. 8A, hiPSCs were successfully detached and recovered as intact colonies within 8 minutes of exposure to a shear stress of 125 dynes/cm$^2$, with significant enrichment of 93.8±4.9% hiPSC cells (DyLight™ 488-TRA-1-60+ and CMPTX+) compared to a 50% starting hiPSC population (FIG. 8B). Only 3.0±1.2% residual hiPSC cells were observed in the microfluidic devices. Taken together, these studies clearly demonstrate that UD-hiPSCs and UD-hESCs can be selectively isolated from parental fibroblasts or MEF-feeder cells using μSHEAR.

Figure 9A:
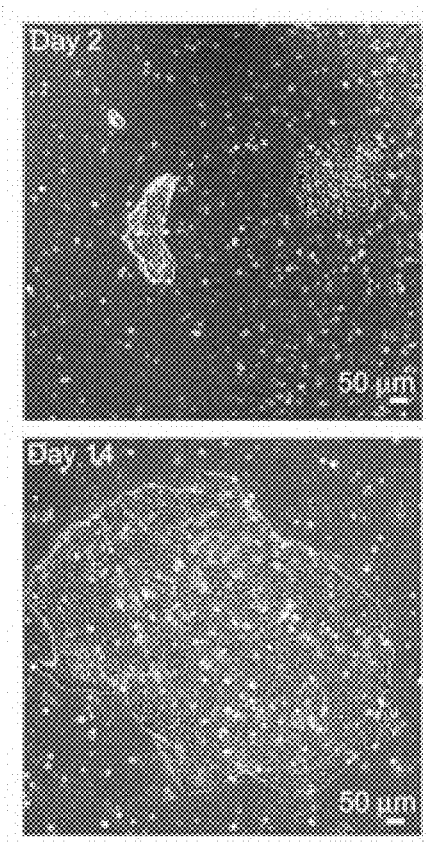
FIG. 9A. Detached UD-hiPS colonies cultured on Matrigel™ adhere as colonies (day 2) and retained self-renewal properties indicated by colony expansion (day 14).
Figure 9B:
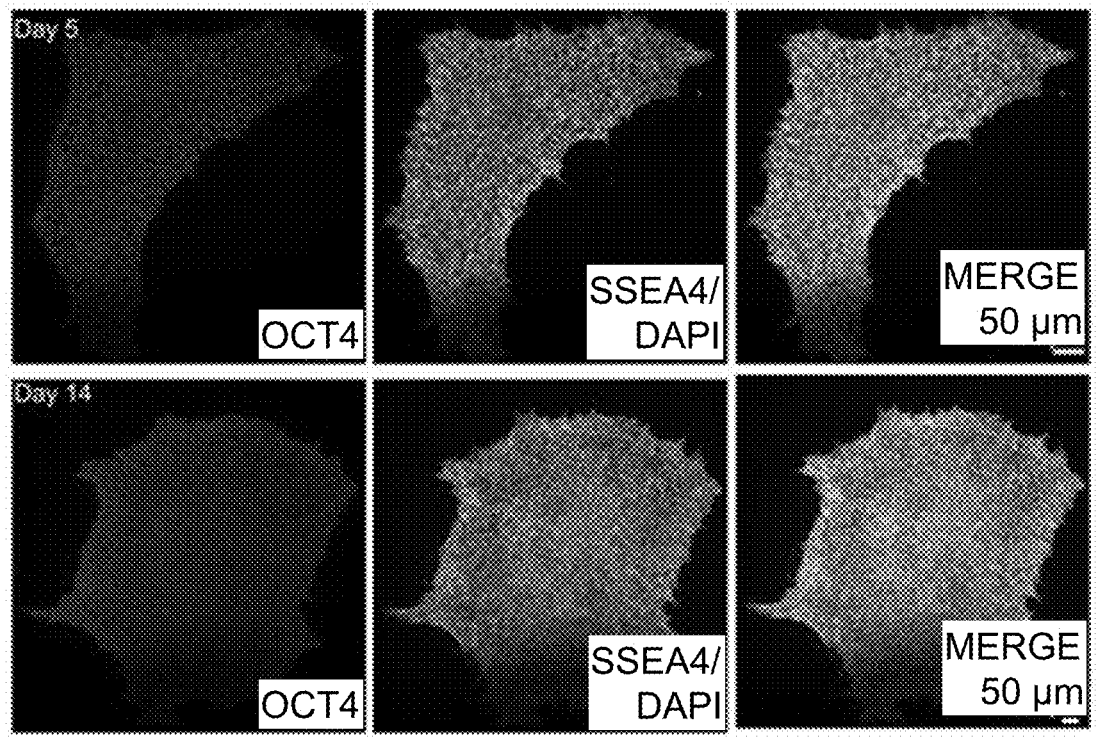
FIG. 9B. Immunofluorescence staining for pluripotency markers SSEA4 and OCT4 showing detached and recovered UD-hiPSC colonies cultured on Matrigel™ retained undifferentiated characteristics (day 5 and day 14).
Figure 9C:
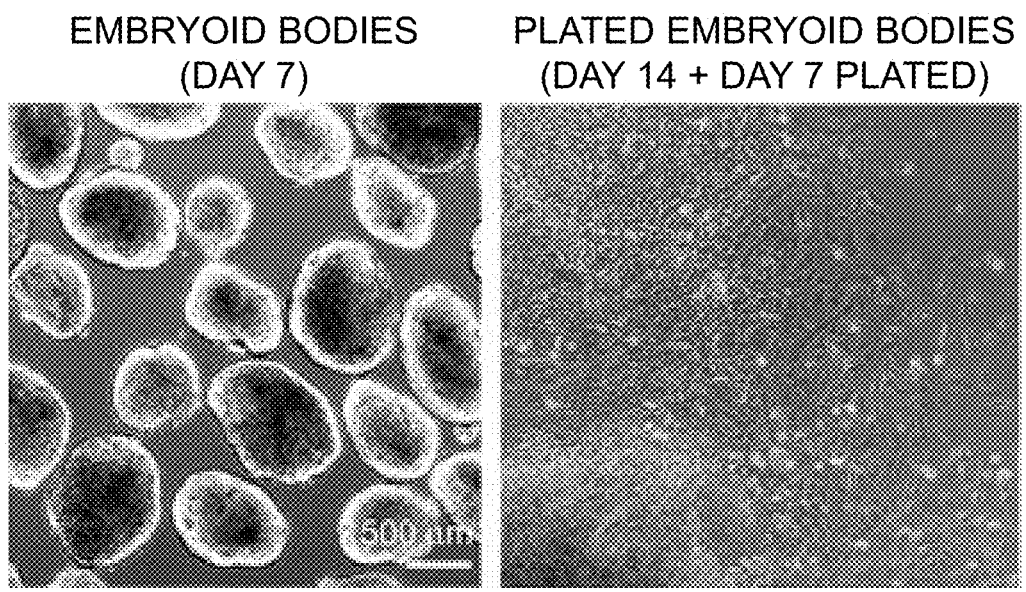
FIG. 9C. μSHEAR-isolated hiPSCs generated embryoid bodies (EBs). After 14 days on rotary culture, EBs were plated for another 7 days.
Figure 9D:
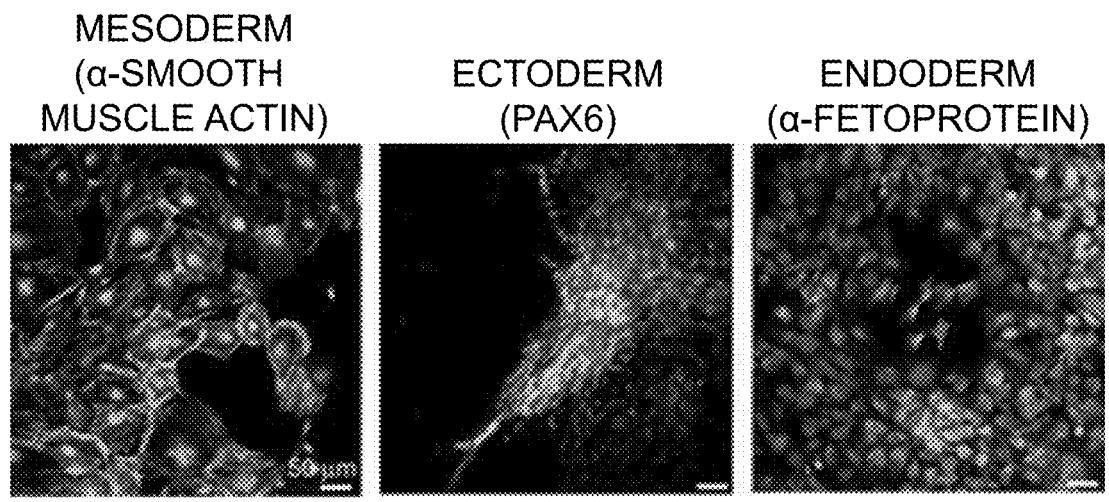
FIG. 9D. Recovered EBs spontaneously differentiated into all three primary germ layers by day 21, mesoderm (α-smooth muscle actin), ectoderm (PAX6), and endoderm (α-fetoprotein). Nuclei were stained with Hoechst.

One consideration for μSHEAR-based hiPSC isolation is whether the detached and enriched hiPSC colonies can be efficiently re-cultured, retain their pluripotent properties, and maintain a stable karyotype. To examine these points, colonies recovered after hydrodynamic detachment were seeded on Matrigel™-coated tissue culture plates in ROCK inhibitor-supplemented mTeSR®1 media and cultured for up to 14 days. The recovered cell clusters initially adhered as small colonies (day 2, FIG. 9A) with the ability to self-renew in tightly packed colonies without any morphological signs of differentiation (day 14, FIG. 9A). The colonies retained their pluripotent phenotype as demonstrated by OCT4 and SSEA4 expression in detached/recovered and cultured colonies at day 5 (FIG. 9B, upper panel) and day 14 (FIG. 9B, lower panel). For karyotype analysis, μSHEAR-isolated hiPSCs were exposed to two rounds of purification with 8-10 days culture on Matrigel™-coated plates and exhibited no chromosomal abnormalities (46, XX). μSHEAR-isolated and cultured hiPSC colonies readily generated embryoid bodies (EBs, FIG. 9C) and differentiated into cell types representing mesoderm (α-smooth muscle actin), ectoderm (PAX6), and endoderm (α-fetoprotein) (FIG. 9D), demonstrating that μSHEAR-based isolation does not adversely affect the normal function of hiPSCs.

Figure 10A:
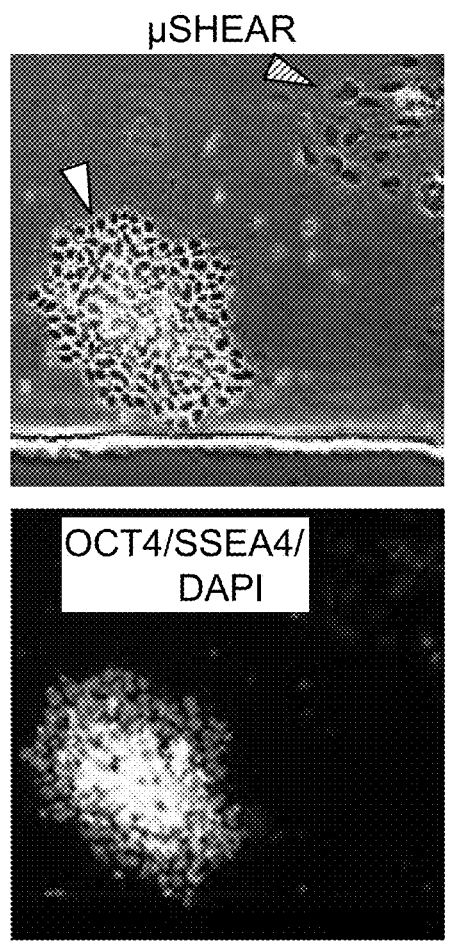
FIG. 10A. Immunostaining for OCT4 and SSEA4 indicating undifferentiated cells (white arrowhead) while negative expression indicates differentiated (filled arrowhead) hiPSCs in μSHEAR.
Figure 10B:
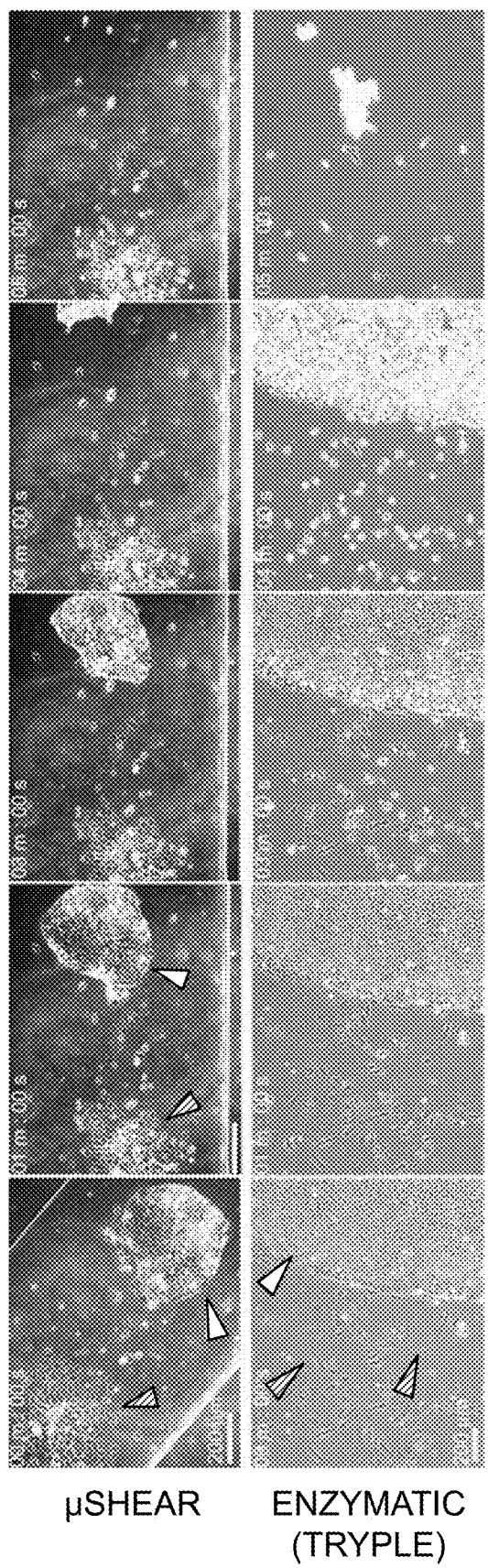
FIG. 10B. Selective detachment of UD-hiPSC colony (white arrowhead) from SD-hiPSCs (filled arrowhead) at 100 dynes/cm$^2$ shear stress (upper panel) using μSHEAR. Lower panel represents detachment of UD-hiPSCs and differentiated cells using a trypsin-like enzyme (TrypLE) where all cells are detached irrespective of cell type.

Example 4

μSHEAR Selectively Isolates Undifferentiated hiPSCs from Differentiated Cells without Affecting Stemness Spontaneous differentiation of hPSCs in culture is a common and significant problem that requires daily, intensive manual maintenance of cultures to remove such cells and preserve the undifferentiated phenotype of the majority of the pluripotent cells (Heng et al., *In Vitro Cell Dev. Biol. Amin.* 40:255-257 (2004); Moon et al., *Mol. Ther.* 13:5-14 (2006); Cho et al., *Proc. Natl. Acad. Sci. USA* 105:3392-3397 (2008)). Based on the unique adhesive signatures of undifferentiated hiPSCs compared to differentiated cells, we evaluated whether the difference in adhesive forces between these two phenotypic states could be exploited to effectively separate undifferentiated pluripotent stem cells from spontaneously differentiated cells. SD-hiPSC cultures with varying levels of differentiation (6%, 10%, 15% or 70% differentiation, TRA-1-60 negative) were dissociated into random colonies and seeded into the microfluidic device and cultured overnight. By visual inspection, it was evident that adherent differentiated cells were spread more than undifferentiated cells and immunostaining with pluripotency markers clearly differentiated between OCT4+ and SSEA4+ UD-hiPSCs compared to SD-hiPSCs not expressing pluripotency markers (FIG. 10A). Consistent with the hiPSC-IMR90 co-culture studies, UD-hiPSCs were selectively detached as intact colonies before detaching SD-hiPSCs (FIG. 10B), demonstrating the ability of μSHEAR to function as a simple and robust hPSC purification strategy. This selective purification was not observed with commonly used enzymatic preparations such as TrypLE (FIG. 10B). Quantitative analysis of the recovered SD-hiPSCs and SD-hESCs (Table 3) further demonstrated the ability to significantly (p<0.0002) enrich live undifferentiated hPSCs with >97% UD-hiPSCs (DyLight™ 488-TRA-1-60+ and CMPTX+) irrespective of the levels of SDhiPSCs, making it a robust method to enrich undifferentiated cells from contaminating cell types.

TABLE 3

| Baseline Purity (TRA-1-60) | Enrichment (μSHEAR) |
| --- | --- |
| 94% | 96.9 ± 1.4% |
| 90% | 97.2 ± 0.9% |
| 85% | 95.9 ± 2.4% |
| 30% | 94.2 ± 5.8% |

Figure 10C:
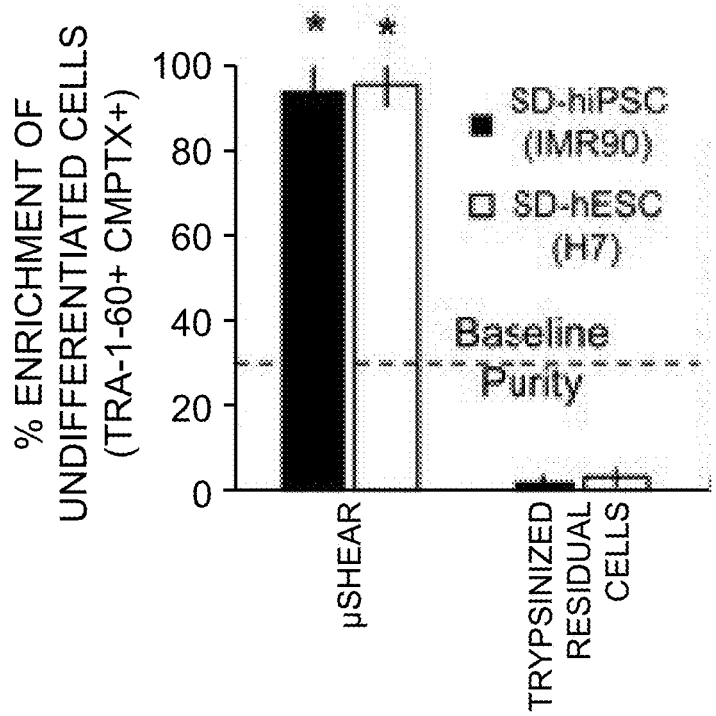
FIG. 10C. Bar graph presents flow cytometry measurements for enrichment of UD-hiPSCs and UD-hESC (H7) detached at 85-150 dynes/cm$^2$ shear stress from a spontaneously differentiated culture using μSHEAR. Plot also shows residual undifferentiated stem cells in devices after μSHEAR-based isolation.
Figure 10D:
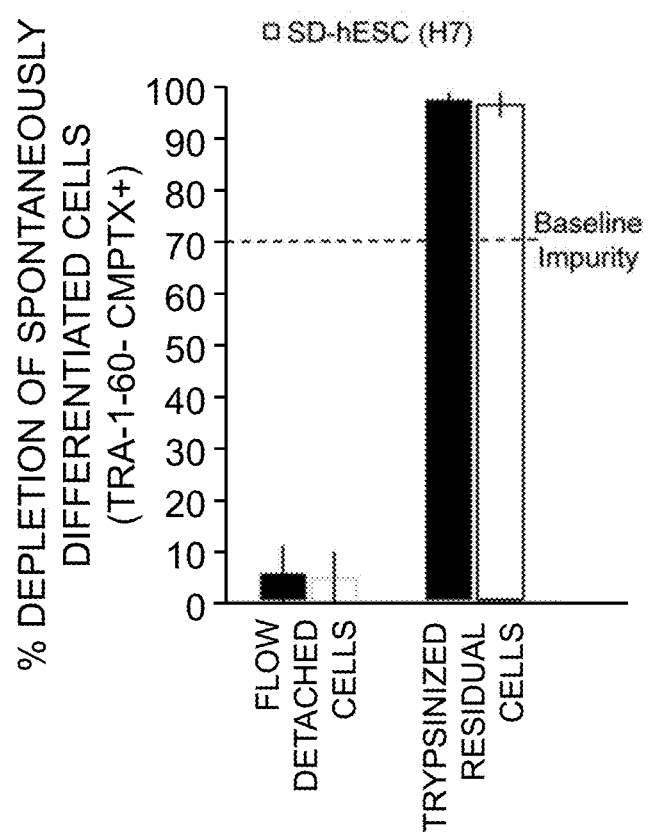
FIG. 10D. Flow cytometry results showing detached UD-hiPSCs (positive for TRA-1-60 and CMPTX) and SD-hiPSCs (positive for CMPTX only). Bar graph shows flow cytometry measurements of contamination of SD-hiPSCs and SD-hESC (H7) in recovered cells detached selectively at a shear stress of 85-125 dynes/cm$^2$.
Figure 10E:
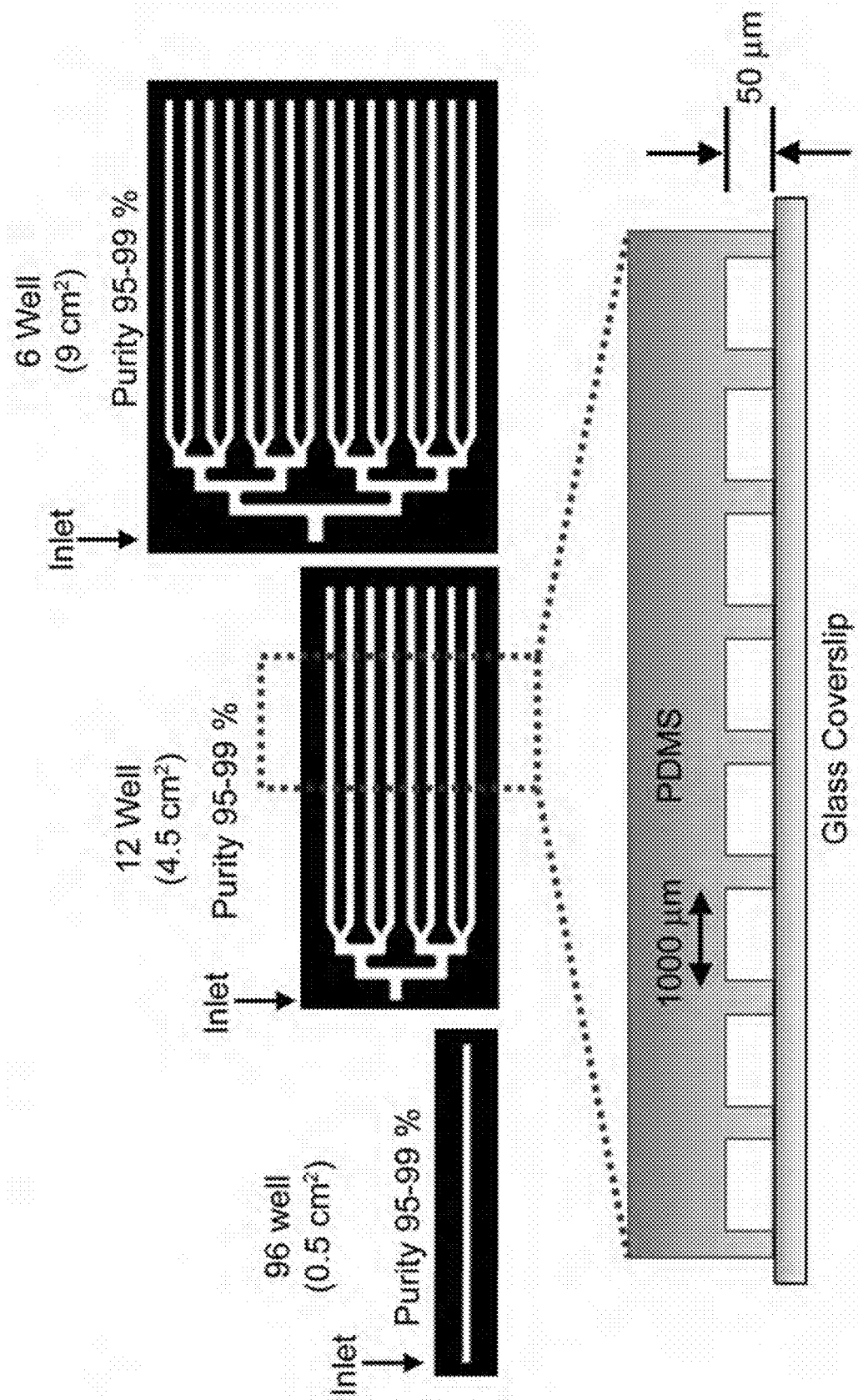
FIG. 10E. Scale-up of μSHEAR from culture area corresponding to a single well of a 96-well plate to a 6-well plate, with consistent enrichment efficiencies for UD-hiPSCs. Cross-sectional schematic of the device.

The undifferentiated stem cell enrichment for H7 hESCs was comparable to hiPSCs (FIG. 10C), demonstrating that μSHEAR is applicable to a wide range of hPSCs. There were only 2-3% residual UD-hiPSCs or UDhESCs in the devices post-μSHEAR purification (FIG. 10C) and less than 5% contaminating spontaneously differentiated cells (TRA-1-60-negative and CMPTX+) in the samples detached at shear stress of 85-125 dynes/cm$^2$ (FIG. 10D), demonstrating high recovery yield. The high-throughput potential of μSHEAR was tested across a wide range of tissue culture surface areas ranging from the equivalent of a 96-well to a 6-well plate (FIG. 10E), with similar high levels of enrichment efficiency observed (95-99%), demonstrating the potential of μSHEAR to perform at the levels of routine cell culture platforms for stem cells.

Figure 11A:
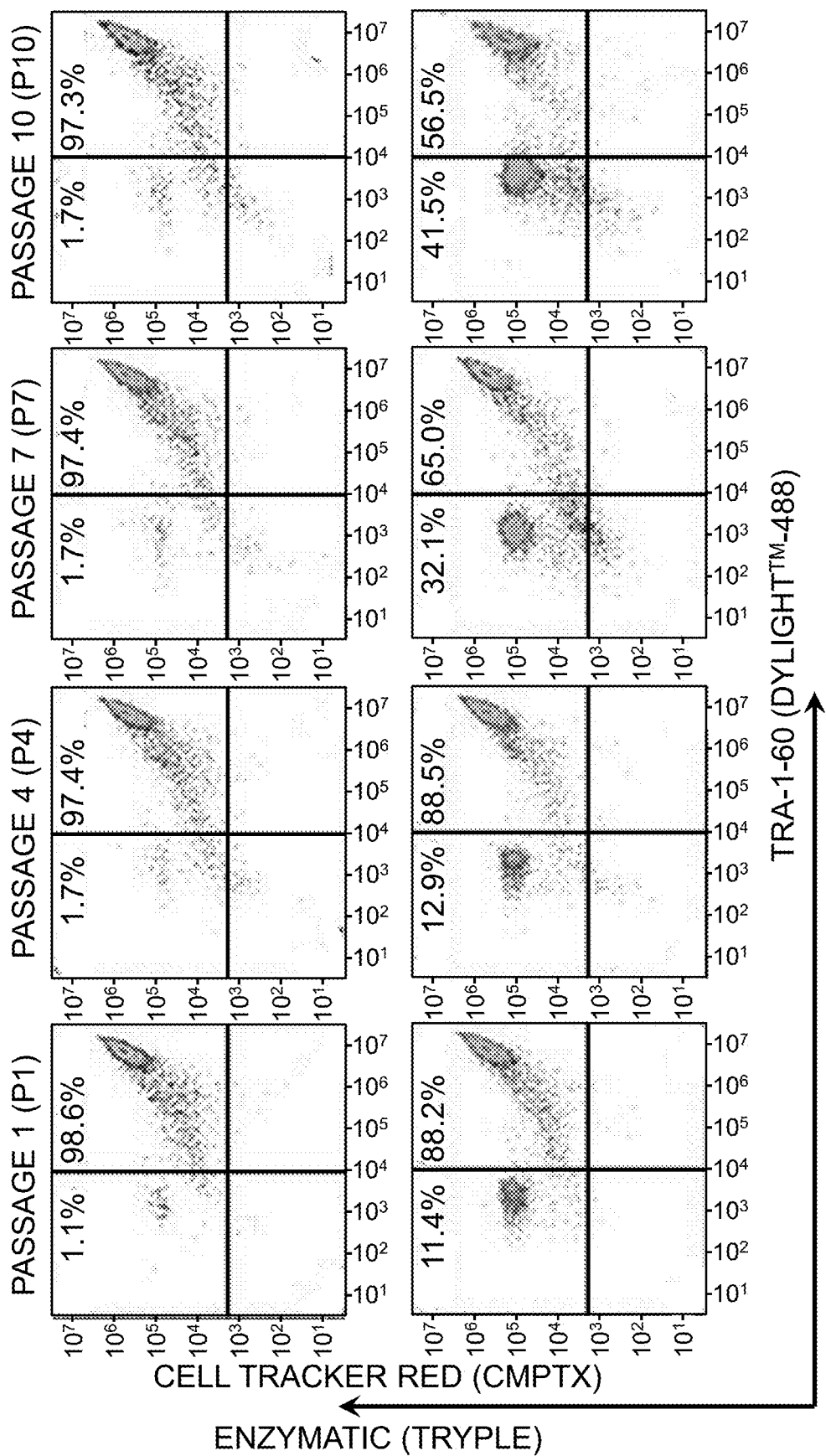
FIG. 11A. Flow cytometry scatter plots showing detached UD-hiPSCs (positive for TRA-1-60 and CMPTX) and SD-hiPSCs (positive for CMPTX only) over a course of 10 passages using μSHEAR-based and conventional enzymatic method. Plot shown is representative of three replicates.
Figure 11B:
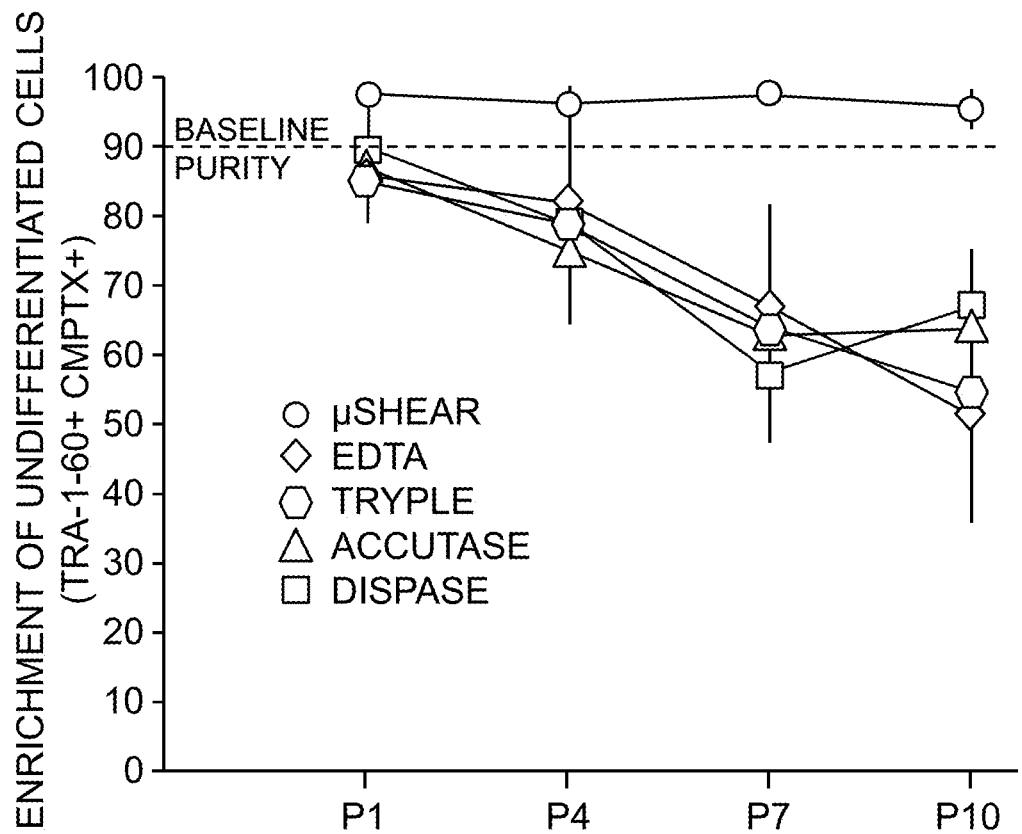
FIG. 11B. Enrichment efficiency of undifferentiated cells when repeatedly passaged by μSHEAR, EDTA, TrypLE, Dispase, or Accutase over the course of 10 passages, *P<0.05, n=3. hiPSCs from same batch (P0) were exposed to the passaging method and the recovered culture was propagated for 5-6 days before next round of treatment. The starting hiPSC culture (P0) was 90% positive for pluripotency marker TRA-1-60.
Figure 11C:
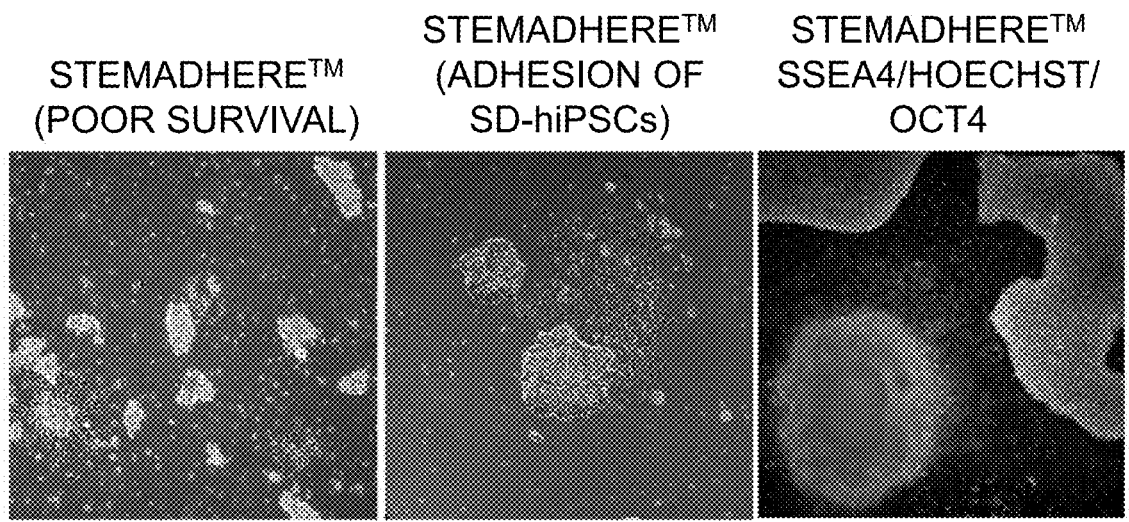
FIG. 11C. Spontaneously differentiated (<10%) hiPSCs cultured on StemAdhere™. Seeded colonies resulted is poor survival (floating colonies, left), with adhesion of differentiated cells along-with undifferentiated cells (middle, right). Differentiated cells did not express pluripotency markers OCT4 and SSEA4.
Figure 11D:
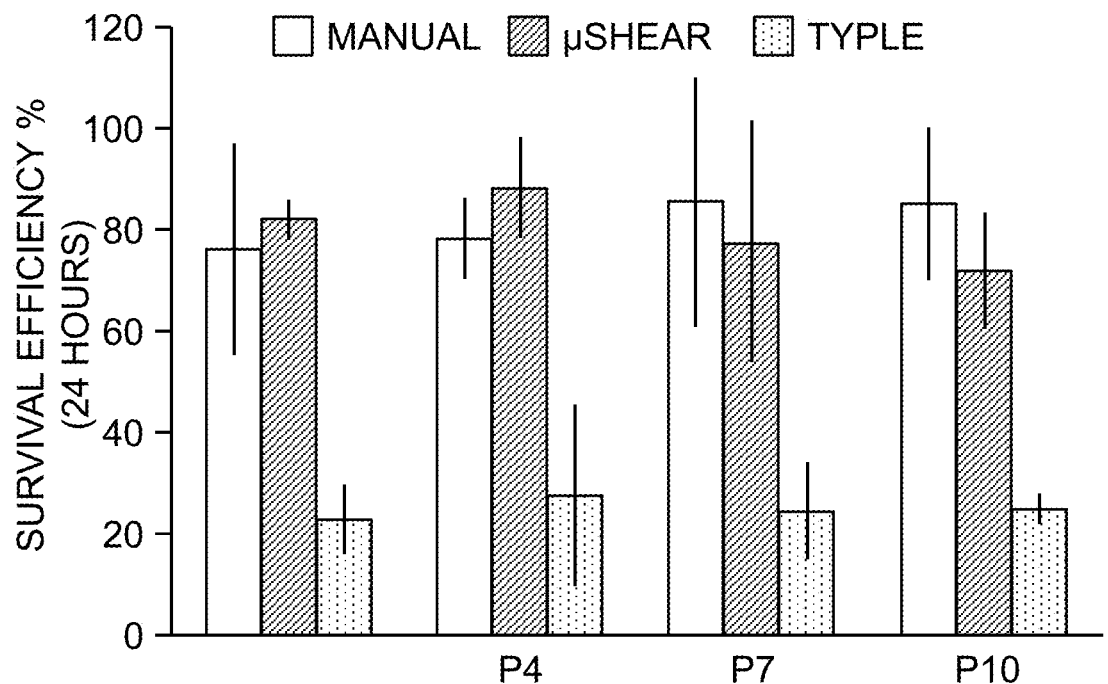
FIG. 11D. Growth curves for cells cultured in mTeSR1 on Matrigel™ after repeated passaging using LSHEAR or manual hand-picking. Curves are plotted over 10 passages starting with an equivalent number of cells at day 0 for each passage (5×10$^4$ cells). For each passage, cell counts are reported (×10$^5$ cells) from triplicate wells at day 1, 3, 5 and day 7. Data are reported average+SD.
Figure 11E:
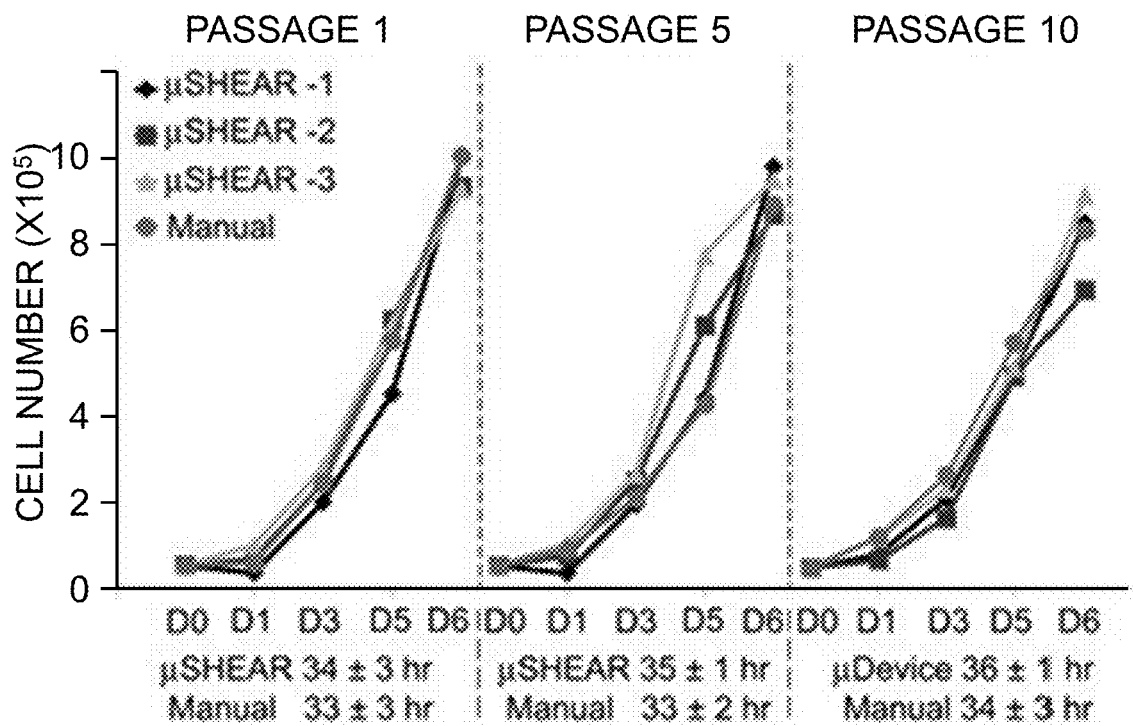
FIG. 11E. Cell survival after 24 hours on Matrigel™ in mTeSR® medium after passaging with μSHEAR, manual hand-picking, or TrypLE, *P<0.05, n=3.

A rigorous characterization of the purified cells was performed to assess the efficacy of μSHEAR over the course of 10 passages, each 5-7 days apart, starting with a low 10% spontaneously differentiated population. As shown in FIG. 11A, μSHEAR-based isolation resulted in repeated high purity (>97%) across 10 passages. In contrast, five routinely used solution or enzymatic passaging approaches (EDTA, TrypLE, Accutase, and Dispase) failed to selectively enrich undifferentiated cells and levels of spontaneous differentiation continuously increased over repeated passaging (FIG. 11B). The use of defined culture substrates, such as E-cadherin (e.g., StemAdhere™), has also been explored for hiPSC passaging (Nagaoka et al., *BMC Dev. Biol.* 10:60 (2010)). However, it was observed that these coated substrates were not selective for UD-hiPSCs, as SD-hiPSCs still adhered to these substrates (FIG. 11C). These results clearly demonstrated the high selectivity of μSHEAR over existing hPSC passaging methods. Because μSHEAR isolates cells as colonies, the resulting survival efficiency (~80%) was significantly higher than TrypLE (<30%)-based passaging and comparable to manual passaging (FIG. 11D). The doubling time of μSHEAR-purified hiPSCs was approximately 33-35 hours over 10 passages (FIG. 11E), equivalent to the doubling time of the hiPSCs maintained in routine culture using manual passaging (32-34 hours).

Figure 11F:
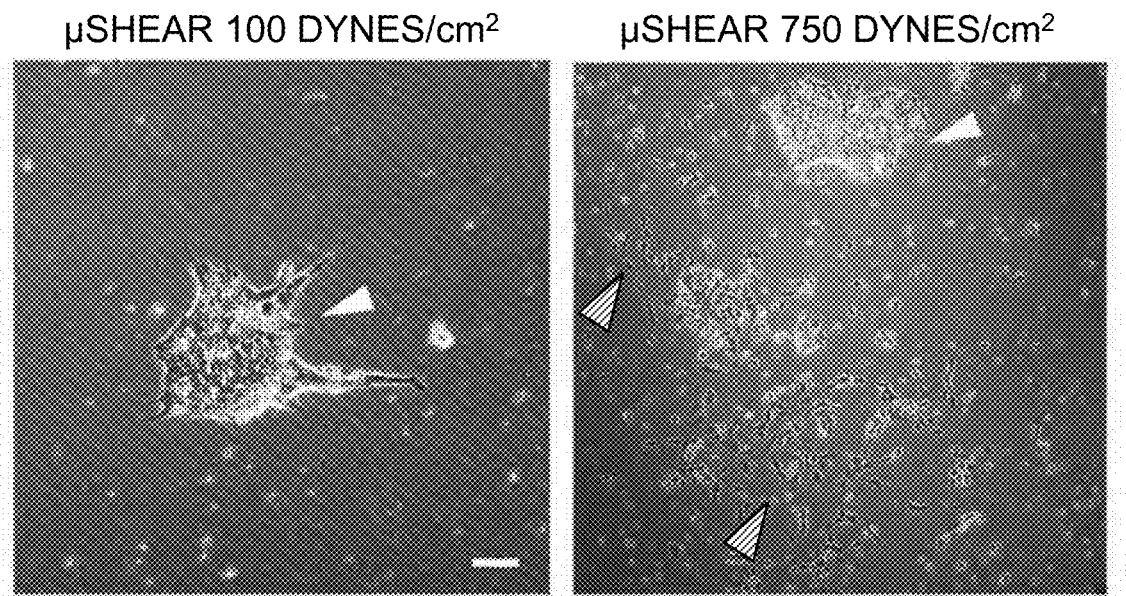
FIG. 11F. Detached colonies cultured on Matrigel™ adhere as undifferentiated colonies (100 dynes/cm$^2$, day 2, white arrows) or partially differentiated colonies (750 dynes/cm$^2$, day 2, filled arrows).
Figure 11G:
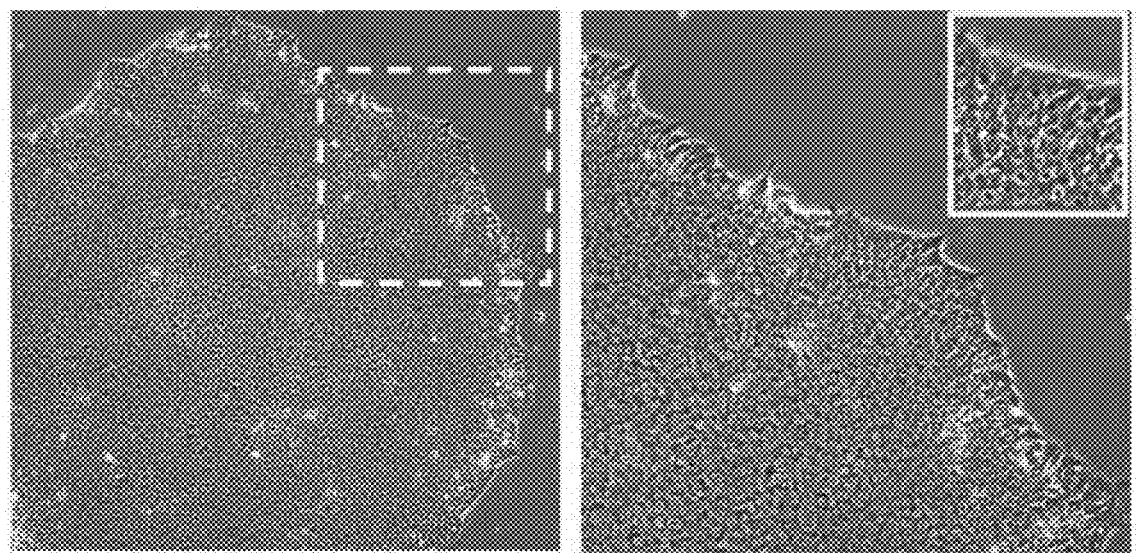
FIG. 11G. UD-hiPSC colonies exposed to repeated 10 device-based passages retained high nucleus-to-cytoplasm ratio and self-renewal properties indicated by colony expansion when cultured on Matrigel™.
Figure 11H:
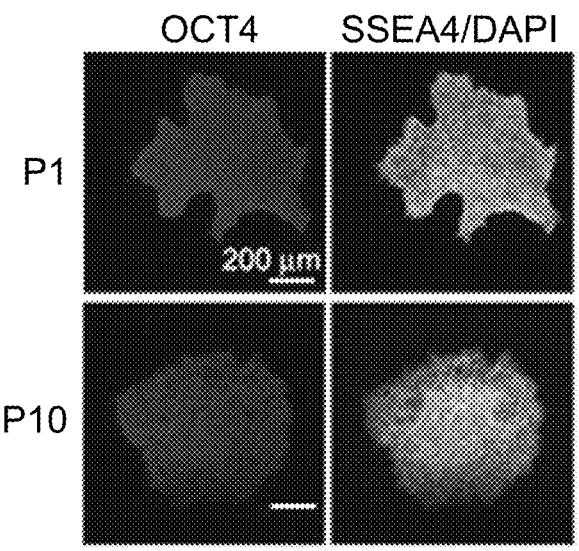
FIG. 11H. Immunofluorescence staining for pluripotency markers SSEA4 and OCT4 showing detached and recovered UD-hiPSC colonies cultured on Matrigel™ retained undifferentiated characteristics across 10 passages.
Figure 11I:
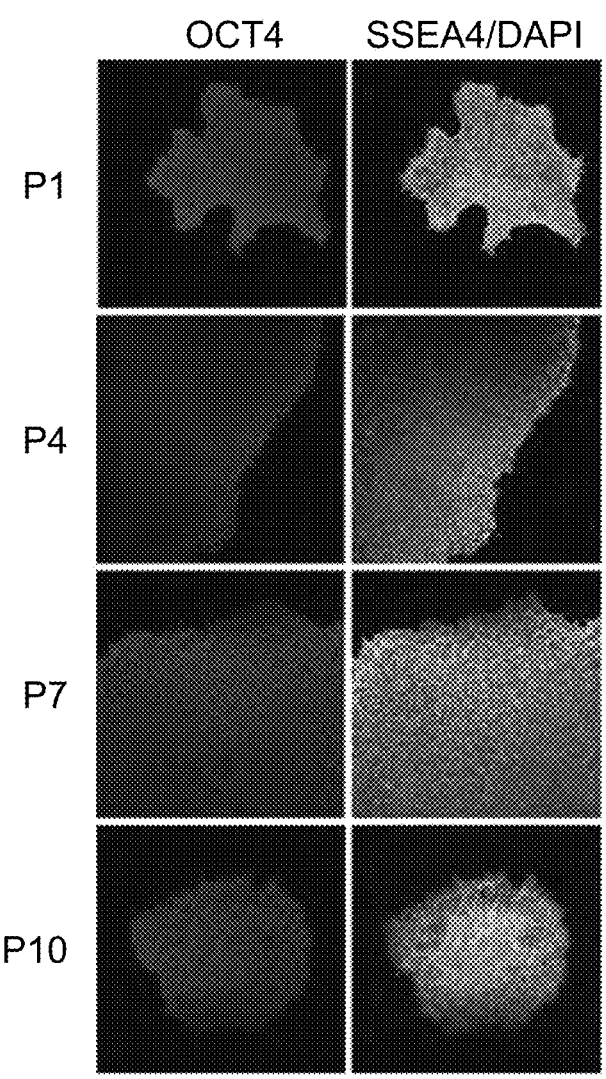
FIG. 11I. Immunofluorescence staining for pluripotency markers SSEA4 and OCT4 showing detached UD-hiPSC colonies cultured on Matrigel™ retained stemness for at least 10 passages using μSHEAR.

When collected and cultured on Matrigel™-coated plates in ROCK inhibitor-supplemented mTeSR®1 media, recovered colonies detached at shear stress of 85-125 dynes/cm$^2$ appeared as undifferentiated colonies as evidenced by day 2 (passage 1) and day 70 (passage 10) images of cultured hiPSC cells (FIG. 11F-11G), with no signs of differentiated cells. In contrast, the application of a high shear stress (750 dynes/cm$^2$) resulted in complete detachment of all SD-hiPSC colonies and the recovered colonies possessed many differentiated cells (day 2, passage 1, FIG. 11F), thus confirming that selective detachment of UD-hiPSCs occurs only at a shear stress range where the differences in adhesive strengths between these phenotypic states can be exploited. The recovered and cultured undifferentiated colonies retained their self-renewal capacity and pluripotency as evidenced by OCT4 and SSEA4 expression at regular intervals between passage 1 and 10 (FIG. 11H-11I). A detailed gene expression analysis was also performed on μSHEAR-passaged and manually passaged hiPSCs after 10 passages (P10) using PCR arrays and compared to the starting P0 population. Heat map analysis indicated that the expression profiles of genes involved in maintaining stemness, self-renewal, pluripotency, and related growth factors were overall similar at P10 to those at P0, independent of passaging method. The overall expression profiles for differentiation and lineage specific genes were either equivalent or down-regulated for both μSHEAR and manual passaged hiPSCs compared to the starting P0 cells. Consistent with this result, hierarchical clustering analysis showed that μSHEAR-passaged hiPSCs clustered closely with manually passaged cells. More importantly, the replicates of μSHEAR-passaged hiPSCs clustered together indicating the robust reproducibility of the hydrodynamic detachment approach. Scatter plot analysis of the gene expression profiles after 10 passages revealed a high degree of similarity between μSHEAR and traditional manual passaging for hiPSCs (FIG. 12). Furthermore, karyotype analysis demonstrated that μSHEAR-passaged hiPSCs exposed to 10 rounds of passaging on Matrigel™-coated plates exhibited no chromosomal abnormalities (46 XX).

Example 5

Characterization of Partially Reprogrammed Cells

Figure 13C:
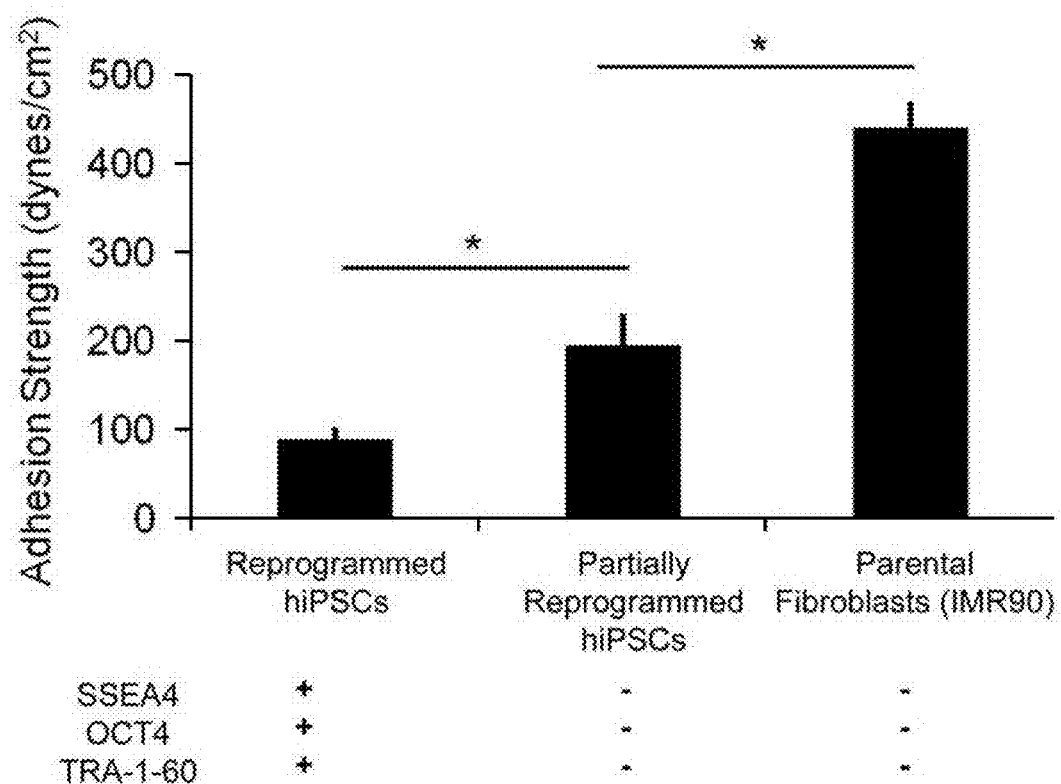
FIG. 13C. Adhesion strength analysis revealed significantly higher adhesion strength for partially reprogrammed cells compared to UD-hiPSCs, and was lower than parental IMR90 cells.
Figure 13D:
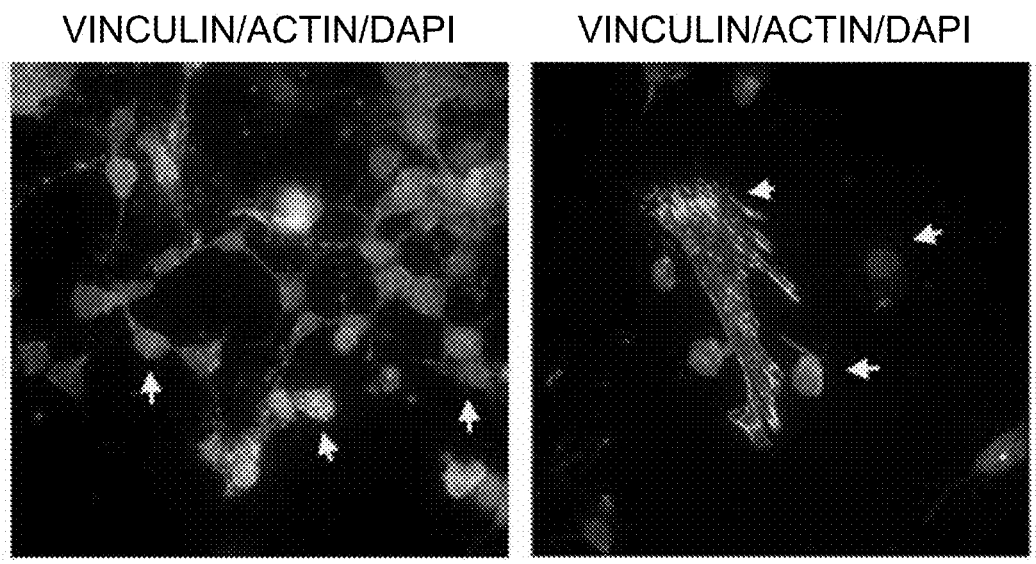
FIG. 13D. Focal adhesion protein localization indicated the presence of well-defined actin stress fibers and vinculin localized to focal adhesion for spread residual parental cells, while transduced round cells exhibited negligible stress fibers or vinculin localization to focal adhesions.

It was observed that the reprogramming culture at the end of the reprogramming process was heterogeneous with a number of cells that failed to become fully reprogrammed hiPSCs (FIG. 13A). IMR90-mimicking spread cells and round epithelial-like cells were observed that did not exhibit any pluripotency markers (FIG. 13B). The spread cells were at relatively much lower frequency than round partially reprogrammed cells (approximately 1:100). Adhesion strength analysis revealed significantly higher adhesion strength for partially reprogrammed cells (196±32 dynes/cm$^2$) compared to UD-hiPSCs, and was lower than parental IMR90 cells (FIG. 13C). Focal adhesion protein localization was determined in residual reprogramming culture obtained after manually removing fully reprogrammed hiPSC. This analysis showed the presence of well-defined actin stress fibers and vinculin localized to focal adhesion for spread residual parental cells, while transduced round cells (negative for pluripotency) exhibited negligible stress fibers or vinculin localization to focal adhesions (FIG. 13D), similar to reprogrammed hiPSCs. The differences in adhesive force is indicative of a distinct "adhesive signature" with induced reprogramming which can be exploited to identify and enrich fully reprogrammed hiPSCs from partially or unreprogrammed cells.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

We claim:

1. A method of isolating a cell of interest from a mixture of animal cells adhered to a substrate, the method comprising:
   a) growing the mixture of animal cells on a substrate in culture such that the cells in the mixture of cells are adhered to the substrate; and
   b) subjecting the mixture of adhered cells comprising the cell of interest and at least one other cell type, which is different from the cell of interest, to a detachment force that provides a wall shear stress in a range wherein said detachment force selectively detaches the at least one other cell type in the mixture of adhered cells and the cell of interest is not detached from the substrate, thereby isolating the cell of interest from the mixture of cells adhered to the substrate, wherein:
   i) the cell of interest is a hiPSC-derived cardiomyocyte and the at least one other cell type is an hiPSC and the detachment force provides a wall shear stress in a range of 70-160 dynes/cm$^2$;
   ii) the cell of interest is a fibroblast and the at least one other cell type is a hiPSC and/or a hESC and the detachment force provides a wall shear stress in a range of 70-160 dynes/cm$^2$; and/or
   iii) the cell of interest is a directly differentiated and/or spontaneously differentiated progeny of a hiPSC and the at least one other cell type is an undifferentiated hiPSC and the detachment force provides a wall shear stress in a range of 70-160 dynes/cm$^2$.

2. The method of claim 1, wherein the method further comprises culturing the isolated cell of interest.

3. The method of claim 1, wherein the method further comprises evaluating the isolated cell of interest by flow cytometry, biochemical analysis and/or gene expression analysis.

4. The method of claim 1, wherein the method does not comprise attaching a detectable label and/or affinity reagent to the mixture of animal cells.

5. The method of claim 1, wherein the detachment force is applied by hydrodynamic force, centrifugal force and/or magnetic force.

6. The method of claim 1, wherein the method is carried out in a microfluidic device.

7. The method of claim 1, wherein the mixture of cultured cells is subjected to the detachment force for 1 to 60 minutes.

8. The method of claim 1, wherein the mixture of cultured cells is subjected to the detachment force for 2 to 20 minutes.

\* \* \* \* \*

UNITED STATES PATENT AND TRADEMARK OFFICE
CERTIFICATE OF CORRECTION

PATENT NO. : 10,570,375 B2
APPLICATION NO. : 16/149918
DATED : February 25, 2020
INVENTOR(S) : Singh et al.

It is certified that error appears in the above-identified patent and that said Letters Patent is hereby corrected as shown below:

In the Specification

Column 6, Line 1: Please correct "average +" to read -- average ± --

Column 7, Line 62: Please correct "LSHEAR" to read -- μSHEAR --

Column 7, Line 67: Please correct "+SD" to read -- ±SD --

Column 22, Line 67: Please correct "50 m" to read -- 50 μm --

Column 23, Line 12: Please correct "(pUSHEAR)" to read -- (μSHEAR) --

Column 23, Line 29: Please correct "(z)" to read -- (τ) --

Column 23, Line 31: Please correct "respectively, is" to read -- respectively, μ is --

Column 24, Line 15: Please correct "4 SD" to read -- ±SD --

Column 28, Line 9: Please correct "LSHEAR" to read -- μSHEAR --

Signed and Sealed this
Twenty-third Day of June, 2020

Andrei Iancu
*Director of the United States Patent and Trademark Office*